US012807946B2

(12) United States Patent
Ui-Tei et al.

(10) Patent No.: US 12,807,946 B2
(45) **Date of Patent: *Nov. 24, 2026**

(54) RNA MOLECULES, CHIMERIC NA MOLECULES, DOUBLESTRANDED RNA MOLECULES, AND DOUBLE-STRANDED CHIMERIC NA MOLECULES

(71) Applicant: THE UNIVERSITY OF TOKYO, Tokyo (JP)

(72) Inventors: Kumiko Ui-Tei, Tokyo (JP); Yoshiaki Kobayashi, Tokyo (JP); Atsushi Sato, Tokyo (JP); Yoshimasa Asano, Tokyo (JP); Yuria Suzuki, Tokyo (JP); Naomi Ledey, Tokyo (JP); Kaoru Saigo, Tokyo (JP); Yukikazu Natori, Kanagawa (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 825 days.

This patent is subject to a terminal disclaimer.

(21) Appl. No.: 18/008,945

(22) PCT Filed: Jan. 17, 2022

(86) PCT No.: PCT/JP2022/001431
§ 371 (c)(1),
(2) Date: Dec. 7, 2022

(87) PCT Pub. No.: WO2022/154122
PCT Pub. Date: Jul. 21, 2022

(65) Prior Publication Data

US 2024/0141337 A1 May 2, 2024

(30) Foreign Application Priority Data

Jan. 15, 2021 (JP) ................................ 2021-005335

(51) Int. Cl.
*C12N 15/113* (2010.01)

(52) U.S. Cl.
CPC ........ *C12N 15/113* (2013.01); *C12N 2310/14* (2013.01); *C12N 2310/3231* (2013.01); *C12N 2310/344* (2013.01)

(58) Field of Classification Search
CPC .............. C12N 15/113; C12N 15/1072; C12N 2310/14; C12N 2310/322; C12N 2310/344; C12N 2320/34; C12N 2320/53; C12N 15/11; C12N 15/1082; C12N 2310/11; A61K 31/7105; A61K 31/712; A61K 31/713
USPC ..................... 435/6.1, 91.1, 91.31, 455, 458; 514/44 A; 536/23.1, 24.5
See application file for complete search history.

(56) References Cited

FOREIGN PATENT DOCUMENTS

| | | | |
|---|---|---|---|
| EP | 2 583 692 | A1 | 4/2013 |
| WO | 2020/033899 | A1 | 2/2020 |
| WO | 2020123410 | A1 | 6/2020 |
| WO | 2021010449 | A1 | 1/2021 |

OTHER PUBLICATIONS

Liu, Xudong, et al. "N-terminal huntingtin knock-in mice: implications of removing the N-terminal region of huntingtin for therapy." PLoS Genetics 12.5 (2016): e1006083. (Year: 2016).*
Roberts et al (Nature Rev., Drug Discovery, vol. 19, pp. 673-694 (2020)) (Year: 2020).*
Kobelt et al (Cancer Gene Therapy in Gene Therapy of Cancer: Methods and Protocols, Methods in Molecular Biology, vol. 2521, pp. 1-15 (Springer Nature 2022)) (Year: 2022).*
Damase et al (Frontiers in Bioengineering and Biotechnology, vol. 9, Article 628137, pp. 1-24 (2021)) (Year: 2021).*
Bost et al (ACS Nano, vol. 15, pp. 13993-14021 (2021)) (Year: 2021).*
U.S. Appl. No. 18/008,903 (Year: 2022).*
U.S. Appl. No. 17/626,867 (Year: 2022).*
International Search Report and the Written Opinion of the International Searching Authority, issued in corresponding International Application No. PCT/JP2022/001431, dated Mar. 15, 2022, 11 pages.
Jackson, A.L. et al. "Expression profiling reveals off-target gene regulation by RNAi" (2003), Nature Biotechnology, vol. 21, No. 6, p. 635-7.
Ui-Tei, K. et al. "Thermodynamic stability and Watson—Crick base pairing in the seed duplex are major determinants of the efficiency of the siRNA-based off-target effect" (2008), Nucleic Acids Res. vol. 36, No. 22, p. 7100-7109.
Office Action dated Feb. 25, 2025 issued in Japanese Patent Application No. 2022-575667 with English Translation. (7 pages).
Hanna Iribe et al; "Chemical Modification of the siRNA Seed Region Suppresses Off-Target Effects by Steric Hindrance to Base-Pairing with Targets"; ACS Omega; 2017; 2; pp. 2055-2064 (10 pages).

(Continued)

*Primary Examiner* — Jane J Zara
(74) *Attorney, Agent, or Firm* — Rothwell, Figg, Ernst & Manbeck, P.C.

(57) ABSTRACT

RNA molecules for RNA interference to target a mutant allele with a point mutation, wherein the molecule has a nucleotide sequence complementary to a nucleotide sequence of a coding region of the mutant allele; and when counted from the base at the 5'-end in the nucleotide sequence complementary to the sequence of the mutant allele: a base at position 5 or 6 is mismatched with a base in the mutant allele; a base at position 10 or 11 is at the position of the point mutation and is identical to the base at the position of the point mutation in the mutant allele; the group at the 2'-position of the pentose in the ribonucleotide at position 8 is modified with $OCH_3$, halogen, or LNA; and the group at the 2'-position of the pentose in the ribonucleotide at position 7 is not modified with any of $OCH_3$, halogen, and LNA.

15 Claims, 35 Drawing Sheets

Specification includes a Sequence Listing.

(56) References Cited

OTHER PUBLICATIONS

Kumiko Tei; "Development of siRNA for Tailored Therapy Targeting the KRAS Oncogene"; Kumiko 2018, vol. 50, No. 1380 with machine translation (7 pages).
Yoshiharu Kobayashi et al.; "[2P-0702] Development of a design method for siRNAs that are effective and specific for all mammalian genes"; 41st AM of MBSJ, Nov. 29, 2018 with machine translations (3 pages).
Jun Sato et al.; "Development of siRNA (SNPD-siRNA) that suppresses KRAS single-base mutation genes by distinguishing them from normal genes"; 44th AM of MBSJ, Dec. 4, 2020, 3P-0344 with machine translation (4 pages).
Extended Search Report dated Aug. 4, 2025 issued in European Patent Application No. 22739527.4 (9 pages).
Kumiko Ui-Tei et al.; Guidelines for the selection of highly effective siRNA sequences for mammalian and chick RNA interference; Nucleic Acids Research; 2004; vol. 32, No. 3, pp. 936-948 (13 pages).
Office Action issued on Jul. 13, 2026 in Indian Patent Application No. 202317053942. (8 pages).
Office Action issued on Aug. 7, 2026 in Chinese Patent Application No. 202280016671.X. (23 pages).
Rodriguez-Lebron et al., "Allele-specific RNA interference for neurological disease", Gene Therapy, 13, 6, Year 2005, Dec. 15, 2005, pp. 576-581. (6 pages).
Dykxhoorn et al., "Determinants of specific RNA interference-mediated silencing of human β-globin alleles differing by a single nucleotide polymorphism", Proceedings of the National Academy of Sciences of the United States of America, vol. 103, No. 15, Year 206, Apr. 11, 2006, pp. 5953-5958. (6 pages).

* cited by examiner

RNA MOLECULES, CHIMERIC NA MOLECULES, DOUBLESTRANDED RNA MOLECULES, AND DOUBLE-STRANDED CHIMERIC NA MOLECULES

CROSS REFERENCE TO RELATED APPLICATIONS

This application is a 35 U.S.C. § 371 National Phase Entry Application of PCT/JP2022/001431, filed Jan. 17, 2022, designating the United States, which claims the benefit of Japanese Application No. 2021-005335 filed Jan. 15, 2021, the disclosures of which are incorporated herein in their entirety by reference.

TECHNICAL FIELD

The present invention relates to RNA molecules, chimeric NA molecules, double-stranded RNA molecules, and double-stranded chimeric NA molecules, for use in RNA interference.

RELATED ART

RNA interference is a simple and efficient way to specifically suppress the expression of a given target gene in cells.

siRNA, however, has been understood to suppress the expression of unintended targets (off-targeted genes) more than expected at the beginning (Jackson, A. L. et al., (2003) Nature Biotechnology vol. 21, pp. 635-637).

Particularly, it has been shown that the stronger the affinity of siRNA to the mRNA of the target, the greater the off-target effects are induced (Ui-Tei, K. et al. (2008) Nucleic Acids Res. vol. 36, pp. 7100-7109).

SUMMARY OF THE INVENTION

Problem to be Solved by the Invention

An object of the present invention is to provide novel RNA molecules, novel chimeric NA molecules, novel double-stranded RNA molecules, and novel double-stranded chimeric NA molecules.

Means to Solve the Problem

During intensive efforts directed toward identifying RNA sequences with reduced off-target effects, the present inventors found that, when the molecules have a mismatch at position 5 or 6 and are modified at the 2'-position of the pentose in each of the ribonucleotides at positions 6-8 or positions 7 and 8, the contribution of nucleotides at positions 10 and 11 in RNA molecules to off-target effects becomes lower. Thus, in RNA interference targeted to a mutant allele of a gene which has a point mutation relative to its corresponding wild-type allele, the present inventors succeeded in mainly suppressing the expression of the mutant allele but not substantially suppressing the expression of the wild-type allele, by designing an RNA molecule in which the base at position 10 or 11 is at the position of the point mutation and is identical to the one in the mutant allele, and using a double-stranded RNA molecule with the aforementioned RNA molecule as a guide strand for RNA interference. The present invention was thus completed.

An aspect of the present invention is an RNA molecule for use in RNA interference to target a mutant allele of a gene, the mutant allele having a point mutation relative to a wild-type allele of the gene, wherein the gene is selected from the group consisting of HTT, ATXN3, ZMYM3, CTNNB1, SMARCA4, SMO, AR, DNM2, KRT14, IL4R, MAPT, MS4A2, PABPN1, RHO, SCN1A, APOB, F12, CLCN7, SCN8A, PCSK9, and KRT6A, and wherein the RNA molecule satisfies the followings:

(1) the molecule has a nucleotide sequence complementary to a nucleotide sequence of a coding region of the mutant allele except for a base specified in (2-1) below; and (2) when counted from the base at the 5'-end of a nucleotide sequence complementary to the nucleotide sequence of the mutant allele, (2-1) a base at position 5 or 6 is mismatched with a base in the mutant allele;

(2-2) a base at position 10 or 11 is at the position of the point mutation and is identical to the base at the position of the point mutation in the mutant allele; and (2-3) the group at the 2'-position of the pentose in each of ribonucleotides at positions 6-8 or positions 7 and 8 is independently modified with $OCH_3$, halogen, or LNA. The halogen may be fluorine. When the base at the 5'-end of the nucleotide sequence specified in (1) above is not adenine or uracil, the base may be replaced by adenine or uracil. When the base at the 3'-end of the nucleotide sequence specified in (1) above is not cytosine or guanine, the base may be replaced by cytosine or guanine. Any of the aforementioned RNA molecules may contain 13-28 nucleotides. Any of the aforementioned RNA molecules may be a chimeric NA molecule wherein one or more ribonucleotides are each replaced by a deoxyribonucleotide, an artificial nucleic acid, or a nucleic acid analog.

A further aspect of the present invention is a double-stranded RNA molecule including a guide strand and a passenger strand, wherein the guide strand is any one of the aforementioned RNA molecules, and the passenger strand is an RNA molecule with a sequence complementary to that of the RNA molecule of the guide strand. An overhang may be present at the 3'-end of the guide strand and/or at the 3'-end of the passenger strand. Either or both of the overhangs may be 1-3 nucleotide(s) long. Any of the aforementioned double-stranded RNA molecules may be a double-stranded chimeric NA molecule in which one or more ribonucleotides are each replaced by a deoxyribonucleotide, an artificial nucleic acid, or a nucleic acid analog.

A further aspect of the present invention is a method for producing an RNA molecule for use as a guide strand in RNA interference, including the step of producing any one of the aforementioned RNA molecules. The RNA molecule may be a chimeric NA molecule wherein one or more ribonucleotides are each replaced by a deoxyribonucleotide, an artificial nucleic acid, or a nucleic acid analog.

A further aspect of the present invention is a method for performing RNA interference to target a mutant allele of a gene in a cell containing a wild-type allele of the gene and the mutant allele of the gene, the mutant allele having a point mutation, wherein the method includes the step of introducing any one of the aforementioned RNA molecules, chimeric NA molecules, double-stranded RNA molecules, or any one of the aforementioned double-stranded chimeric NA molecules into the cell.

A further aspect of the present invention is a therapeutic agent for a patient with a disease or a prophylactic agent for a carrier of the disease, the patient or the carrier having wild-type and mutant alleles of a causative gene for the disease, the mutant allele having a point mutation and being responsible for the disease, wherein the therapeutic agent includes, as an active ingredient, any one of the aforementioned RNA molecules, chimeric NA molecules, double-stranded RNA molecules, or any one of the aforementioned double-stranded chimeric NA molecules. The disease may be one of those listed in Table 1 below.

TABLE 1

| Type | Gene | Gene name | Diseases |
|---|---|---|---|
| Triplet repeat diseases | HTT | Huntingtin | Huntington's disease |
| | ATXN3 | ataxin 3 | Machado-Joseph disease (spinocerebellar ataxia-3) |
| Tumors | ZMYM3 | zinc finger MYM-type containing 3 | medulloblastoma, lung adenocarcinoma, lung squamous cell carcinoma, small cell lung cancer, and medullary thyroid carcinoma |
| | CTNNB1 | catenin beta 1 | non-small cell lung cancer (NSCLC), and hepatocellular carcinoma |
| | SMARCA4 | SWI/SNF related, matrix associated, actin dependent regulator of chromatin, subfamily a, member 4 | ovarian clear cell carcinoma, SMARCA4-deficient thoracic sarcomatoid tumor, and lung tumor |
| | SMO | smoothened, frizzled class receptor | basal cell carcinoma, and medulloblastoma |
| | AR | androgen receptor | prostate cancer, and salivary duct carcinoma |
| Genetic diseases | DNM2 | dynamin 2 | centronuclear myopathy-1 |
| | KRT14 | keratin 14 | congenital epidermolysis bullosa |
| | IL4R | interleukin 4 receptor | atopic susceptibility to disorders such as atopic dermatitis |
| | MAPT | microtubule associated protein tau | frontotemporal dementia (±parkinsonism symptoms), and Alzheimer's disease |
| | MS4A2 | membrane spanning 4-domains A2 | atopic susceptibility to disorders such as atopic dermatitis, and childhood asthma |
| | PABPN1 | poly(A) binding protein nuclear 1 | oculopharyngeal muscular dystrophy (OMPD) |
| | RHO | Rhodopsin | retinitis pigmentosa 4 |
| | SCNIA | sodium voltage-gated channel alpha subunit 1 | early infantile epileptic encephalopathy 6 (Dravet syndrome) |
| | APOB | apolipoprotein B | familial hypercholesterolemia, type 2 |
| | F12 | coagulation factor XII | hereditary angioedema, type III |
| | CLCN7 | chloride voltage-gated channel 7 | autosomal dominant osteopetrosis, type 2 |
| | SCN8A | sodium voltage-gated channel alpha subunit 8 | developmental and epileptic encephalopathy, 13, and Dravet syndrome |
| | PCSK9 | proprotein convertase subtilisin/kexin type 9 | familial hypercholesterolemia, type 3 |
| | KRT6A | keratin 6A | pachyonychia congenita, and epidermolysis bullosa |

A further aspect of the present invention is a method for selecting an RNA molecule, a chimeric NA molecule, a double-stranded RNA molecule, or a double-stranded chimeric NA molecule for use in RNA interference to silence a target gene, the method including the steps of evaluating a gene-specific silencing ability of a plurality of the RNA molecules, the chimeric NA molecules, the double-stranded RNA molecules, or the double-stranded chimeric NA molecules, to the target gene by performing the aforementioned RNAi-based method in vitro using each of the plurality of any one of the aforementioned RNA molecules, chimeric NA molecules, double-stranded RNA molecules, or any one of the aforementioned double-stranded chimeric NA molecules; and selecting an RNA molecule, a chimeric NA molecule, a double-stranded RNA molecule, or a doublestranded chimeric NA molecule having at least a certain level of the gene-specific silencing ability.

EMBODIMENTS OF THE INVENTION

Figure 1:
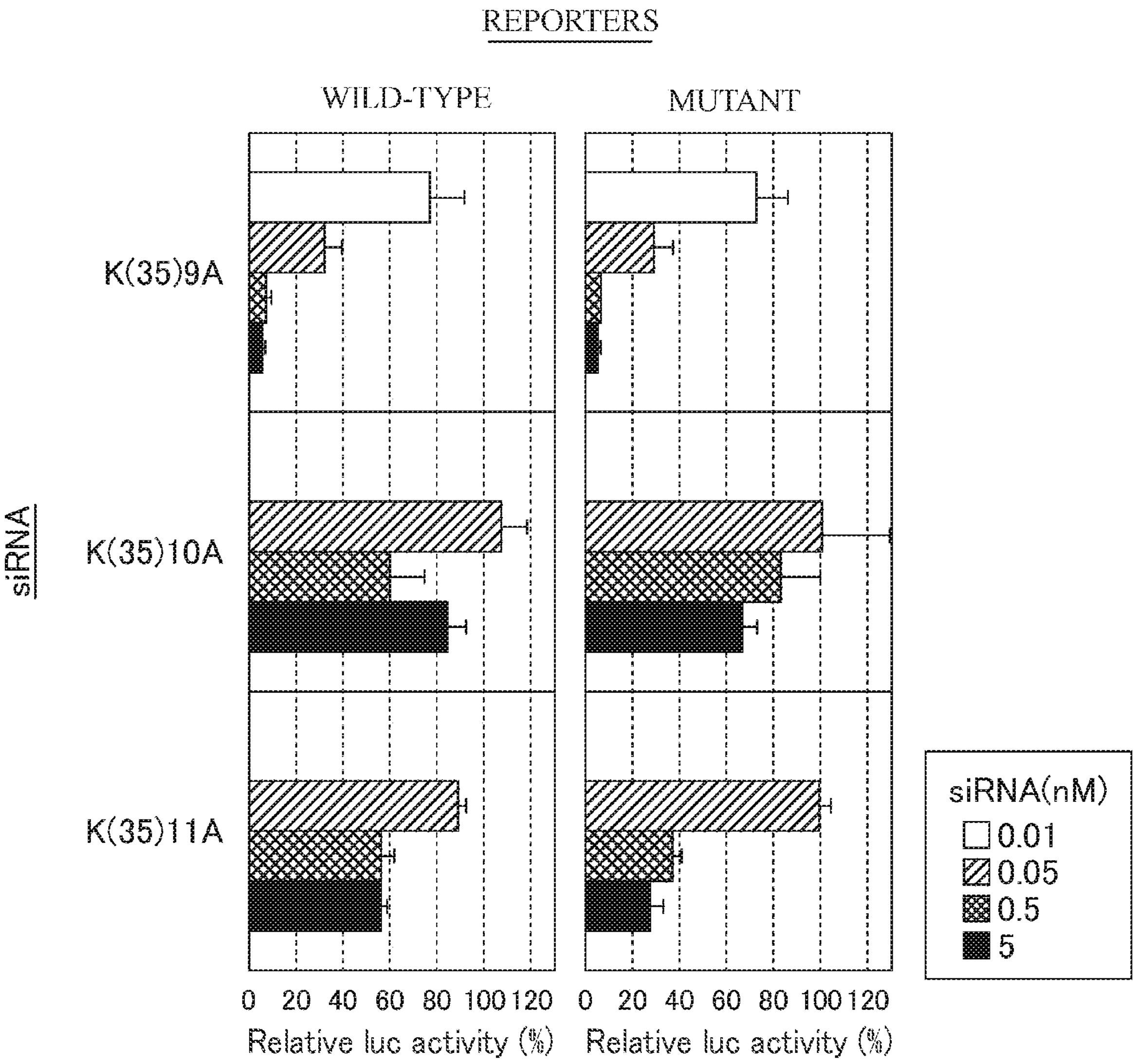
FIG. 1 shows graphs of the results on silencing abilities of siRNAs that target the K-ras gene, in each of which either one of positions 9-11 corresponded to the position of the point mutation, in an example of the present invention.

Objects, characteristics, advantages, and ideas of the present invention are apparent to a person skilled in the art from the description of the present specification, and the person skilled in the art can easily reproduce the present invention from the description of the present specification. Modes for carrying out the invention, specific examples thereof and so forth, which are described below, provide preferable embodiments of the present invention. They are described for the purpose of illustration or explanation, and thus the present invention is not limited thereto. It is apparent to a person skilled in the art that various alterations and modifications can be made on the basis of the description of the present specification within the spirit and the scope of the present invention disclosed in the present specification.

The nucleotide sequences herein are indicated such that their 5'- and 3'-ends are located on the left and right sides, respectively, unless otherwise specified.

RNA Molecules

An embodiment of the present invention is RNA molecules for use in RNA interference to target a mutant allele of a gene, the mutant allele having a point mutation relative to its corresponding wild-type allele. Any gene may be targeted as long as the RNA molecules described herein can be designed for it: however, the target is preferably an oncogene that can transform normal cells by a point mutation, a causative gene responsible for a genetic disease developed by a point mutation, or a causative gene responsible for a disease with an SNP linked to a causative mutation in its coding region. It is preferable that the percentage of the SNP's linking to the causative mutation in a genetic pool is 50% or more. It is more preferable that the percentage is 60% or more, 70% or more, 80% or more, or 90% or more. It is even more preferable that the percentage is 95% or more, 99% or more, or 99.5% or more.

Examples of the oncogene include the ZMYM3, CTNNB1, SMARCA4, SMO, and AR genes. Examples of the causative gene responsible for a genetic disease include the DNM2, KRT14, IL4R, MAPT, MS4A2, PABPN1, SCN1A, APOB, F12, CLCN7, SCN8A, PCSK9, KRT6A, and RHO genes. Examples of the causative gene responsible for a disease with an SNP include the ATXN3 and HTT genes. Diseases that would be caused by these mutations are listed in Table 1.

The RNA molecules herein may consist of any number of nucleotides, and the number may be 13 or more and 100 or less, 13 or more and 50 or less, 13 or more and 28 or less, 15 or more and 25 or less, or 17 or more and 21 or less. More preferably, the number is 19 or more and 21 or less. One or more ribonucleotides may be each replaced by a deoxyribonucleotide, an artificial nucleic acid, or a nucleic acid analog such as inosine or morpholino. Such RNA molecules are herein called "chimeric NA molecules," and the RNA molecules are described as including chimeric NA molecules in the present disclosure.

In the RNA molecules, the base at position 5 or 6, counted from the base at the 5'-end of a nucleotide sequence complementary to that of a mutant allele, is mismatched with the base of the mutant allele. The RNA molecules have a nucleotide sequence complementary to that of the coding region of the mutant allele in the rest of the nucleotide sequence. Furthermore, the RNA molecules may have a sequence other than the nucleotide sequence complementary to that of the coding region of the mutant allele, such as a sequence complementary to the complementary nucleotide sequence, with which the molecules may be self-annealed to function as siRNA. An example of such a single-stranded RNA is Bonac nucleic acid. Alternatively, 1-3 nucleotide(s) may be added to its 3'-end, whose nucleotide sequences are not limited. If the base at the 5'-end of the complementary nucleotide sequence is not adenine or uracil, it may be replaced by adenine, uracil or thymine. If the base at the 3'-end of the complementary nucleotide sequence is not cytosine or guanine, it may be replaced by cytosine or guanine. These modifications enhance the gene expression suppression ability of the RNA molecules when they work as siRNA's guide strands. The RNA molecules may also contain chemical substances in addition to nucleic acids for delivery, to increase membrane permeability, or improve blood retention. For example, the RNA molecules may be conjugated to GalNAc or PEG. The RNA molecules may consist of a sequence other than the nucleotide sequence completely complementary to that of the coding region of the mutant allele except for the base at position 5 or 6. Notably, the RNA molecules have a nucleotide sequence complementary to that of the mutant allele except for the base at position 5 or 6, and their sequence complementarity is preferably 90% or more, more preferably 95% or more, yet more preferably 98% or more, and most preferably 100%. The base at position 5 or 6 may be any base, provided it is mismatched with that of the mutant allele. The base may be A, U, C, G, T, I, or any other artificial nucleic acid or nucleic acid analog as long as it differs from that in the corresponding position of the mutant allele.

Moreover, in the RNA molecules, the base at position 10 or 11, counted from the base at the 5'-end of the nucleotide sequence complementary to that of the mutant allele, is at the position of the point mutation and is identical to the base in the corresponding position of the mutant allele. In the case that the mutated base in the mutant allele is adenine, cytosine, guanine, or thymine, the base at position 10 or 11 of the RNA molecules is adenine, cytosine, guanine, or uracil (or thymine), respectively.

In the RNA molecules, the group at the 2'-position of the pentose in each of their nucleotides at positions 6-8 or positions 7 and 8, counted from the base at the 5'-end of the nucleotide sequence complementary to that of the mutant allele, is independently modified with (i.e., replaced by) $OCH_3$, halogen, or LNA. For example, RNA in which the group at the 2'-position of the pentose is replaced by —$OCH_3$ (hereinafter referred to as a "2'-O-methyl RNA") has a structure represented by the following general formula:

[Chemical Formula 1]

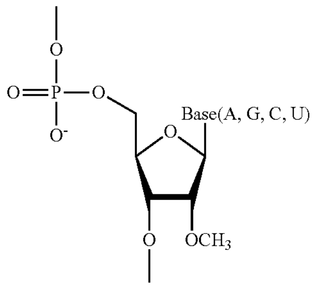

Any halogen may be used, but fluorine is preferred because of its small molecular size. For nucleotides at positions other than those mentioned, some or all of them may be modified; however, it is preferable that none of them is modified. Modifications of nucleotides are not particularly limited and exemplified that the group at the 2'-position of the pentose in the nucleotides is replaced by a group selected from the group consisting of H, OR, R, halogen, SH, SR, $NH_2$, NHR, $NR_2$, CN, COOR, and LNA, in which R is $C_1$-$C_6$ alkyl, alkenyl, alkynyl, or aryl; and halogen is F, Cl, Br, or I.

The IC50 of the RNA molecules for the target is preferably 1 nM or less, more preferably 500 pM or less, and yet more preferably 200 pM or less.

When the RNA molecules are used for RNA interference as a single strand, it is preferable that their 5'-end is phosphorylated or can be phosphorylated in situ or in vivo.

A method of designing the RNA molecules includes the following steps.

First, the step is performed in which a nucleotide sequence of a certain length containing a sequence complementary to that of a mutant allele is designed such that a mutated base in the mutant allele is placed at tenth or eleventh position, counted from the base at the 5'-end. The next step is to place a mismatched base at position 5 or 6, counted from the base at the 5'-end. Then, the group at the 2'-position of the pentose in each of nucleotides at positions 6-8 or positions 7 and 8, counted from the base at the 5'-end, is independently modified with $OCH_3$, halogen, or LNA. In the case that the base at the 5'-end of the complementary nucleotide sequence is not adenine or uracil, the step of replacing it by adenine or uracil or thymine may be performed. Likewise, in the case that the base at the 3'-end of the complementary nucleotide sequence is not cytosine or guanine, the step of replacing it by cytosine or guanine may be performed. Finally, 1-3 base(s) may be added to the 3'-end. In this way, a nucleotide sequence can be designed. A program for causing a computer to perform this design method may be made, and the program may be stored in a computer-readable recording medium. Nucleotides with a sequence designed in this manner can be chemically synthesized according to a routine method.

Double-Stranded RNA Molecules

An embodiment of the present invention is double-stranded RNA molecules in which one of the aforementioned RNA molecules (hereinafter referred to as a "first RNA molecule") serves as a guide strand, and a second RNA molecule with a sequence complementary to that of the first RNA molecule serves as a passenger strand. The second RNA molecule has a sequence complementary to that of the first RNA molecule and forms a duplex with the first RNA molecule under physiological conditions. Their sequence complementarity is preferably 90% or more, more preferably 95% or more, yet more preferably 98% or more, and most preferably 100%.

The passenger strand may have any length and may be considerably shorter than the first RNA molecule. For example, the length of the passenger strand may be equal to or less than half the length of the first RNA molecule. It is, however, preferable that they have the same length. When the passenger strand is shorter than the first RNA molecule, the latter has a single-stranded portion. This portion may be left single-stranded, or alternatively, a third RNA molecule complementary to the first RNA molecule may be annealed to the single-stranded portion. In the case that the second and third RNA molecules occupy the entire length of the first RNA molecule, the resulting double strand is identical to the one with a nick present on a single passenger strand to divide it into two.

The double-stranded RNA molecules may have two blunt ends, or alternatively, they may have an overhang at the 3'-end of either or both first and second RNA molecules serving as the guide and passenger strands, respectively. The overhang(s) may have any number of nucleotides but is/are preferably of 1-3 nucleotides long.

The double-stranded RNA molecule may be a double-stranded chimeric NA molecule in which 1-3, 4-6, 7-9, 10-12, 13-15, 16-18, 19-21, 22-24, or 25 or more ribonucleotides, or all ribonucleotides are each replaced by a deoxyribonucleotide, an artificial nucleic acid such as morpholine, or a nucleic acid analog such as glycol nucleic acid. The replaced positions are not limited.

The nucleotides in the passenger strand may be modified; however, it is preferable that they are not modified. Modifications of nucleotides are not particularly limited, and, for example, the group at the 2'-position of the pentose in the nucleotides may be replaced by a group selected from the group consisting of H, OR, R, halogen, SH, $SR_1$, $NH_2$, NHR, $NR_2$, CN, COOR, and LNA, in which R is $C_1$-$C_6$ alkyl, alkenyl, alkynyl, or aryl; and halogen is F, Cl, Br, or I.

Passenger strands can also be easily designed and easily produced using known techniques. A guide strand and a passenger strand may be linked to each other by a linker. The linker may be formed of any material, and examples include peptides and PEG.

RNA Interference

An embodiment of the present invention is a method for performing RNA interference by which a mutant allele with a point mutation is targeted in cells containing the wild-type allele of a gene of interest and a mutant allele of the gene. This method includes the step of introducing the first RNA molecule that may include a chimeric NA molecule, or one of the aforementioned double-stranded RNA molecules that may include a double-stranded chimeric NA molecule, into the cells containing the wild-type allele and the mutant allele.

RNA interference can be readily performed using known techniques. The expression of a target can be reduced by introducing the first RNA molecule or the double-stranded RNA molecule into, for example, culture cells or a human or non-human individual organism expressing the target gene.

The use of the aforementioned first RNA molecules or double-stranded RNA molecules in RNA interference makes it possible to primarily suppress the expression of the mutant allele of the gene of interest, substantially not suppressing the expression of the wild-type allele. Here, the expression of the wild-type allele may be suppressed up to the level at which the wild-type allele is functional and a normal phenotype is exhibited. The expression of the mutant allele should be inhibited at least to the level at which the mutant allele is not functional and the abnormal phenotype is not exhibited. This enables, for example, cells to become functional normally without developing the phenotype due to a mutation even when the mutant allele carries a dominant mutation.

Agents

An embodiment of the present invention is a therapeutic agent for a patient with a disease or a prophylactic agent for a carrier of the disease, the patient or the carrier having wild-type and mutant alleles of a causative gene for the disease, the mutant allele of the causative gene having a point mutation and being responsible for the disease, wherein the therapeutic or prophylactic agent includes, as an active ingredient, any of the aforementioned RNA molecules including any one of the aforementioned chimeric NA molecules or any one of double-stranded RNA molecules including any one of the aforementioned double-stranded chimeric NA molecules. Carriers as used herein refer to individuals with a mutant allele of a causative gene for a disease who have not developed it and may develop it in the future. Prophylactic agents for carriers help prevent them from developing the disease due to the mutant allele of the causative gene.

Here, the cause of the disease may not be the point mutation but rather a different mutation and a certain percentage of patients or carriers of the disease have the point mutation. In the latter cases, the point mutation is preferably associated with the causative mutation. The aforementioned percentage is preferably 50% or more: more preferably, 60% or more, 70% or more, 80% or more, or 90% or more: and yet more preferably, 95% or more, 99% or more, or 99.5% or more, although not specifically limited. If the percentage is low, the patient or carrier may be examined to determine whether they have the point mutation before administering the agent. In these cases, healthy persons other than the patient or carrier preferably do not have the point mutation.

Examples of the former cases are genetic diseases and tumors that are caused by a point mutation. The genetic diseases are not limited as long as their development is caused by a point mutation, among which some examples are given in Table 1. Likewise, the tumors are not limited as long as they are caused by a point mutation in an oncogene, among which some examples are given in Table 1.

Examples of the latter include triplet repeat diseases. Triplet repeat diseases are known to be caused by 5-40 repeats and 36-3000 repeats of a triplet sequence such as CAG in healthy individuals and patients, respectively. For example, in the ATXN3 mutant gene, which is a causative gene for Machado-Joseph disease, an SNP in which G immediately after a CAG repeat is mutated to C can be found. This mutation could be the target of the siRNA of the present disclosure. The triplet repeat diseases are not limited, among which some examples are given in Table 1.

Any method can be used for the administration of the agents disclosed herein; however, injection is preferable, and intravenous injection is more preferable. In such cases, in addition to the active ingredient, other ingredients such as pH adjusters, buffers, stabilizers, tonicity adjusting agents, or local anesthetics may be added to the therapeutic agents.

The dosage of the therapeutic agents is not limited and is selected as appropriate based on, for example, the efficacy of the ingredients contained, the mode of administration, the route of administration, the type of the disease, attributes of a subject (e.g., weight, age, medical conditions, and history of use of other medicaments), and the discretion of a physician in charge.

Selection Methods

An embodiment of the present invention is a method for selecting RNA molecules, chimeric NA molecules, double-stranded RNA molecules, or double-stranded chimeric NA molecules for use in RNA interference to silence a target, the selection method including the steps of evaluating a gene-specific silencing ability of a plurality of the aforementioned RNA molecules, chimeric NA molecules, double-stranded RNA molecules, or double-stranded chimeric NA molecules by performing RNA interference in vitro using them; and selecting RNA molecules, chimeric NA molecules, double-stranded RNA molecules, or double-stranded chimeric NA molecules having at least a certain level of the gene-specific silencing ability.

In performing RNA interference in vitro, a wild-type allele and a mutant allele with a point mutation, of a gene are used as targets, and a molecule is selected which does not suppress the expression of the wild-type allele to a given level but suppresses the expression of the mutant allele to a level equal to or lower than a given level. By using this procedure, one or more molecules that suppress the expression of the mutant allele but do not suppress the expression of the wild-type allele can be obtained. Here, the given level may be any level, but is preferably 50%, more preferably 70%, and even more preferably 90%.

Methods for the assay using RNA interference in vitro are common knowledge in the art, and the selection of genes, selection of cells, and introduction of RNA molecules into cells, etc. are obvious to those skilled in the art.

EXAMPLES

Method

HeLa cells cultured in DMEM supplemented with 10% FBS were seeded at $1 \times 10^5$ cells/mL on 24-well plates and co-transfected with each double-stranded siRNA with 100 ng of a reporter and 100 ng of plasmid (pGL3) as an internal standard, using 2 μL of lipofectamine 2000. The concentrations of the double-stranded siRNAs are shown in the figures. siGY441 was introduced as a control for siRNA. The cells were harvested after 24 hours, and firefly and Renilla luciferase activities were measured using a dual-luciferase reporter assay system (Promega). Renilla luciferase activity was normalized from the firefly luciferase activity. The results obtained for the double-stranded siRNAs are presented in graphs, relative to those for siGY441, which were set to 100%.

Example 1

In this example, the K-ras gene was used as a target gene to be silenced.

Example 1-1

This example shows that, by matching position 10 or 11 of each siRNA with the position of the point mutation in the A-mutant allele of the K-ras gene (c. 35G>A) (hereinafter, referred to as the "A-mutant allele"), the RNA molecules exhibit a higher specificity for silencing abilities to the A-mutant allele of the K-ras gene (35G>A) than to the wild-type allele of the K-ras gene (hereinafter, referred to as a "wild-type allele").

First, as reporters for examining gene silencing effects, DNAs with the same nucleotide sequences as the wild-type allele of the K-ras gene (wt) and the A-mutant allele of the K-ras gene (c. 35G>A) were chemically synthesized and inserted into the 3'-UTR of the luciferase gene in an expression vector (psiCHECK) to construct wild-type and A-mutant K reporters, respectively. The sequences of the segments incorporated into the vectors are indicated below.

```
Wild-type K reporter:
5'-TGGTAGTTGGAGCTGGTGGCGTAGGCAAGAGTG-3'    (SEQ ID NO. 4)

3'-ACCATCAACCTCGACCACCGCATCCGTTCTCAC-5'    (SEQ ID NO. 5)

A-mutant K reporter:
5'-TGGTAGTTGGAGCTGATGGCGTAGGCAAGAGTG-3'    (SEQ ID NO. 6)

3'-ACCATCAACCTCGACTACCGCATCCGTTCTCAC-5'    (SEQ ID NO. 7)
```

Next, double-stranded RNAs with the following sequences were chemically synthesized for siRNAs. The positions 9, 10, and 11 in siRNAs, K(35)9A, K(35)10A, and K(35)11A, respectively, correspond to the position of the point mutation in the A-mutant allele of the K-ras gene (c. 35G>A). In the following sequences, base pairs in the position corresponding to the position of the point mutation are enclosed in rectangles.

```
K(35)9A:
5'-GUUGGAGCUGAUGGCGUAGTT-3'    (SEQ ID NO. 8)

3'-TTCAACCUCGACUACCGCAUC-5'    (SEQ ID NO. 9)

K(35)10A:
5'-UUGGAGCUGAUGGCGGUAGGGCA-3'    (SEQ ID NO. 10)

3'-UCAACCUCGACUACCGCAUCC-5'    (SEQ ID NO. 11)

K(35)11A:
5'-UGGAGCUGAUGGCGUAGGCAA-3'    (SEQ ID NO. 12)

3'-CAACCUCGACUACCGCAUCCG-5'    (SEQ ID NO. 13)
```

FIG. 1 shows gene silencing effects of the siRNAs.

K(35)9A had a strong silencing effect on both A-mutant and wild-type alleles. K(35)10A and K(35)11A strongly suppressed the expression of the A-mutant allele more than that of the wild-type allele although their silencing effects were slightly reduced.

Example 1-2

This example shows that the silencing abilities of the RNA molecule to the A-mutant allele become stronger and its specificities become much higher by, in addition to matching position 11 of an siRNA with the position of the point mutation in the A-mutant allele, changing the base at the 5'-end of the siRNA's guide strand from guanine to uracil and changing the base at the 5'-end of the passenger strand from uracil to guanine.

The wild-type and A-mutant K reporters were used as reporters for examining gene silencing effects. A double-stranded RNA with the following sequences was chemically synthesized for an siRNA, and K(35)11A was used as a control. In the following sequences, a base pair in the position corresponding to the position of the point mutation, and the pairs of the modified bases at the 5'-ends of the guide and passenger strands are enclosed in rectangles.

```
K(35)11Arev:
5'-GGGAGCUGAUGGCGUAGGAAA-3'    (SEQ ID NO. 14)

3'-CACCCUCGACUACCGCAUCCU-5'    (SEQ ID NO. 15)
```

Figure 2:
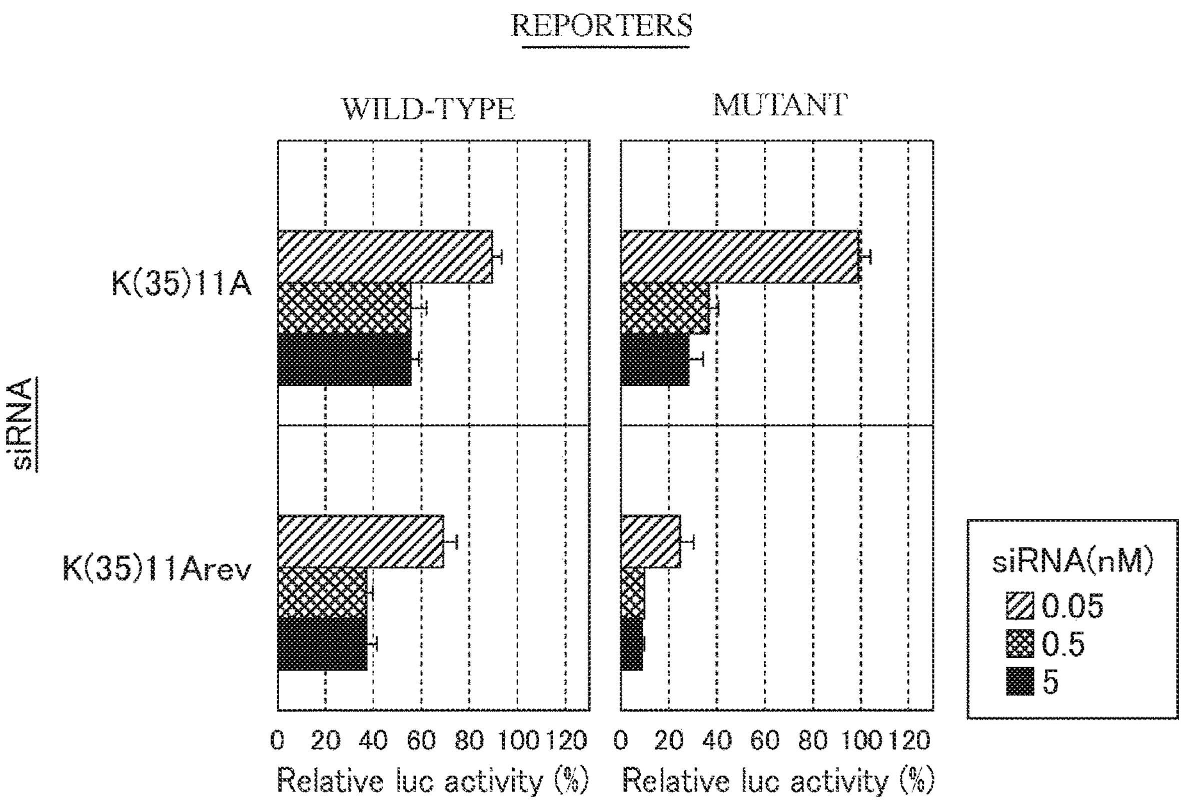
FIG. 2 shows graphs of the results on silencing abilities of an siRNA that targets the K-ras gene, in which position 11 corresponded to the position of the point mutation, the base at the 5'-end of the guide strand was changed from guanine to uracil, and the base at the 5'-end of the passenger strand was changed from uracil to guanine, in an example of the present invention.

FIG. 2 shows gene silencing effects of the siRNAs.

K(35) 11A strongly suppressed the expression of the A-mutant allele more than that of the wild-type allele, whereas K(35)11Arev exerted a stronger silencing effect on both, with a stronger suppression of the expression of the A-mutant allele than that of the wild-type allele.

Example 1-3

This example shows that silencing abilities of the RNA molecules to the A-mutant allele become stronger and their specificities become much higher by, in addition to matching position 11 of each siRNA with the position of the point mutation in the A-mutant allele, changing the base at the 5'-end of the siRNA's guide strand from guanine to uracil, and changing the base at the 5'-end of the passenger strand from uracil to guanine, replacing the group at 2'-position of the pentose in each of ribonucleotides at positions 6-8 of the guide strand by $OCH_3$.

The wild-type and A-mutant K reporters were used as reporters for examining gene silencing effects. Double-stranded RNAs with the following sequences were chemically synthesized for siRNAs, and K(35)11 Arev was used as a control. In the following sequences, the base pairs in the position corresponding to the position of the point mutation, and the pairs of the modified bases at the 5'-ends of the guide and passenger strands are enclosed in rectangles. The nucleotides in which the group at the 2'-position of the pentose was replaced by $OCH_3$ are hatched.

```
K(35)11ArevOM(2-5):
5'-GGGAGCUGAUGGCGUAGGAAA-3'    (SEQ ID NO. 16)

3'-CACCCUCGACUACCGCAUCCU-5'    (SEQ ID NO. 17)

K(35)11ArevOM(6-8):
5'-GGGAGCUGAUGGCGUAGGAAA-3'    (SEQ ID NO. 18)

3'-CACCCUCGACUACCGCAUCCU-5'    (SEQ ID NO. 19)
```

Figure 3:
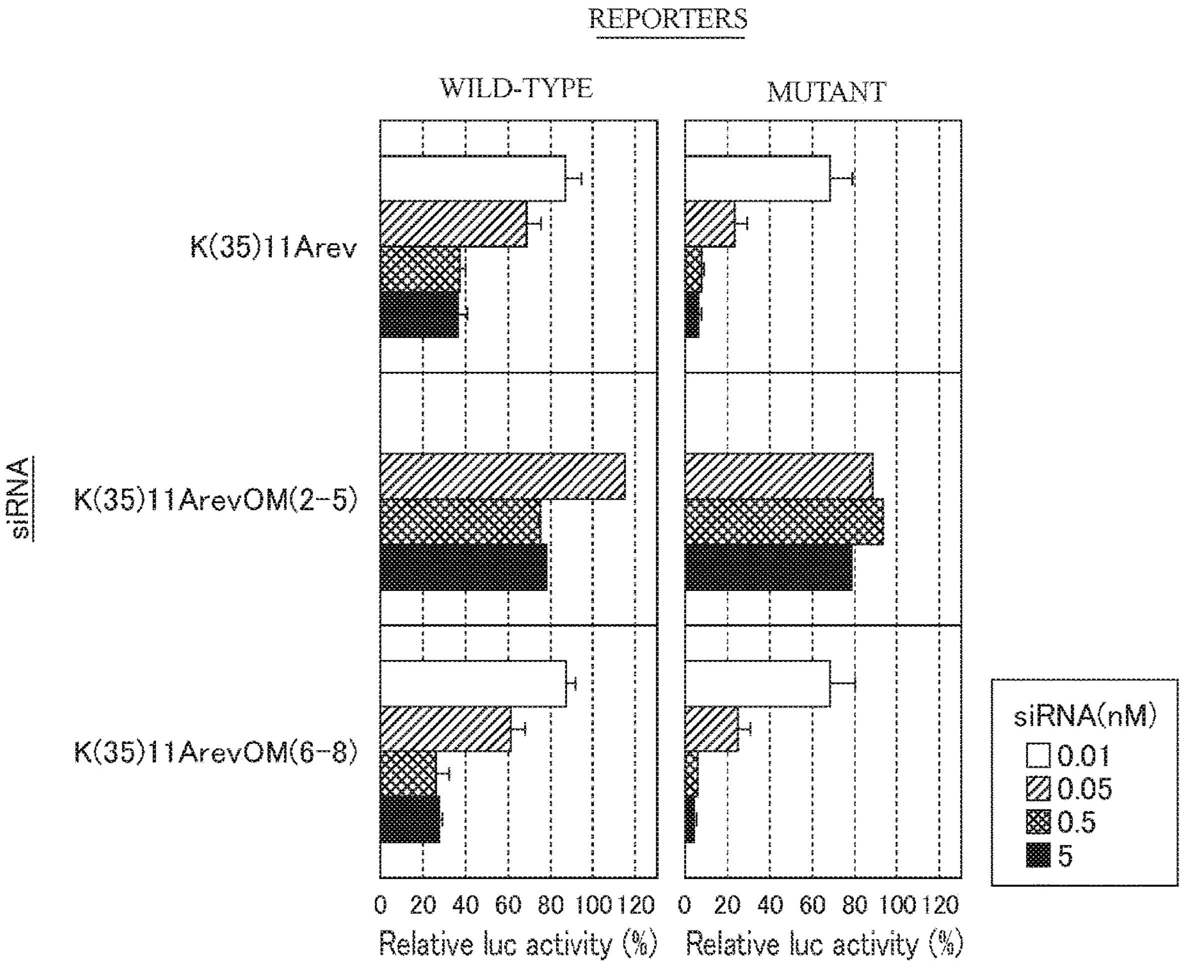
FIG. 3 shows graphs of the results on silencing abilities of siRNAs that target the K-ras gene, in each of which position 11 corresponded to the position of the point mutation, the base at the 5'-end of the guide strand was changed from guanine to uracil, the base at the 5'-end of the passenger strand was changed from uracil to guanine, and the group at the 2'-position of the pentose in each of ribonucleotides at positions 6-8 of the guide strand was replaced by $OCH_3$, in an example of the present invention.

FIG. 3 shows gene silencing effects of the siRNAs.

K(35) 11 Arev strongly suppressed the expression of the A-mutant allele more than that of the wild-type allele, whereas K(35) 11ArevOM(6-8) exerted a stronger silencing effect on both, with a stronger suppression of the expression of the A-mutant allele than that of the wild-type allele. Another control, K(35)11 ArevOM(2-5) in which the group at the 2'-position of the pentose in each of ribonucleotides at positions 2-5 of the guide strand was replaced by $OCH_3$ exerted considerably weak silencing effect on both.

Example 1-4

This example shows that silencing abilities of the RNA molecules to the wild-type allele become weaker and, as a result, their specificities for the A-mutant allele become much higher by, in addition to matching position 11 of each siRNA with the position of the point mutation in the A-mutant allele, changing the base at the 5'-end of the siRNA's guide strand from guanine to uracil, and changing the base at the 5'-end of the passenger strand from uracil to guanine, mismatching the base at position 5 or 6 of the guide strand with that of the A-mutant allele.

The wild-type and A-mutant K reporters were used as reporters for examining gene silencing effects. Double-stranded RNAs with the following sequences with a mismatched base at one of positions 3-7 based on K(35)11Arev were chemically synthesized for siRNAs. K(35)11Arev was used as a control. In the following sequences, the base pairs in the position corresponding to the position of the point mutation, the pairs of the modified bases at the 5'-ends of the guide and passenger strands, and base pairs with the mismatched base are enclosed in rectangles.

```
K(35)11ArevM3:
5'-GGGAGCUGAUGGCGUACGAAA-3'    (SEQ ID NO. 20)

3'-CACCCUCGACUACCGCAGCU-5'    (SEQ ID NO. 21)

K(35)11ArevM4:
5'-GGGAGCUGAUGGCGUUGGAAA-3'    (SEQ ID NO. 22)

3'-CACCCUCGACUACCGCAACCU-5'    (SEQ ID NO. 23)

K(35)11ArevM5:
5'-GGGAGCUGAUGGCGAAGGAAA-3'    (SEQ ID NO. 24)

3'-CACCCUCGACUACCGCUUCCU-5'    (SEQ ID NO. 25)

K(35)11ArevM6:
5'-GGGAGCUGAUGGCCUAGGAAA-3'    (SEQ ID NO. 26)

3'-CACCCUCGACUACCGGAUCCU-5'    (SEQ ID NO. 27)

K(35)11ArevM7:
5'-GGGAGCUGAUGGGGUAGGAAA-3'    (SEQ ID NO. 28)

3'-CACCCUCGACUACCCCAUCCU-5'    (SEQ ID NO. 29)
```

Figure 4:
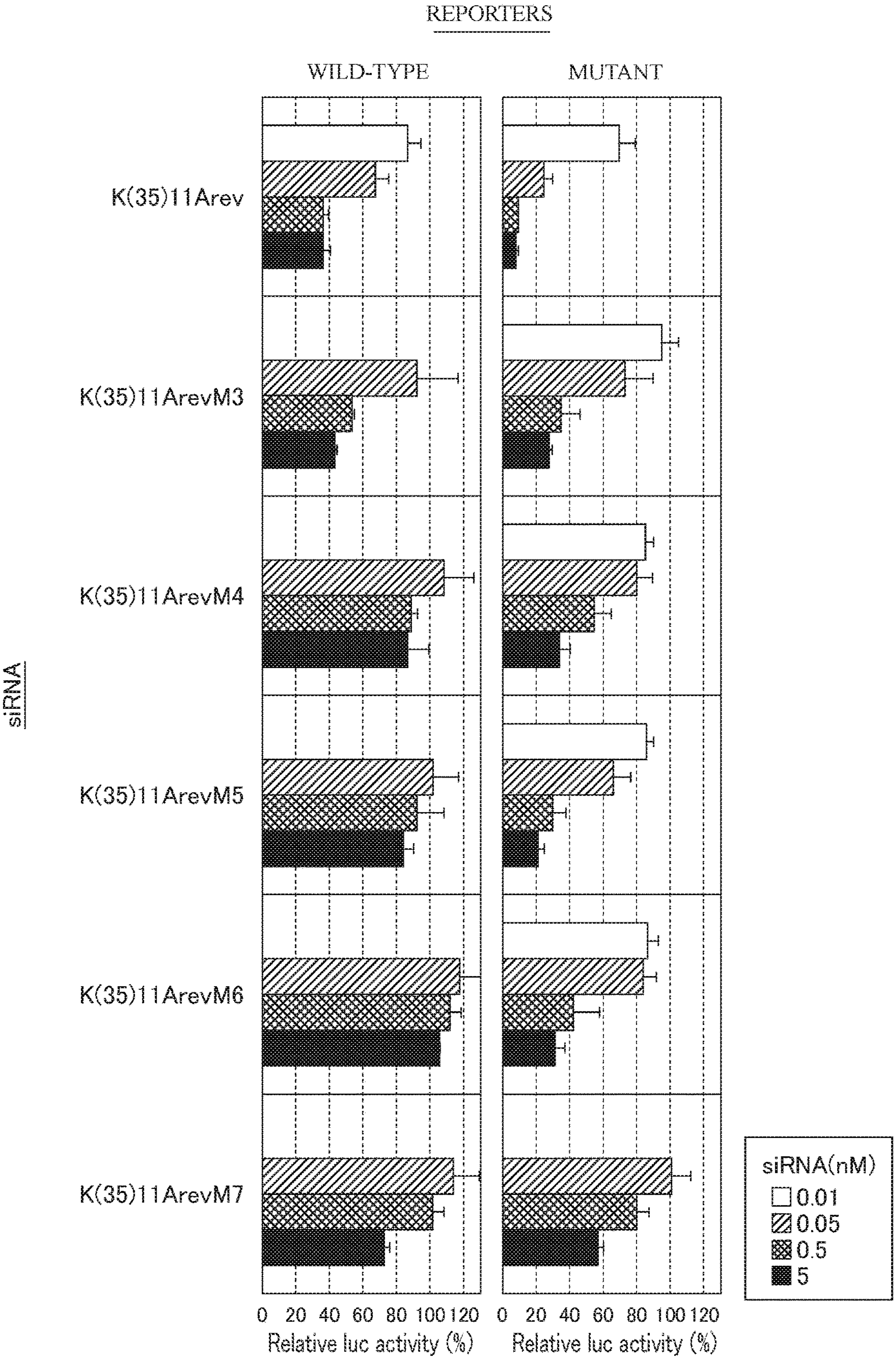
FIG. 4 shows graphs of the results on silencing abilities of siRNAs that target the K-ras gene, in each of which position 11 corresponded to the position of the point mutation, the base at the 5'-end of the guide strand was changed from guanine to uracil, the base at the 5'-end of the passenger strand was changed from uracil to guanine, and the base at either one of positions 3-7 of the guide strand was mismatched with that of the A-mutant allele, in an example of the present invention.

FIG. 4 shows gene silencing effects of the siRNAs.

K(35) 11 Arev strongly suppressed the expression of the A-mutant allele more than that of the wild-type allele, whereas RNA molecules K(35) 11 ArevM5 and K(35)11 ArevM6 exhibited significantly weak silencing abilities to the wild-type allele and, as a result, much higher specificities for the A-mutant allele.

Example 1-5

This example shows that specificities of the RNA molecules for the A-mutant allele become much higher by, in addition to matching position 11 of each siRNA with the position of the point mutation in the A-mutant allele, changing the base at the 5'-end of the siRNA's guide strand from guanine to uracil, and changing the base at the 5'-end of the passenger strand from uracil to guanine, replacing the group at the 2'-position of the pentose in each of ribonucleotides at positions 6-8 of the guide strand by $OCH_3$, and mismatching the base at position 5 or 6 of the guide strand with that of the A-mutant allele.

The wild-type and A-mutant K reporters were used as reporters for examining gene silencing effects. Double-stranded RNAs with the following sequences with a mismatched base at one of positions 3-7 based on K(35)11Arev were chemically synthesized for siRNAs. K(35)11Arev was used as a control. In the following sequences, the base pairs in the position corresponding to the position of the point mutation, the pairs of the modified bases at the 5'-ends of the guide and passenger strands, and base pairs with the mismatched base are enclosed in rectangles. The nucleotides in which the group at the 2'-position of the pentose was replaced by $OCH_3$ are hatched.

K(35)11ArevOM(6-8)M3:
5'-GGGAGCUGAUGGCGUACGAAA-3' (SEQ ID NO. 30)

-continued

3'-CACCCUCGACUACCGCAUGCU-5 (SEQ ID NO. 31)

K(35)11ArevOM(6-8)M4:
5'-GGGAGCUGAUGGCGUUGGAAA-3 (SEQ ID NO. 32)

3'-CACCCUCGACUACCGCAACCU-5 (SEQ ID NO. 33)

K(35)11ArevOM(6-8)M5:
5'-GGGAGCUGAUGGCGAAGGAAA-3 (SEQ ID NO. 34)

3'-CACCCUCGACUACCGCUUCCU-5 (SEQ ID NO. 35)

K(35)11ArevOM(6-8)M6:
5'-GGGAGCUGAUGGCCUAGGAAA-3' (SEQ ID NO. 36)

3'-CACCCUCGACUACCGGAUCCU-5' (SEQ ID NO. 37)

K(35)11ArevOM(6-8)M7:
5'-GGGAGCUGAUGGGGUAGGAAA-3' (SEQ ID NO. 38)

3'-CACCCUCGACUACCCCAUCCU-5' (SEQ ID NO. 39)

Figure 5:
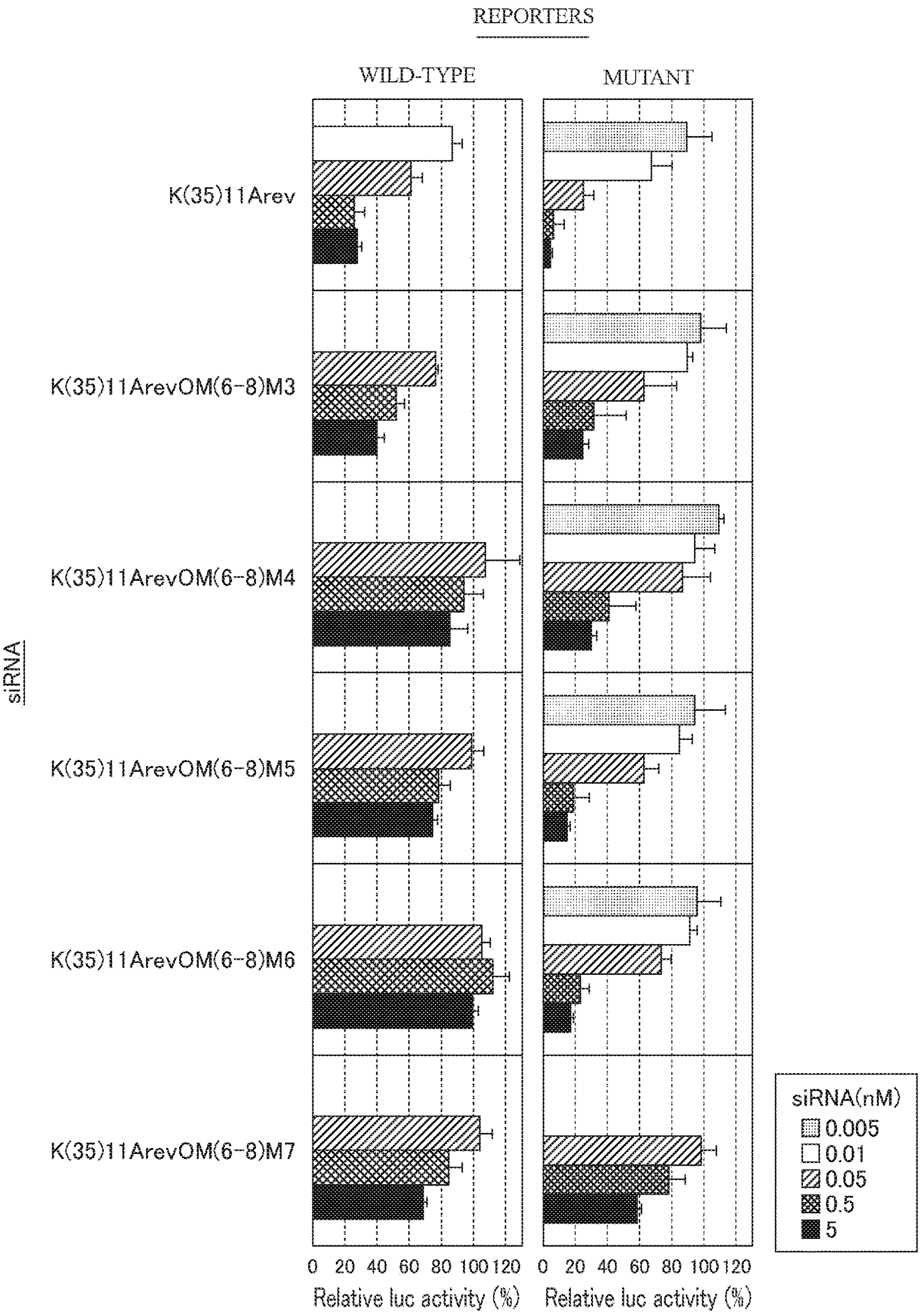
FIG. 5 shows graphs of the results on silencing abilities of siRNAs that target the K-ras gene, in each of which position 11 corresponded to the position of the point mutation, the base at the 5'-end of the guide strand was changed from guanine to uracil, the base at the 5'-end of the passenger strand was changed from uracil to guanine, the group at the 2'-position of the pentose in each of ribonucleotides at positions 6-8 of the guide strand was replaced by $OCH_3$, and the base at either one of positions 3-7 of the guide strand was mismatched with that of the A-mutant allele, in an example of the present invention.

FIG. 5 shows gene silencing effects of the siRNAs.

K(35)11ArevOM(6-8)M5 and K(35)11ArevOM(6-8)M6 exhibited very weak silencing abilities to the wild-type allele and, as a result, their specificities for the A-mutant allele became much higher.

Example 1-6

This example shows that siRNAs specific for the A-mutant allele exhibit weak silencing abilities not only to the wild-type allele, but also to the T-mutant allele of the K-ras gene (c. 35G>T) and the C-mutant allele of the K-ras gene (c. 35 G>C).

K-ras reporters indicated below, i.e., the wild-type K reporter, the A-mutant K reporter, a T-mutant reporter for the K-ras gene (c. 35G>T) (hereinafter, referred to as the "T-mutant K reporter"), and a C-mutant reporter for the K-ras gene (c. 35 G>C) (hereinafter, referred to as the "C-mutant K reporter"), were used as reporters for examining gene silencing effects. K(35)11ArevOM(6-8)M5 and K(35)11 ArevOM(6-8)M6 were used as siRNAs, and K(35) 11Arev was used as a control. In the following sequences, the base pairs in the position corresponding to the position of the point mutation are enclosed in rectangles.

T-mutant K reporter:
5'-TGGTAGTTGGAGCTGTTGGCGTAGGCAAGAGTG-3' (SEQ ID NO. 40)

3'-ACCATCAACCTCGACAACCGCATCCGTTCTCAC-5' (SEQ ID NO. 41)

C-mutant K reporter:
5'-TGGTAGTTGGAGCTGCTGGCGTAGGCAAGAGTG-3' (SEQ ID NO. 42)

3'-ACCATCAACCTCGACGACCGCATCCGTTCTCAC-5' (SEQ ID NO. 43)

Figure 6:
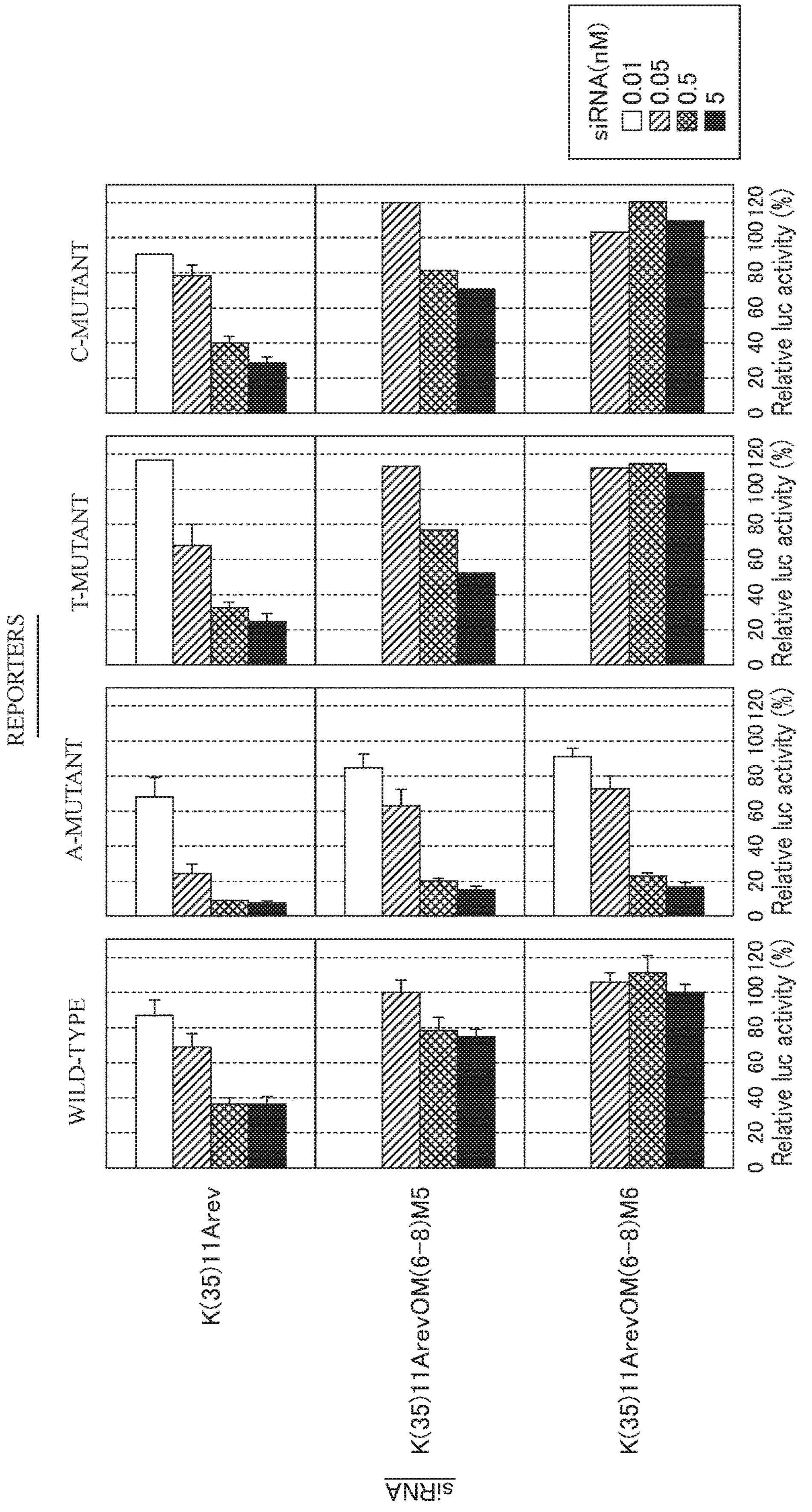
FIG. 6 shows graphs of the results on silencing abilities of siRNAs specific for the A-mutant allele of the K-ras gene, to the wild-type allele, the T-mutant allele of the K-ras gene (c. 35G>T), and the C-mutant allele of the K-ras gene (c. 35 G>C), in an example of the present invention.

FIG. 6 shows gene silencing effects on the reporters.

All siRNAs had the strongest silencing effect on the A-mutant K reporter; especially K(35) 11 ArevOM(6-8)M5 and K(35) 11ArevOM(6-8)M6 had weak silencing effects on the T-mutant and C-mutant K reporters.

Example 1-7

This example shows that siRNAs specific for the T-mutant allele exhibit weak silencing abilities to the A-mutant and C-mutant alleles in addition to the wild-type allele.

K-ras reporters, i.e., the wild-type, A-mutant, T-mutant, and C-mutant K reporters, were used as reporters for examining gene silencing effects. K(35)11TrevOM(6-8)M5 and K(35)11TrevOM(6-8)M6 were used as siRNAs, and K(35) 11 Trev was used as a control. In the following sequences, the base pairs in the position corresponding to the position of the point mutation, the pairs of the modified bases at the 5'-ends of the guide and passenger strands, and the base pairs with the mismatched base are enclosed in rectangles. The nucleotides in which the group at 2'-position of the pentose was replaced by $OCH_3$ are hatched.

K(35)11Trev:
5'-GGGAGCUGUUGGCGUAGGAAA-3' (SEQ ID NO. 44)

3'-CACCCUCGACAACCGCAUCCU-5' (SEQ ID NO. 45)

K(35)11TrevOM(6-8)M5:
5'-GGGAGCUGUUGGCGAAGGAAA-3' (SEQ ID NO. 46)

3'-CACCCUCGACAACCGCUUCCU-5' (SEQ ID NO. 47)

-continued

K(35)11TrevOM(6-8)M6:

5′-GGGAGCUGUUGGCCUAGGAAA-3′ (SEQ ID NO. 48)

3′-CACCCUCGACAACCGGAUCCU-5′ (SEQ ID NO. 49)

Figure 7:
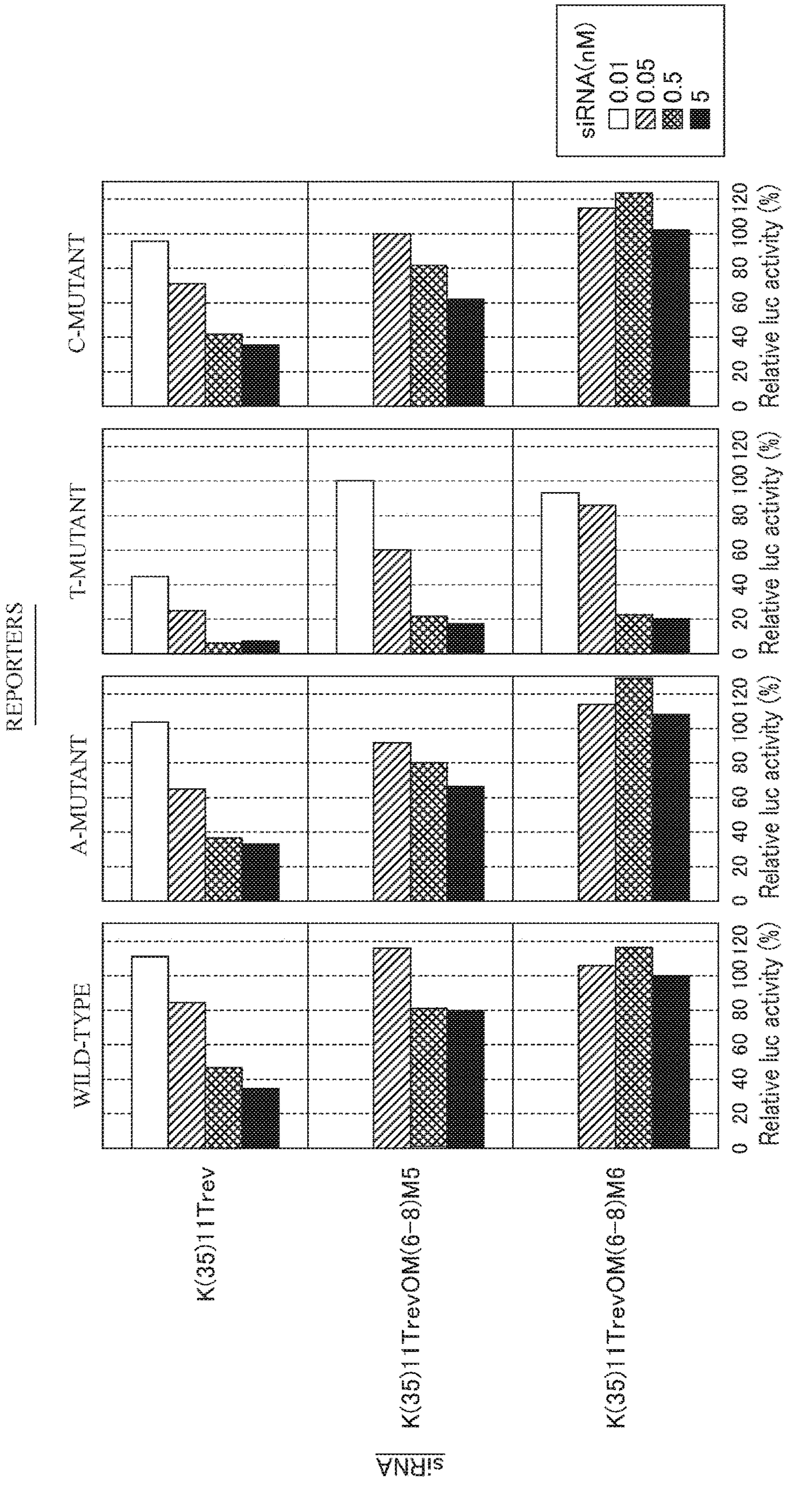
FIG. 7 shows graphs of the results on silencing abilities of siRNAs specific for the T-mutant allele of the K-ras gene, to the wild-type allele, and the A- and C-mutant alleles of the K-ras gene, in an example of the present invention.

FIG. 7 shows gene silencing effects on the reporters.

All siRNAs had the strongest silencing effect on the T-mutant K reporter; especially K(35) 11TrevOM(6-8)M5 and K(35)11TrevOM(6-8)M6 had weak silencing effects on the T-mutant and C-mutant K reporters.

Example 1-8

This example shows that siRNAs specific for the C-mutant allele exhibit weak silencing abilities to the A-mutant and T-mutant alleles in addition to the wild-type allele.

K-ras reporters, i.e., the wild-type, A-mutant, T-mutant, and C-mutant K reporters were used as reporters for examining gene silencing effects. K(35)11CrevOM(6-8)M5 and K(35)11CrevOM(6-8)M6 were used as siRNAs, and K(35) 11 Crev was used as a control. In the following sequences, the base pairs in the position corresponding to the position of the point mutation, the pairs of the modified bases at the 5'-ends of the guide and passenger strands, and the base pairs with the mismatched base are enclosed in rectangles. The nucleotides in which the group at the 2'-position of the pentose was replaced by $OCH_3$ are hatched.

K(35)11Crev:

5′-GGGAGCUGCUGGCGUAGGAAA-3′ (SEQ ID NO. 50)

3′-CACCCUCGACGACCGCAUCCU-5′ (SEQ ID NO. 51)

K(35)11CrevOM(6-8)M5:

5′-GGGAGCUGCUGGCGAAGGAAA-3′ (SEQ ID NO. 52)

3′-CACCCUCGACGACCGCUUCCU-5′ (SEQ ID NO. 53)

-continued

K(35)11CrevOM(6-8)M6:

5′-GGGAGCUGCUGGCCUAGGAAA-3′ (SEQ ID NO. 54)

3′-CACCCUCGACGACCGGAUCCU-5′ (SEQ ID NO. 55)

Figure 8:
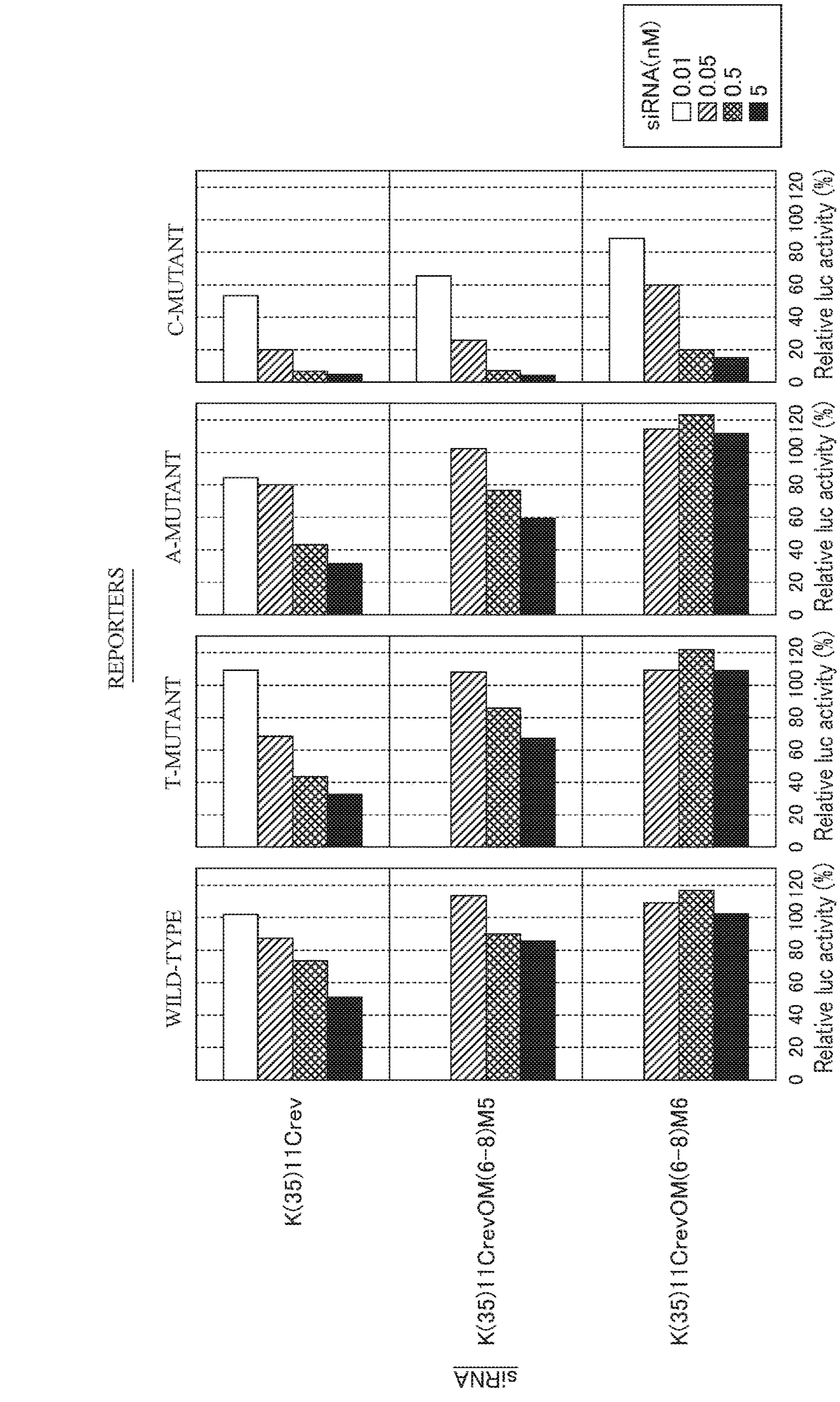
FIG. 8 shows graphs of the results on silencing abilities of siRNAs specific for the C-mutant allele of the K-ras gene, to the wild-type allele, and the A- and T-mutant alleles of the K-ras gene, in an example of the present invention.

FIG. 8 shows gene silencing effects on the reporters.

All siRNAs had the strongest silencing effect on the C-mutant K reporter; especially K(35) 11CrevOM(6-8) M5 and K(35)11CrevOM(6-8)M6 had weak silencing effect on the A-mutant and T-mutant K reporters.

Example 2

In this example, the N-ras gene was chosen as a target gene to be silenced.

Example 2-1

This example, targeting the point mutation in nt 35 of N-ras cDNA, shows that siRNAs suppress the expression of the A-mutant N35 allele more specifically than that of the wild-type allele of the N-ras (wt) gene (hereinafter, referred to as the "wild-type N allele") by matching position 11 of each siRNA with the position of the point mutation in the A-mutant allele of the N-ras gene (c. 35G>A) (hereinafter, referred to as the "A-mutant N35 allele"), changing the base at the 5'-end of the guide strand of the siRNA from cytosine to uracil, changing the base at the 5'-end of the passenger strand from adenine to guanine, replacing the group at the 2'-position of the pentose in each of ribonucleotides at positions 6-8 of the guide strand by $OCH_3$, and mismatching the base at position 5 of the guide strand with that of the A-mutant N35 allele.

First, as reporters for examining gene silencing effects, DNAs with the same nucleotide sequences as the wild-type N allele and the A-mutant N35 allele were inserted into the 3'-UTR of the luciferase gene in an expression vector (psiCHECK) to construct wild-type N35 and A-mutant N reporters, respectively. The sequences of the segments chemically synthesized and incorporated into the vectors are indicated below. In the following sequences, the base pairs in the position corresponding to the position of the point mutation are enclosed in rectangles.

Wild-type N35 reporter:

5′-ACTGGTGGTGGTTGGAGCAGGTGGTGTTGGGAAAAGCGCA-3′ (SEQ ID NO. 56)

3′-TGACCACCACCAACCTCGACCACCACAACCCTTTTCGCGT-5′ (SEQ ID NO. 57)

A-mutant N35 reporter:

5′-ACTGGTGGTGGTTGGAGCAGATGGTGTTGGGAAAAGCGCA-3′ (SEQ ID NO. 58)

3′-TGACCACCACCAACCTCGACTACCACAACCCTTTTCGCGT-5′ (SEQ ID NO. 59)

Double-stranded RNAs with the following sequences were chemically synthesized for siRNAs. N(35)11G has a sequence complementary to that of the wild-type N allele. N(35)11A is an siRNA in which position 11 corresponded to the position of the point mutation in the A-mutant N35 allele. N(35) 11 ArevOM(6-8)M5 is an siRNA in which position 11 corresponded to the position of the point mutation in the A-mutant N35 allele, the base at the 5'-end of the guide strand was changed from cytosine to uracil, the base at the 5'-end of the passenger strand was changed from uracil to cytosine, the group at the 2'-position of the pentose in each of ribonucleotides at positions 6-8 of the guide strand was replaced by $OCH_3$, and the base at position 5 of the siRNA's guide strand was mismatched with that of the A-mutant N35 allele. In the following sequences, the base pairs in the position corresponding to the position of the point mutation, the pairs of the modified bases at the 5'-ends of the guide and passenger strands, and the base pairs with the mismatched base are enclosed in rectangles. The nucleotides in which the group at the 2'-position of the pentose was replaced by $OCH_3$ are hatched.

N(35)11G:

5'-UGGAGCAGGUGGUGUUGGGAA-3' (SEQ ID NO. 60)

3'-CAACCUCGUCCACCACAACCC-5' (SEQ ID NO. 61)

N(35)11A:

5'-UGGAGCAGAUGGUGUUGGGAA-3' (SEQ ID NO. 62)

3'-CAACCUCGUCUACCACAACCC-5' (SEQ ID NO. 63)

N(35)11ArevOM(6-8)M5:

5'-CGGAGCAGAUGGUGAUGGAAA-3' (SEQ ID NO. 64)

3'-CAGCCUCGUCUACCACUACCU-5' (SEQ ID NO. 65)

Figure 9:
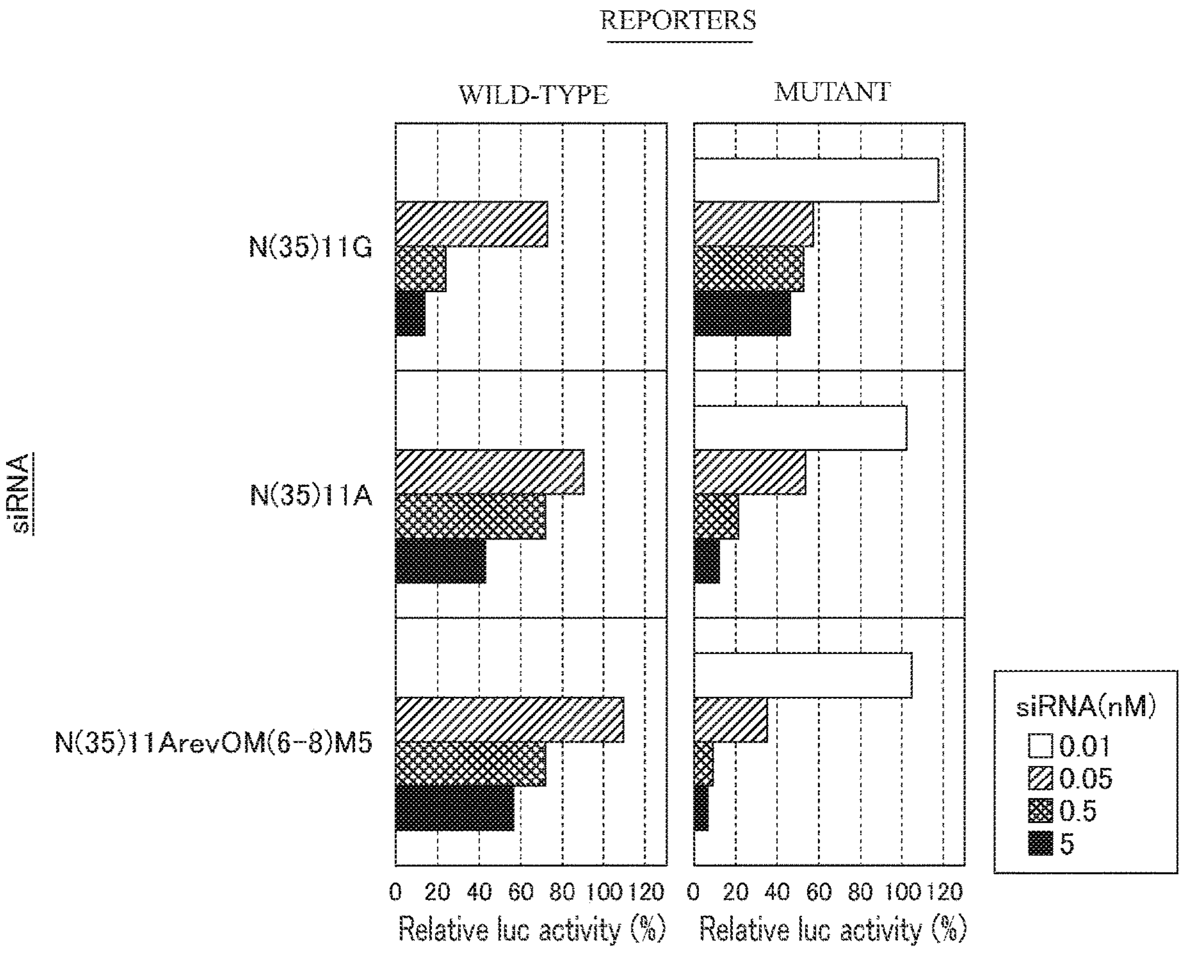
FIG. 9 shows graphs of the results on silencing abilities of siRNAs that target the point mutation in nt 35 of cDNA of the N-ras gene, in which position 11 corresponded to the position of the point mutation in the A-mutant allele of the N-ras gene (c. 35G>A) (hereinafter, referred to as the "A-mutant N35 allele"), the base at the 5'-end of the guide strand was changed from cytosine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 5 of the guide strand was mismatched with that of the A-mutant N35 allele, in an example of the present invention.

FIG. 9 shows gene silencing effects of the siRNAs.

N(35) 11G effectively suppressed the expression of the wild-type N allele more than that of the A-mutant N35 allele. In contrast, N(35)11A effectively suppressed the expression of the A-mutant N35 allele more than that of the wild-type N allele. N(35)11ArevOM(6-8)M5 had very weak silencing abilities to the wild-type allele and strong silencing abilities to the A-mutant N35 allele; as a result, specificity for the A-mutant N35 allele was increased.

Example 2-2

This example, targeting the point mutation in nt 182 of N-ras cDNA shows that siRNAs suppress the expression of the G-mutant N182 allele more specifically than that of the wild-type allele of the N-ras (wt) gene (hereinafter, referred to as the "wild-type N allele") by matching position 11 of each siRNA with the position of the point mutation in the G-mutant allele of the N-ras gene (c. 182A>G) (hereinafter, referred to as the "G-mutant N182 allele"), changing the base at the 5'-end of the guide strand of the siRNA from guanine to uracil, changing the base at the 5'-end of the passenger strand from adenine to guanine, replacing the group at the 2'-position of the pentose in each of ribonucleotides at positions 6-8 of the guide strand by $OCH_3$, and mismatching the base at position 5 of the guide strand with that of the G-mutant N182 allele.

First, as reporters for examining gene silencing effects, DNAs with the same nucleotide sequence as the G-mutant N182 allele were inserted into the 3'-UTR of the luciferase gene in an expression vector (psiCHECK) to construct a G-mutant N182 reporter. The sequences of the segments chemically synthesized and incorporated into the vector are indicated below.

Wild-type N182 reporter:

5'-CATACTGGATACAGCTGGACAAGAAGAGTACAGTGCCA-3' (SEQ ID NO. 66)

3'-GTATGACCTATGTCGACCTGTTCTTCTCATGTCACGGT-5' (SEQ ID NO. 67)

G-mutant N182 reporter:

5'-CATACTGGATACAGCTGGACGAGAAGAGTACAGTGCCA-3' (SEQ ID NO. 68)

3'-GTATGACCTATGTCGACCTGCTCTTCTCATGTCACGGT-5' (SEQ ID NO. 69)

Double-stranded RNAs with the following sequences were chemically synthesized for siRNAs. N(182)11A has a sequence complementary to that of the wild-type N allele. N(182)11G is an siRNA in which position 11 corresponded to the position of the point mutation in the G-mutant N182 allele. N(182)11GrevOM(6-8)M5 is an siRNA in which position 11 corresponded to the position of the point mutation in the G-mutant N182 allele, the base at the 5'-end of the guide strand was changed from guanine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 5 of the siRNA's guide strand was mismatched with that of the G-mutant N182 allele. In the following sequences, the base pairs in the position corresponding to the position of the point mutation, the pairs of the modified bases at the 5'-ends of the guide and passenger strands, and the base pairs with the mismatched base are enclosed in rectangles. The nucleotides in which the group at the 2'-position of the pentose was replaced by $OCH_3$ are hatched.

N(182)11A:

5'-AGCUGGACAAGAAGAGUACAG-3' (SEQ ID NO. 70)

3'-UGUCGACCUGUUCUUCUCAUG-5' (SEQ ID NO. 71)

-continued

N(182)11G:

5'-AGCUGGACGAGAAGAGUACAG-3' (SEQ ID NO. 72)

3'-UGUCGACCUGCUCUUCUCAUG-5' (SEQ ID NO. 73)

N(182)11GrevOM(6-8)M5:

5'-GGCUGGACGAGAAGUGUAAAG-3' (SEQ ID NO. 74)

3'-UGCCGACCUGCUCUUCACAUU-5' (SEQ ID NO. 75)

Figure 10:
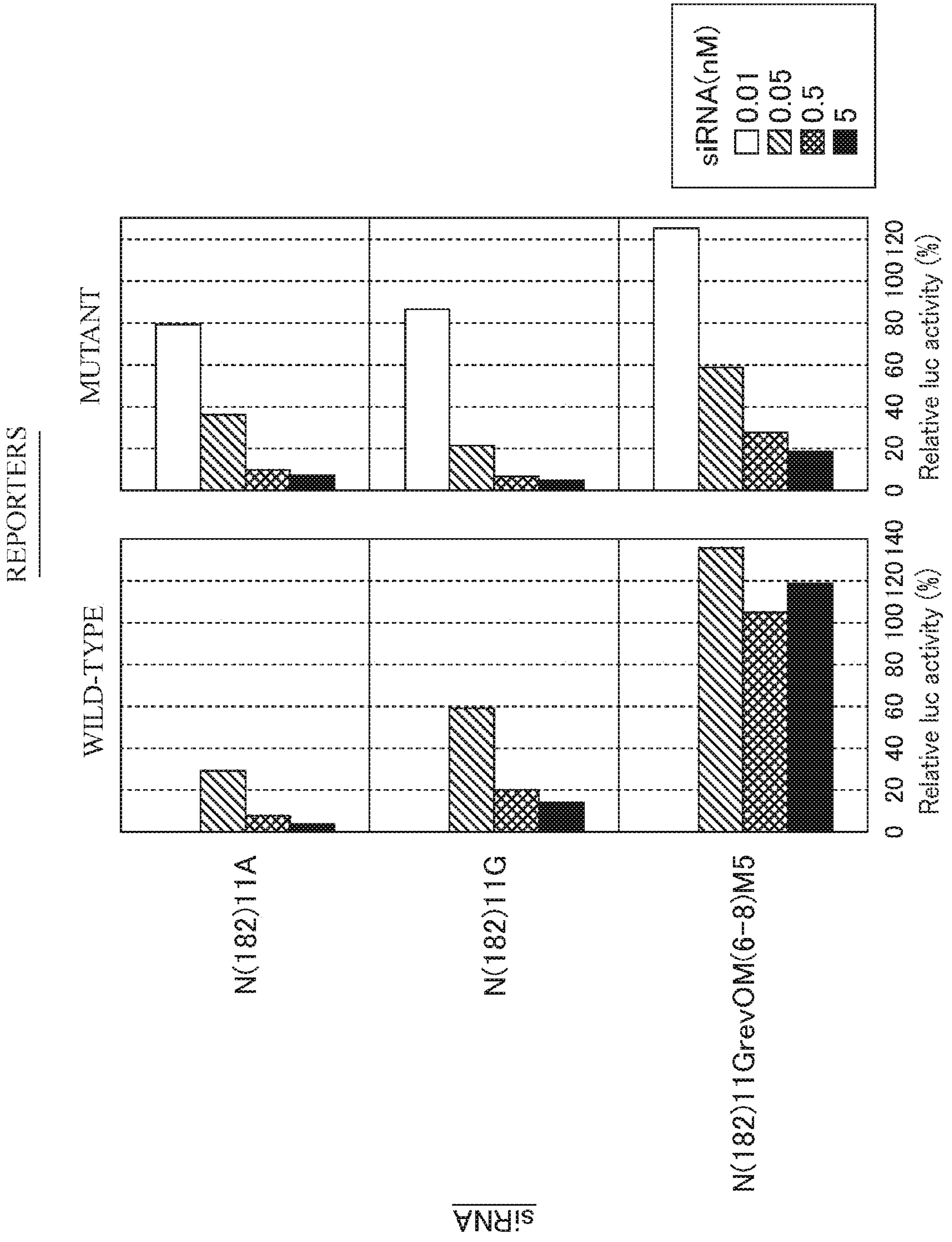
FIG. 10 shows graphs of the results on silencing abilities of siRNAs that target the point mutation in nt 182 of cDNA of the N-ras gene, in which position 11 corresponded to the position of the point mutation in the G-mutant allele of the N-ras gene (c. 182A>G) (hereinafter, referred to as the "G-mutant N182 allele"), the base at the 5'-end of the guide strand was changed from guanine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 5 of the guide strand was mismatched with that of the G-mutant N182 allele, in an example of the present invention.
Figure 11:
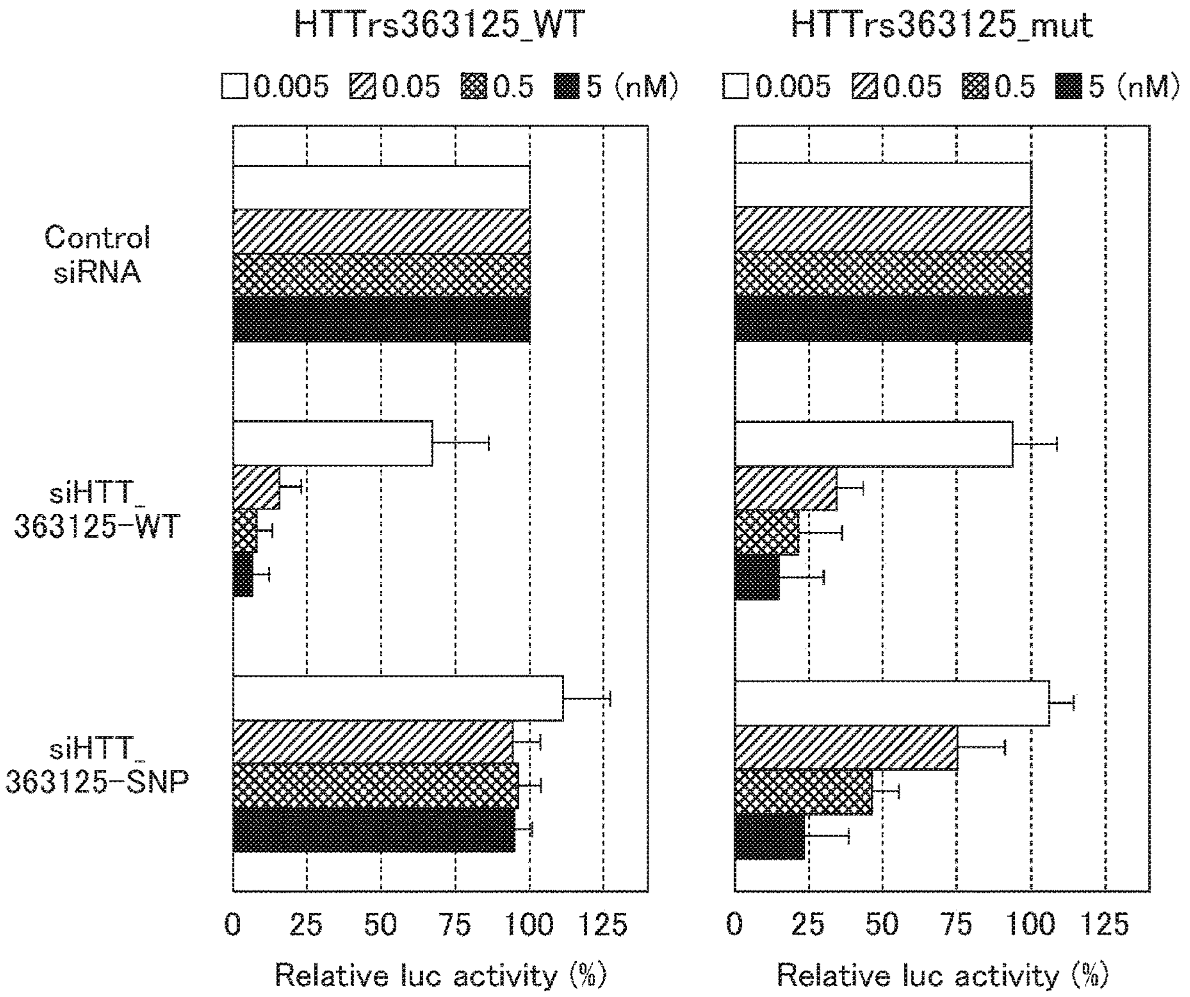
FIG. 11 shows graphs of the results on silencing abilities of a first siRNA that targets the HTT gene, in which position 11 corresponded to the position of the point mutation, the base at the 5'-end of the passenger strand was changed from cytosine to guanine, the group at the 2'-position of the pentose in each of ribonucleotides at positions 6-8 of the guide strand was replaced by $OCH_3$, and the base at position 6 of the guide strand was mismatched by changing it from uracil to adenine, in an example of the present invention.
Figure 12:
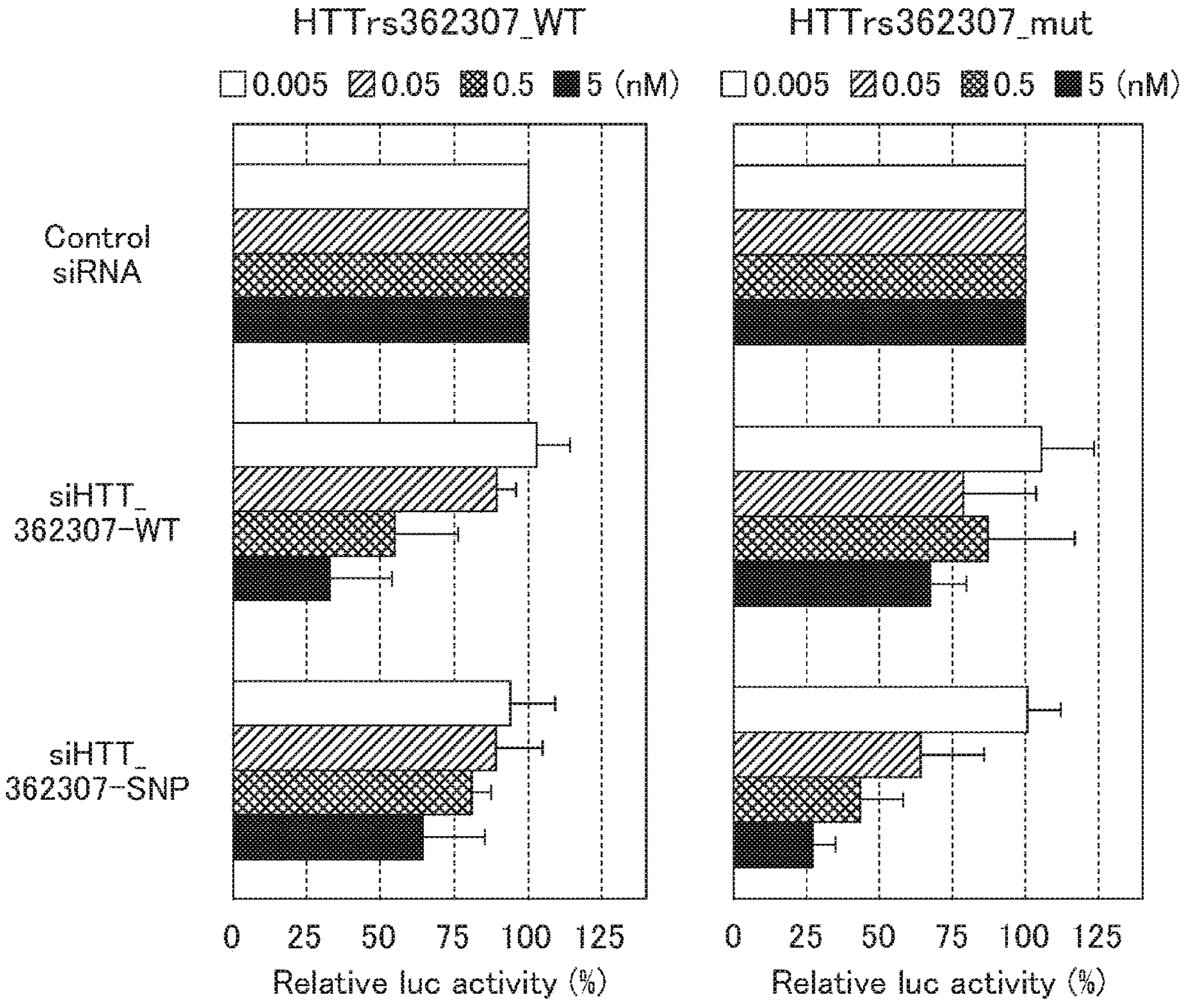
FIG. 12 shows graphs of the results on silencing abilities of a second siRNA that targets the HTT gene, in which position 11 corresponded to the position of the point mutation, the base at the 5'-end of the guide strand was changed from guanine to uracil, the group at the 2'-position of the pentose in each of ribonucleotides at positions 6-8 of the guide strand was replaced by $OCH_3$, and the base at position 6 of the guide strand was mismatched by changing it from adenine to uracil, in an example of the present invention.
Figure 13:
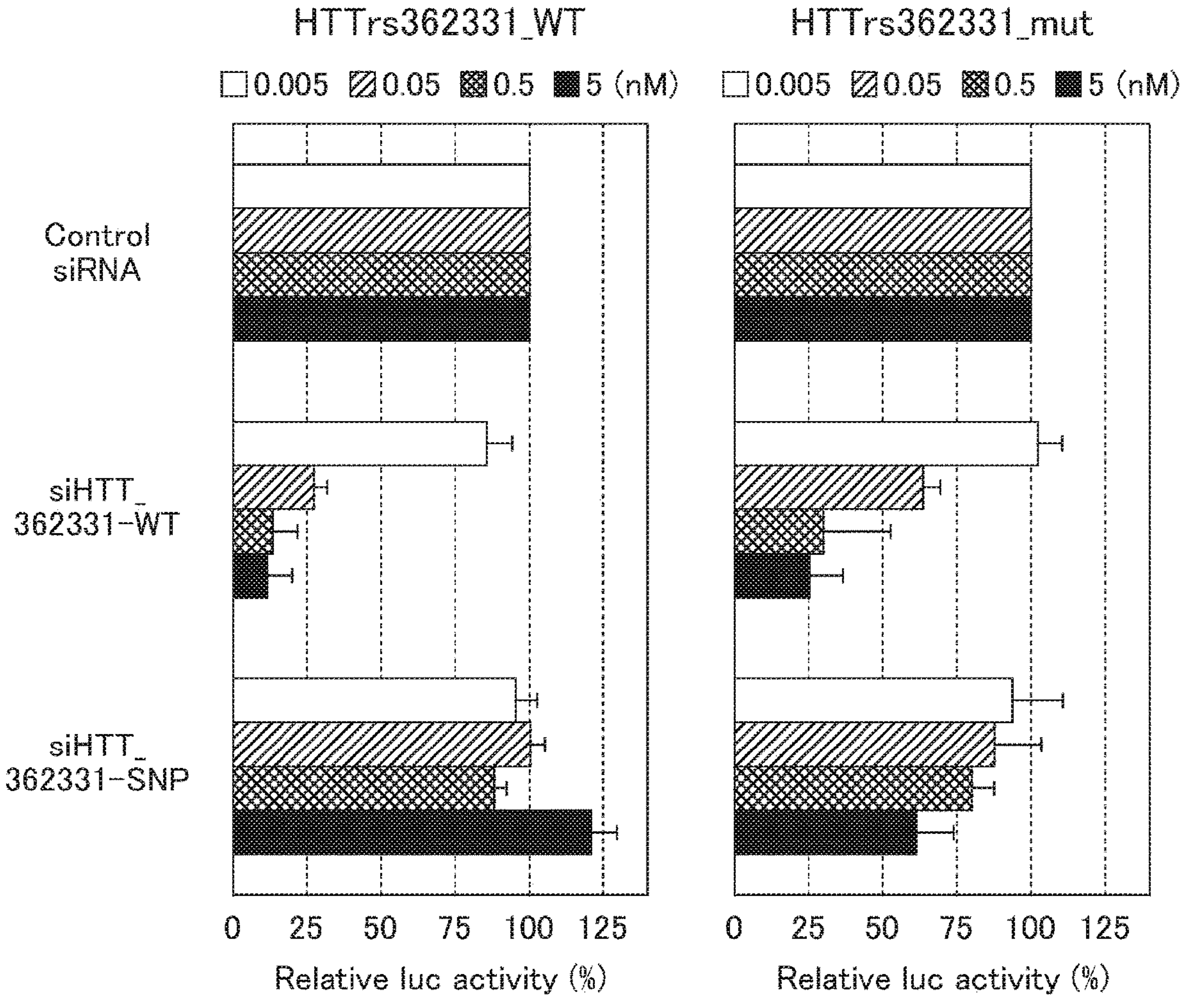
FIG. 13 shows graphs of the results on silencing abilities of a third siRNA that targets the HTT gene, in which position 11 corresponded to the position of the point mutation, the base at the 5'-end of the passenger strand was changed from cytosine to guanine, the group at the 2'-position of the pentose in each of ribonucleotides at positions 6-8 of the guide strand was replaced by $OCH_3$, and the base at position 6 of the guide strand was mismatched by changing it from adenine to uracil, in an example of the present invention.
Figure 14:
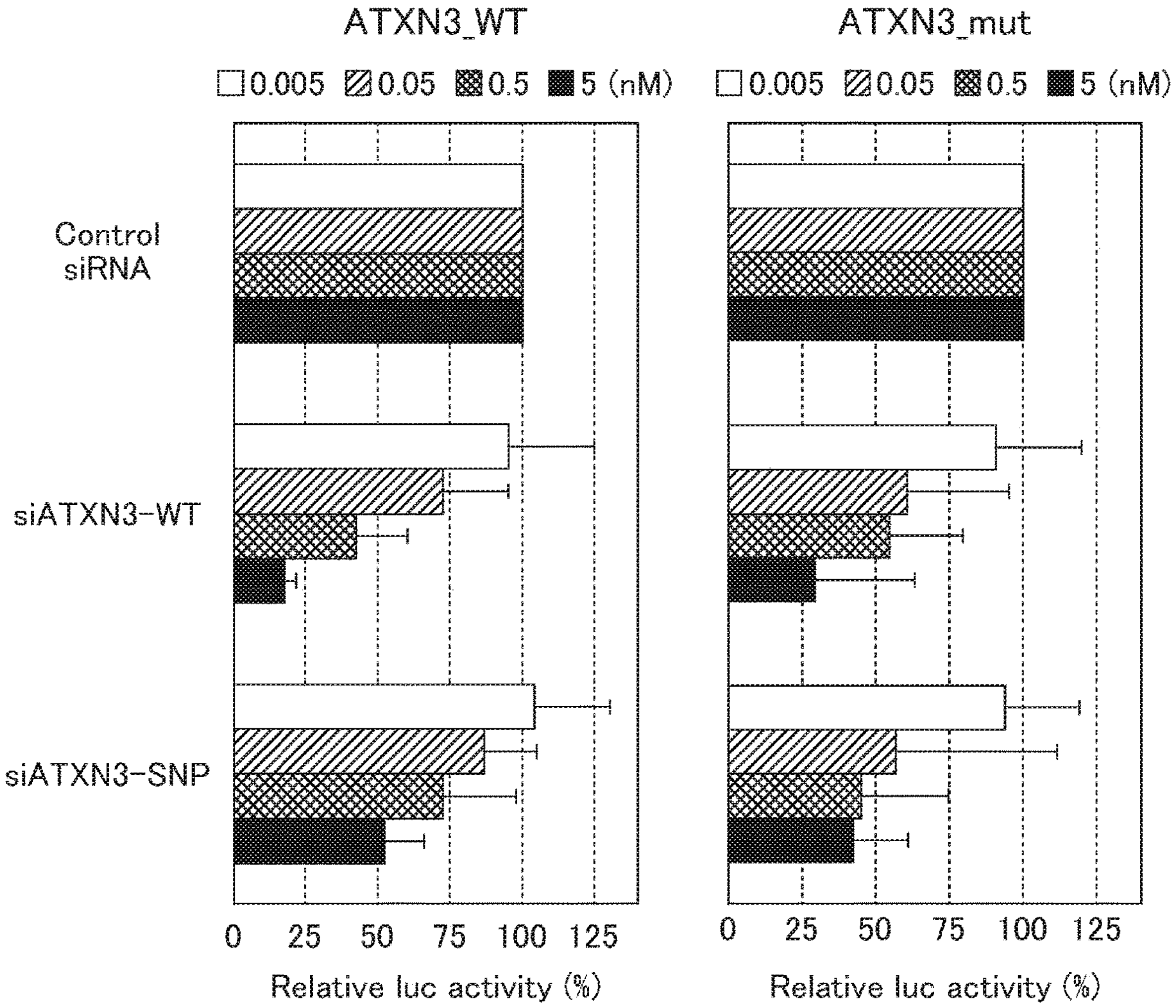
FIG. 14 shows graphs of the results on silencing abilities of siRNAs that target the ATXN 3 gene, in each of which position 11 corresponded to the position of the point mutation, the base at the 5'-end of the guide strand was changed from guanine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 6 of the guide strand was mismatched by changing it from guanine to cytosine, in an example of the present invention.
Figure 15:
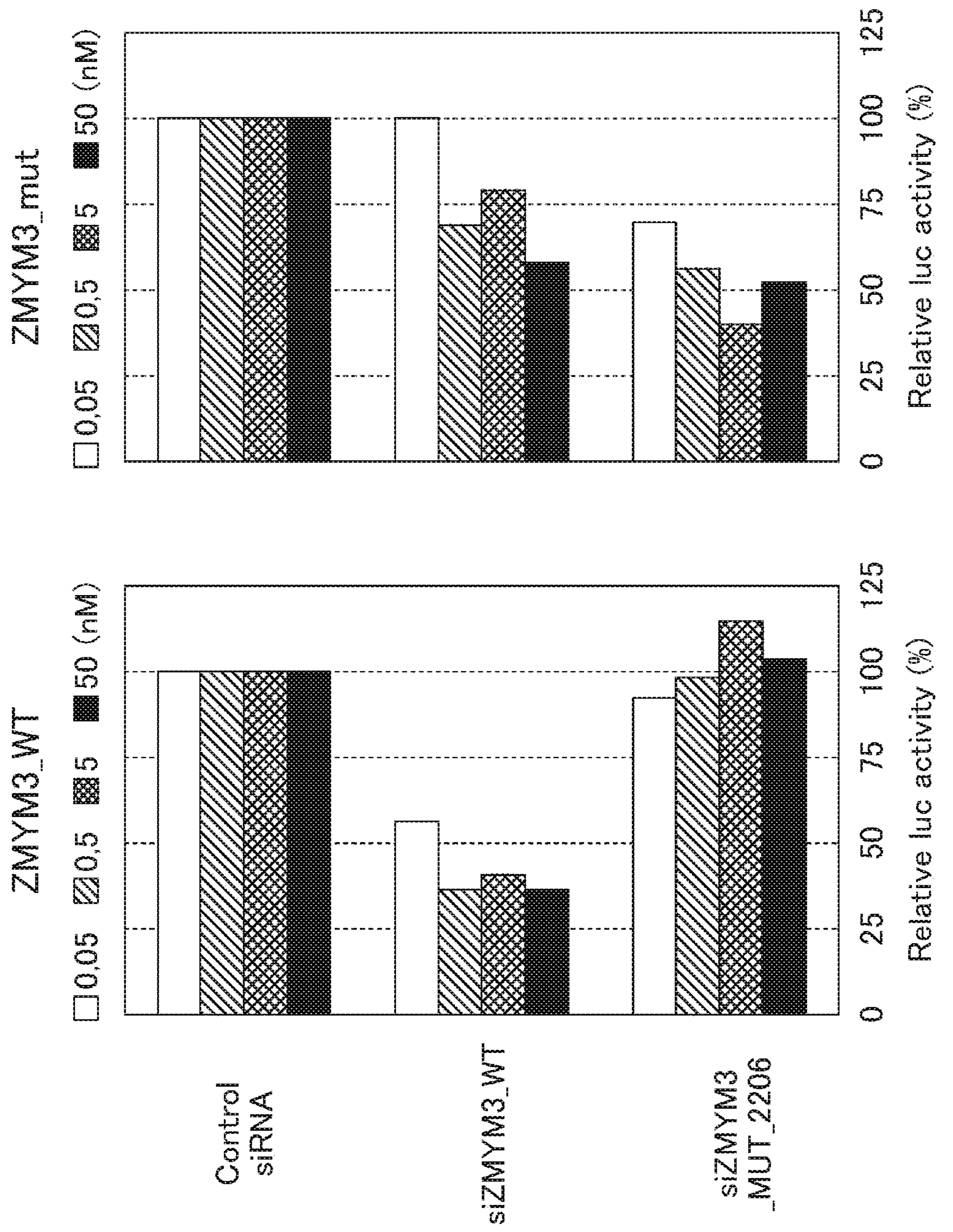
FIG. 15 shows graphs of the results on silencing abilities of siRNAs that target the ZMYM3 gene, in each of which position 11 corresponded to the position of the point mutation, the base at the 5'-end of the guide strand was changed from adenine to uracil, the base at the 5'-end of the passenger strand was changed from uracil to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 16:
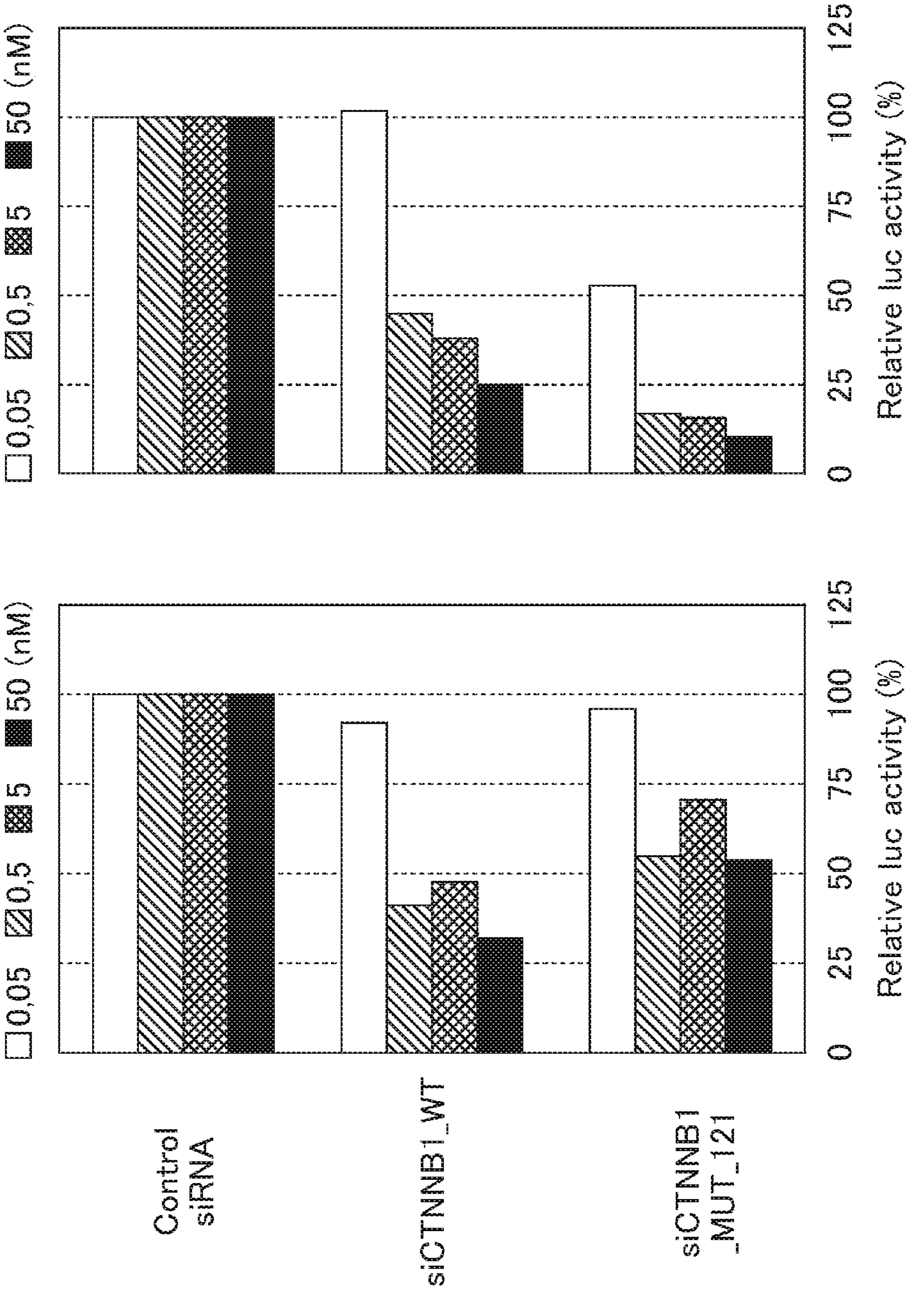
FIG. 16 shows graphs of the results on silencing abilities of siRNAs that target the CTNNB1 gene, in each of which position 11 corresponded to the position of the point mutation, the base at the 5'-end of the guide strand was changed from guanine to uracil, the group at the 2'-position of the pentose in each of ribonucleotides at positions 6-8 of the guide strand was replaced by $OCH_3$, and the base at position 6 of the guide strand was mismatched by changing it from uracil to adenine, in an example of the present invention.
Figure 17:
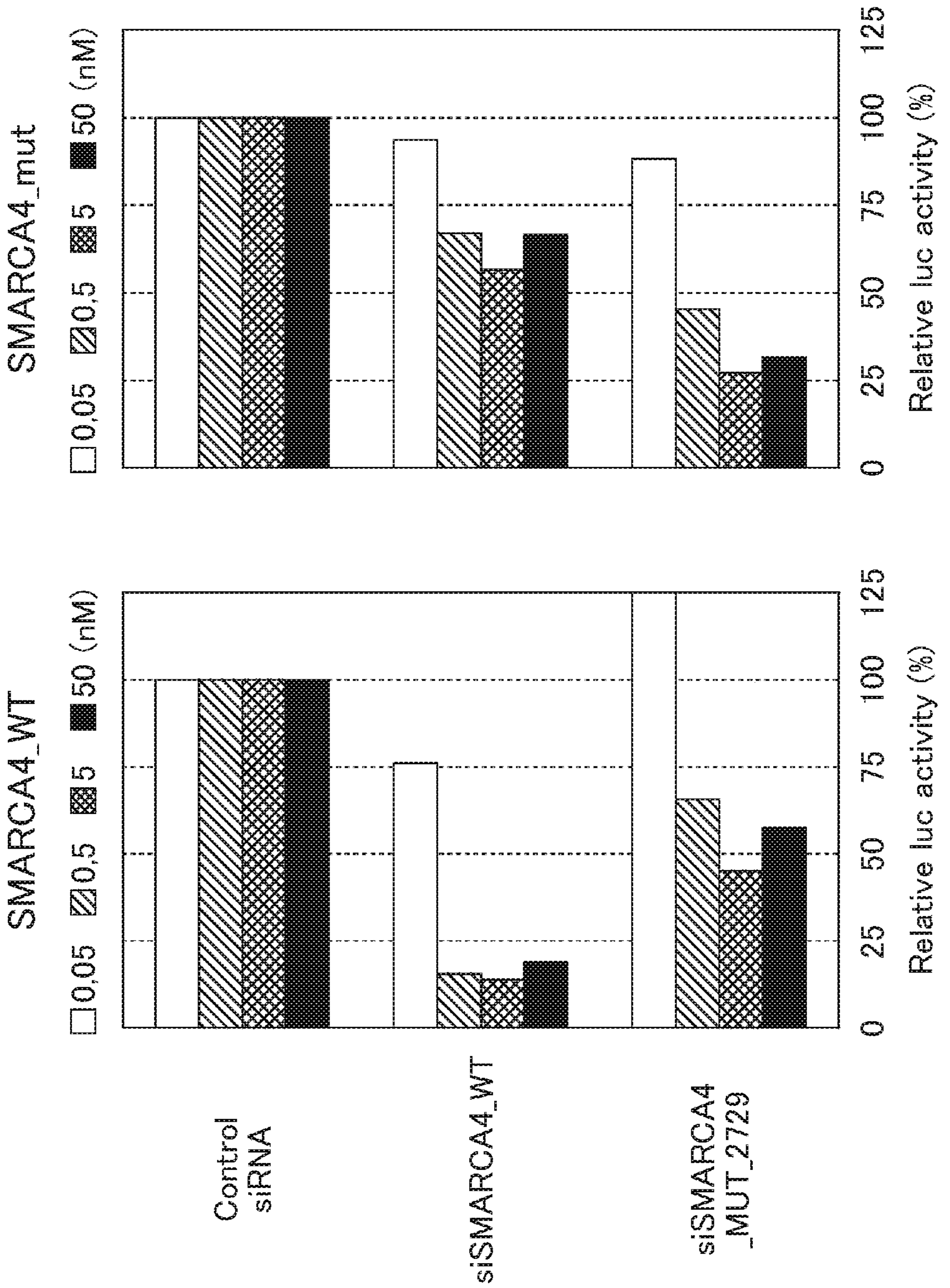
FIG. 17 shows graphs of the results on silencing abilities of siRNAs that target the SMARCA4 gene, in each of which position 11 corresponded to the position of the point mutation, the base at the 5'-end of the guide strand was changed from cytosine to uracil, the group at the 2'-position of the pentose in each of ribonucleotides at positions 6-8 of the guide strand was replaced by $OCH_3$, and the base at position 6 of the guide strand was mismatched by changing it from uracil to adenine, in an example of the present invention.
Figure 18:
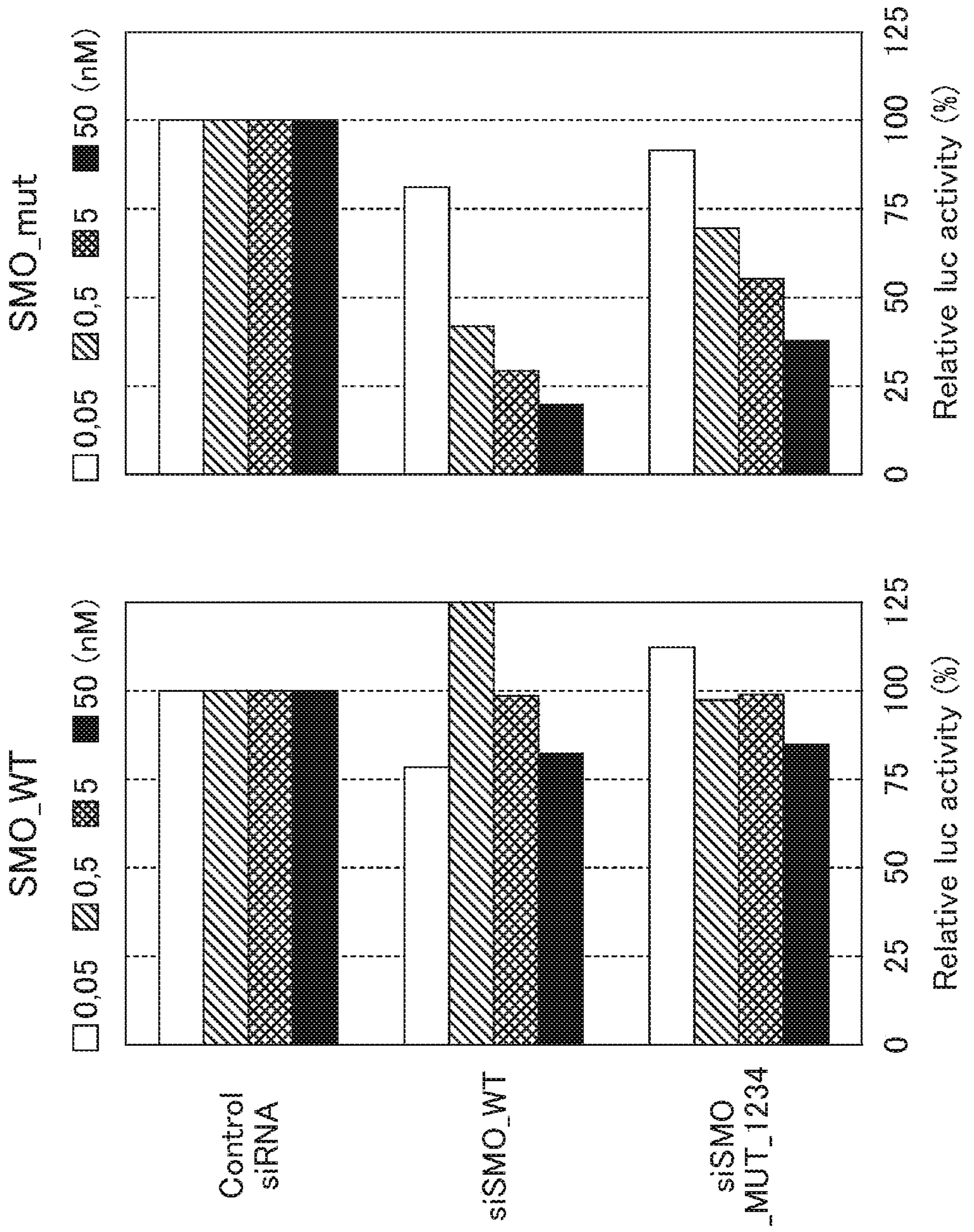
FIG. 18 shows graphs of the results on silencing abilities of siRNAs that target the SMO gene, in each of which position 11 corresponded to the position of the point mutation, the base at the 5'-end of the guide strand was changed from cytosine to guanine, the group at the 2'-position of the pentose in each of ribonucleotides at positions 6-8 of the guide strand was replaced by $OCH_3$, and the base at position 6 of the guide strand was mismatched by changing it from guanine to cytosine, in an example of the present invention.
Figure 19:
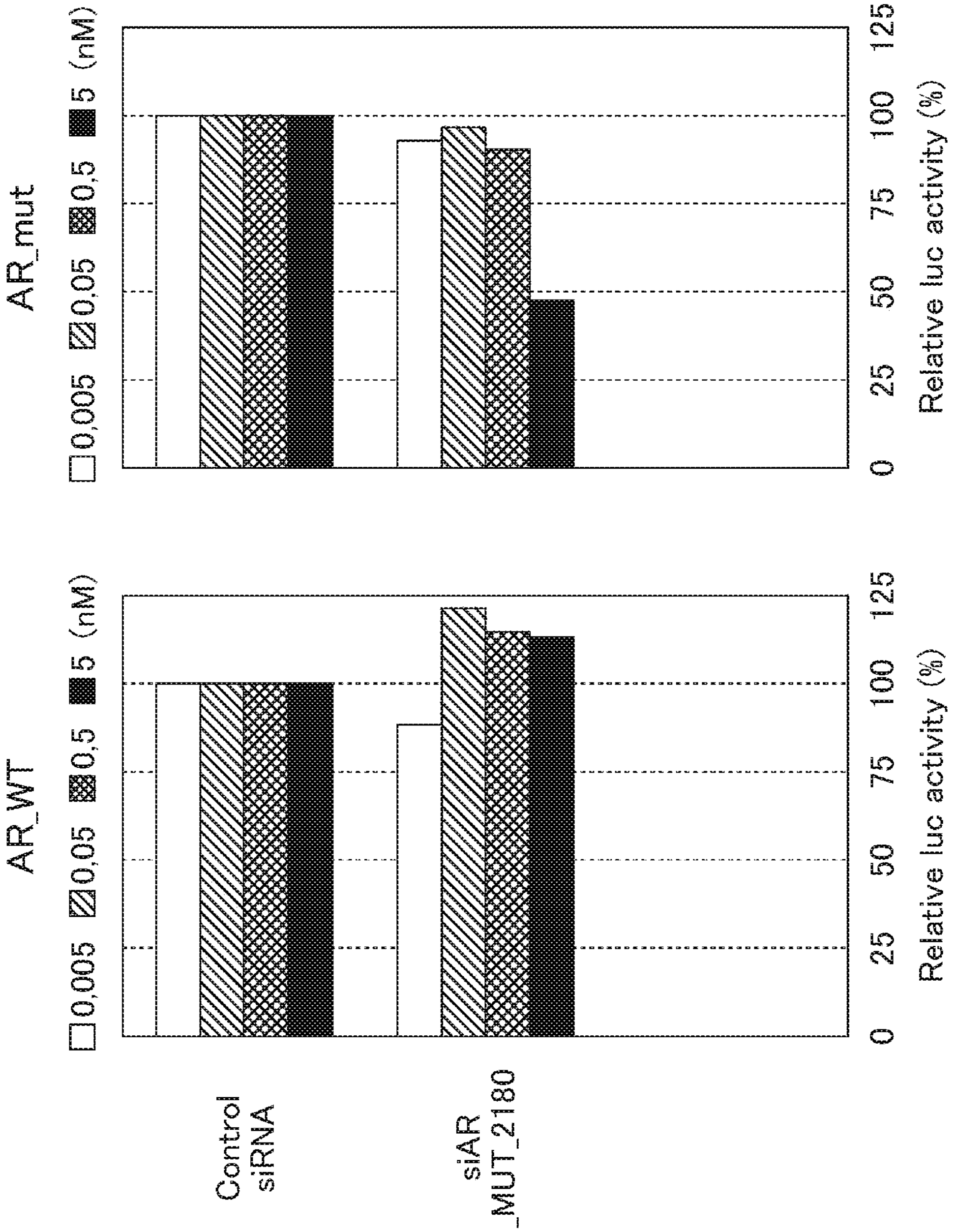
FIG. 19 shows graphs of the results on silencing abilities of siRNAs that target the AR gene, in each of which position 11 corresponded to the position of the point mutation, the base at the 5'-end of the guide strand was changed from guanine to uracil, the base at the 5'-end of the passenger strand was changed from uracil to guanine, the group at the 2'-position of the pentose in each of ribonucleotides at positions 6-8 of the guide strand was replaced by $OCH_3$, and the base at position 6 of the guide strand was mismatched by changing it from adenine to uracil, in an example of the present invention.
Figure 20:
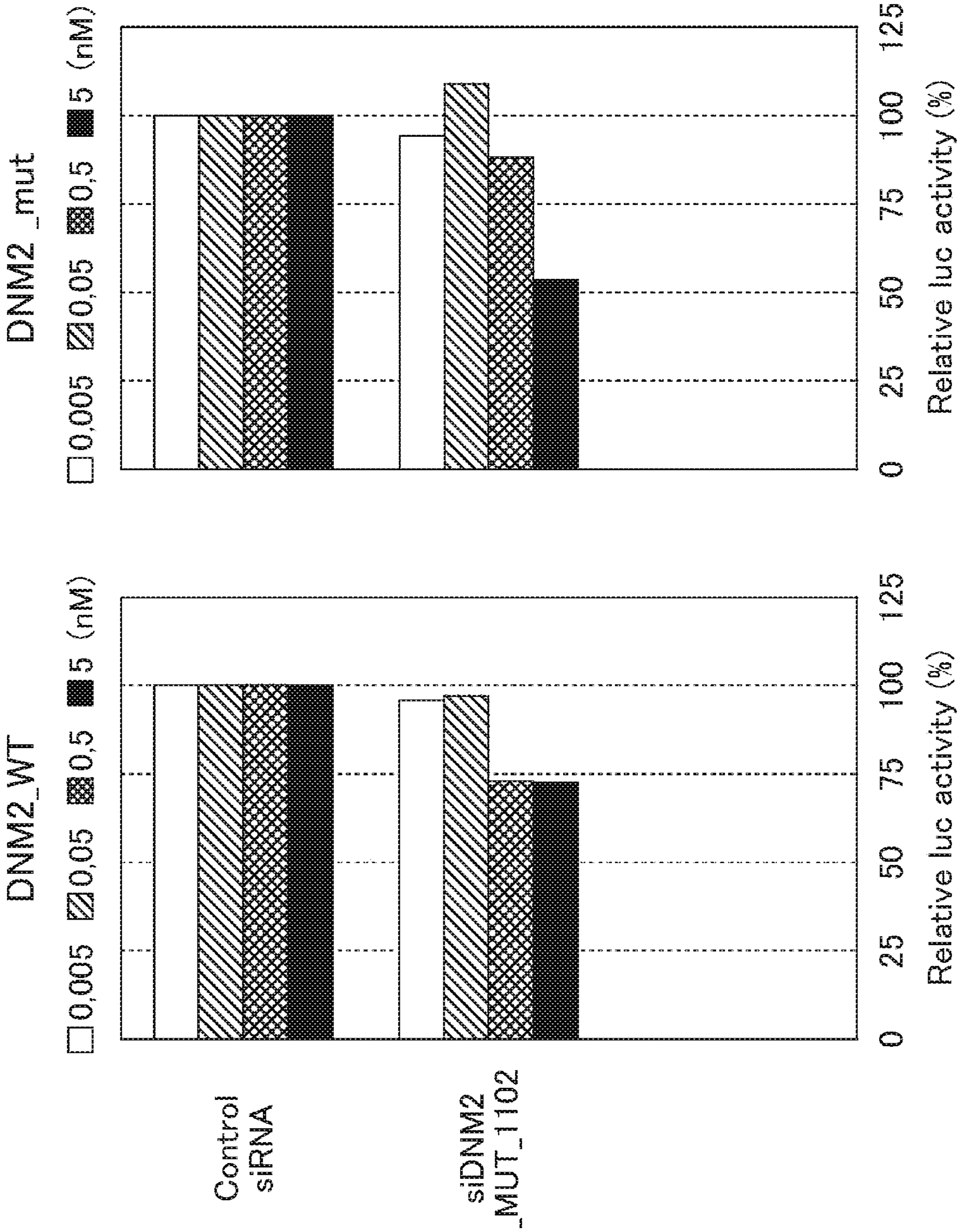
FIG. 20 shows graphs of the results on silencing abilities of siRNAs that target the DNM2 gene, in each of which position 11 corresponded to the position of the point mutation, the base at the 5'-end of the guide strand was changed from guanine to uracil, the base at the 5'-end of the passenger strand was changed from uracil to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 21:
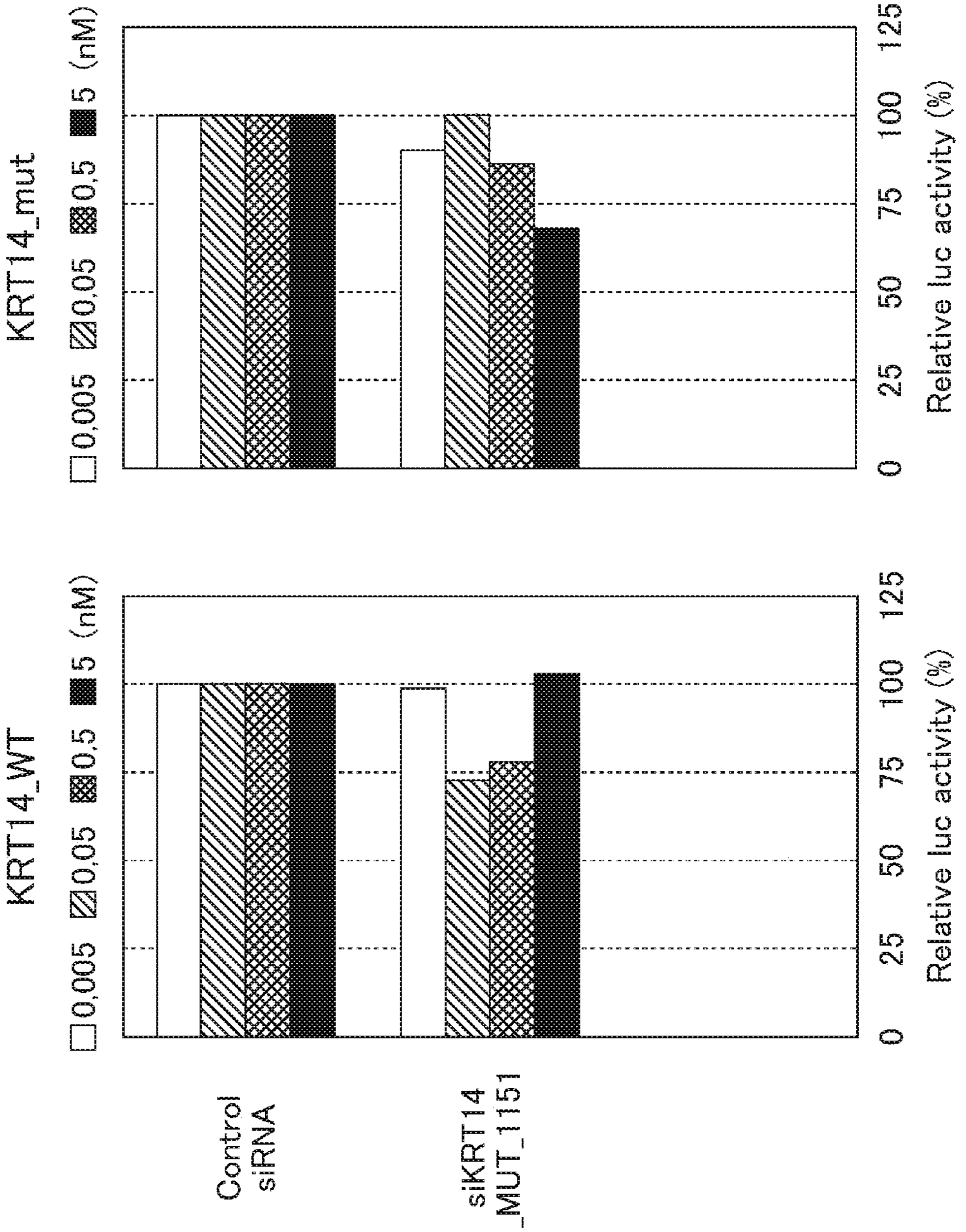
FIG. 21 shows graphs of the results on silencing abilities of siRNAs that target the KRT14 gene, in each of which position 11 corresponded to the position of the point mutation, the base at the 5'-end of the guide strand was changed from guanine to uracil, the group at the 2'-position of the pentose in each of ribonucleotides at positions 6-8 of the guide strand was replaced by $OCH_3$, and the base at position 6 of the guide strand was mismatched by changing it from guanine to cytosine, in an example of the present invention.
Figure 22:
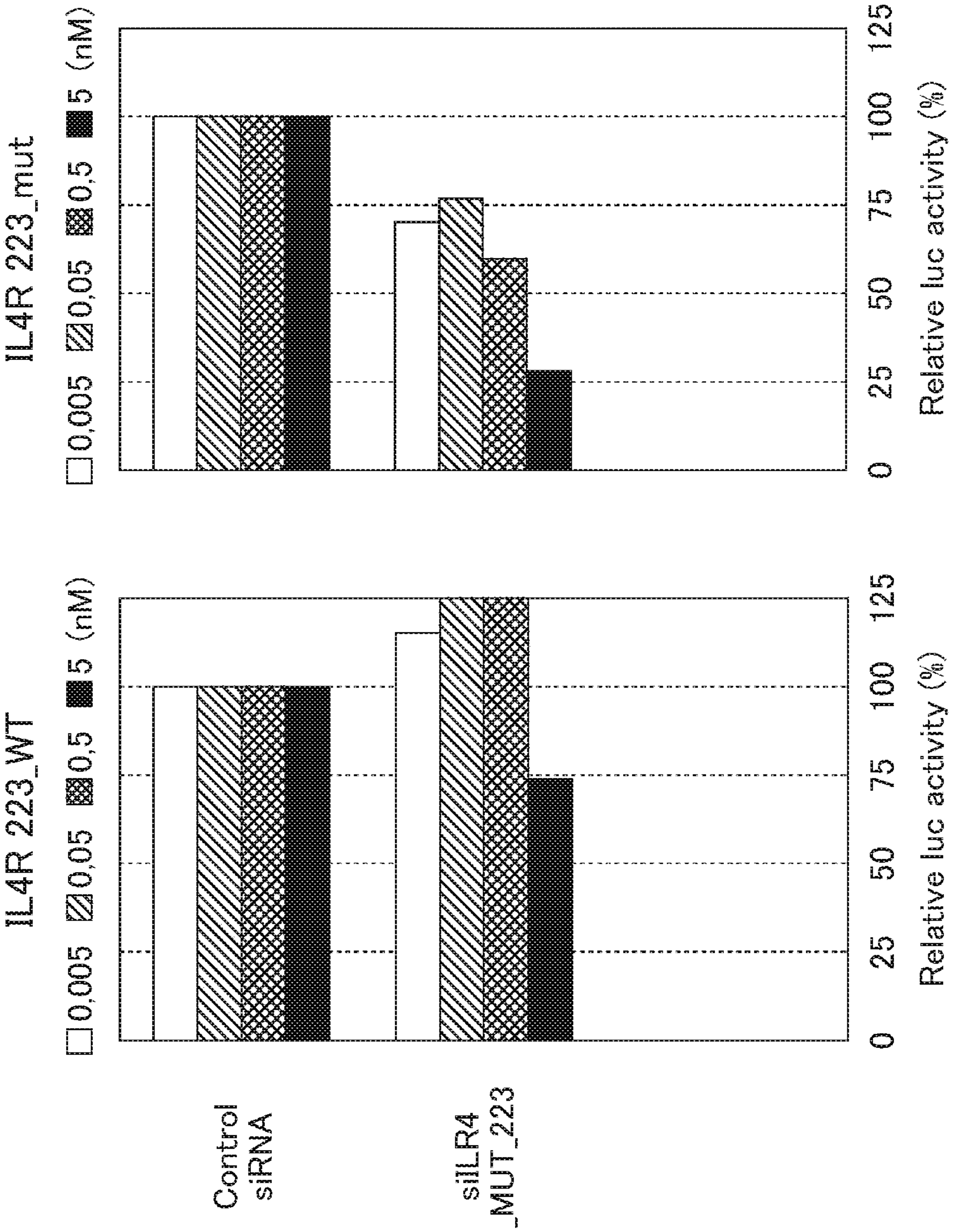
FIG. 22 shows graphs of the results on silencing abilities of a first siRNA that targets the IL4R gene, in which position 11 corresponded to the position of the point mutation, the base at the 5'-end of the passenger strand was changed from adenine to guanine, the group at the 2'-position of the pentose in each of ribonucleotides at positions 6-8 of the guide strand was replaced by $OCH_3$, and the base at position 6 of the guide strand was mismatched by changing it from adenine to uracil, in an example of the present invention.
Figure 23:
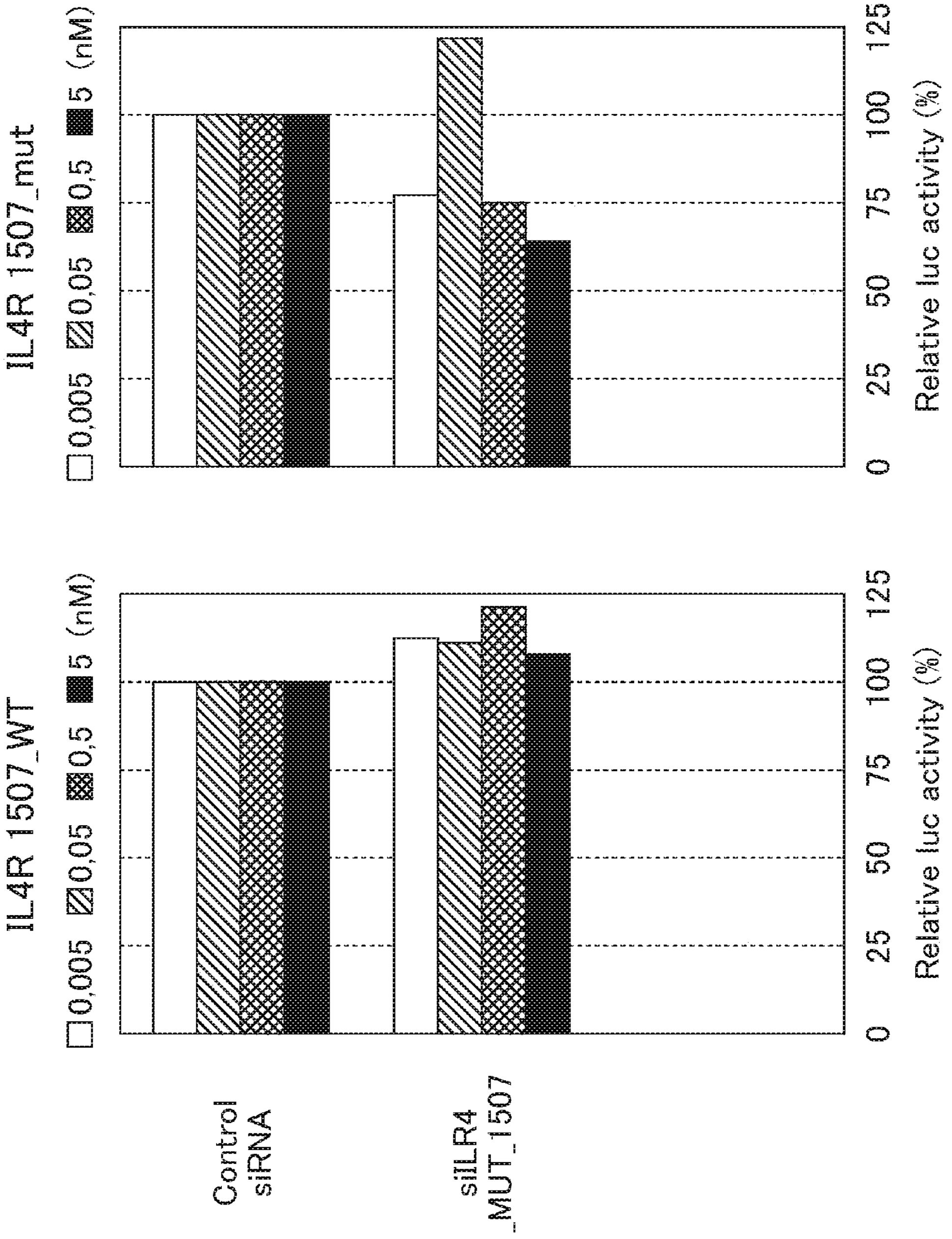
FIG. 23 shows graphs of the results on silencing abilities of a second siRNA that targets the IL4R gene, in which position 11 corresponded to the position of the point mutation, the base at the 5'-end of the passenger strand was changed from uracil to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 24:
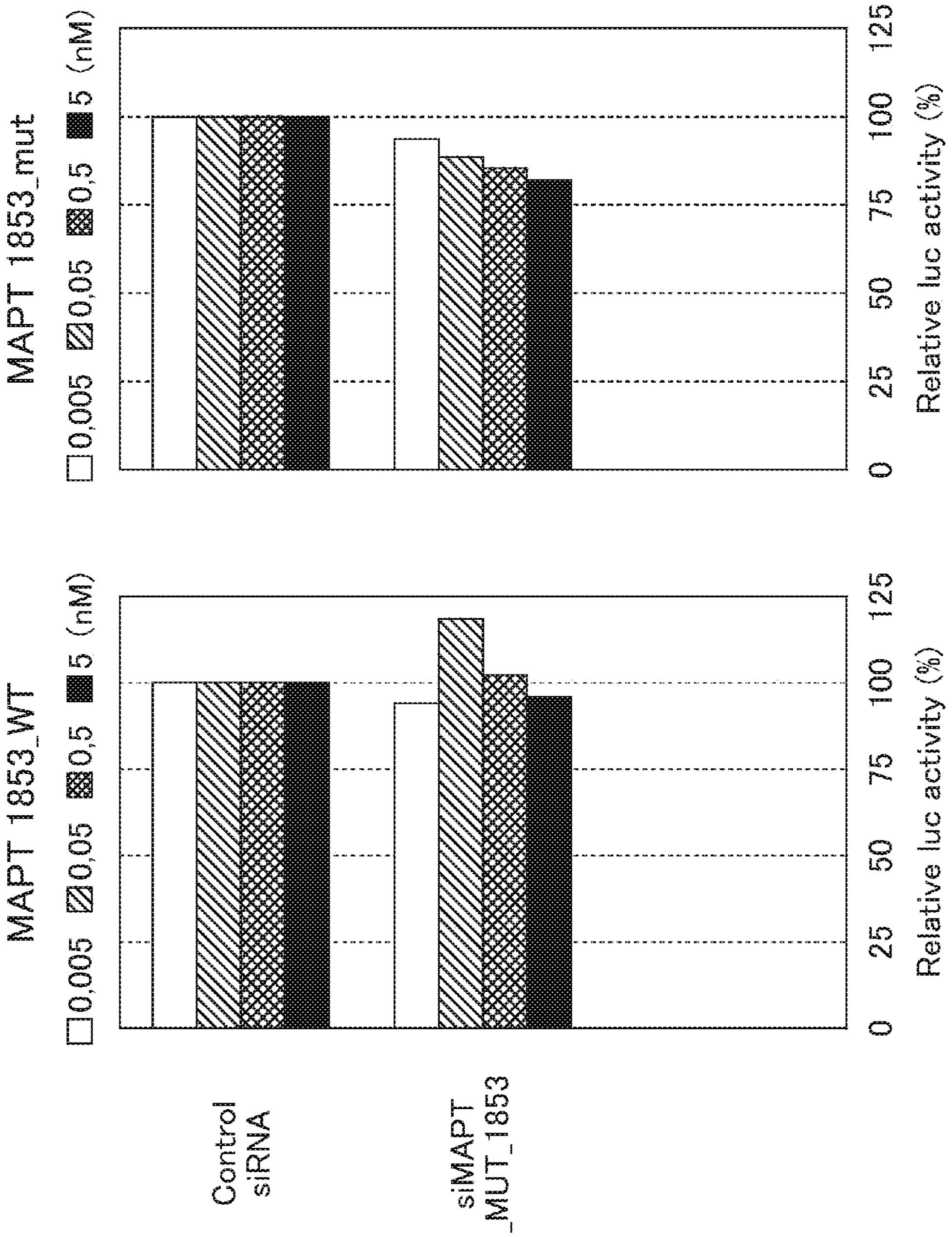
FIG. 24 shows graphs of the results on silencing abilities of siRNAs that target the MAPT gene, in each of which position 11 corresponded to the position of the point mutation, the base at the 5'-end of the guide strand was changed from guanine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 25:
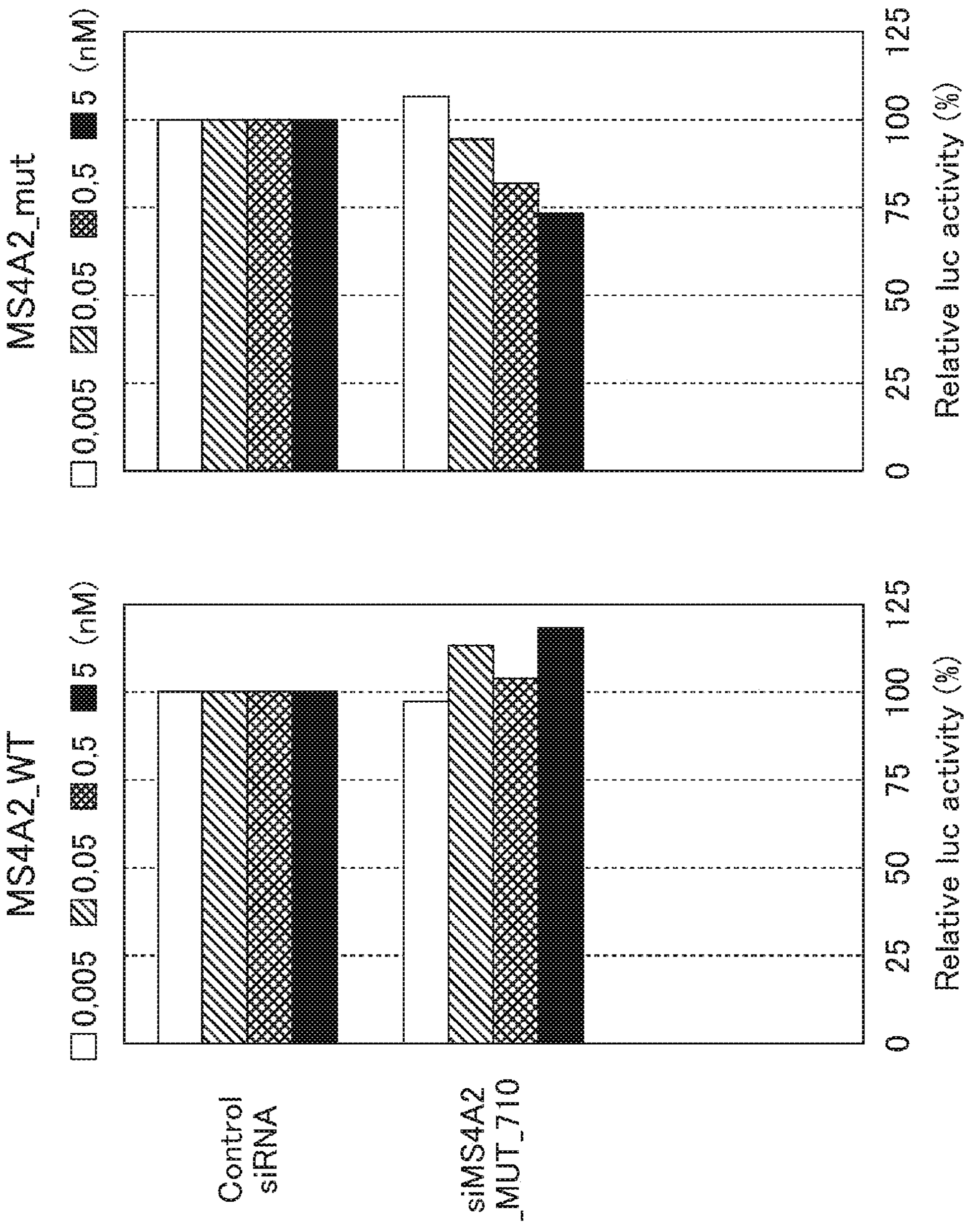
FIG. 25 shows graphs of the results on silencing abilities of siRNAs that target the MS4A2 gene, in each of which position 11 corresponded to the position of the point mutation, the base at the 5'-end of the guide strand was changed from adenine to uracil, the base at the 5'-end of the passenger strand was changed from cytosine to guanine, the group at the 2'-position of the pentose in each of ribonucleotides at positions 6-8 of the guide strand was replaced by $OCH_3$, and the base at position 6 of the guide strand was mismatched by changing it from adenine to uracil, in an example of the present invention.
Figure 26:
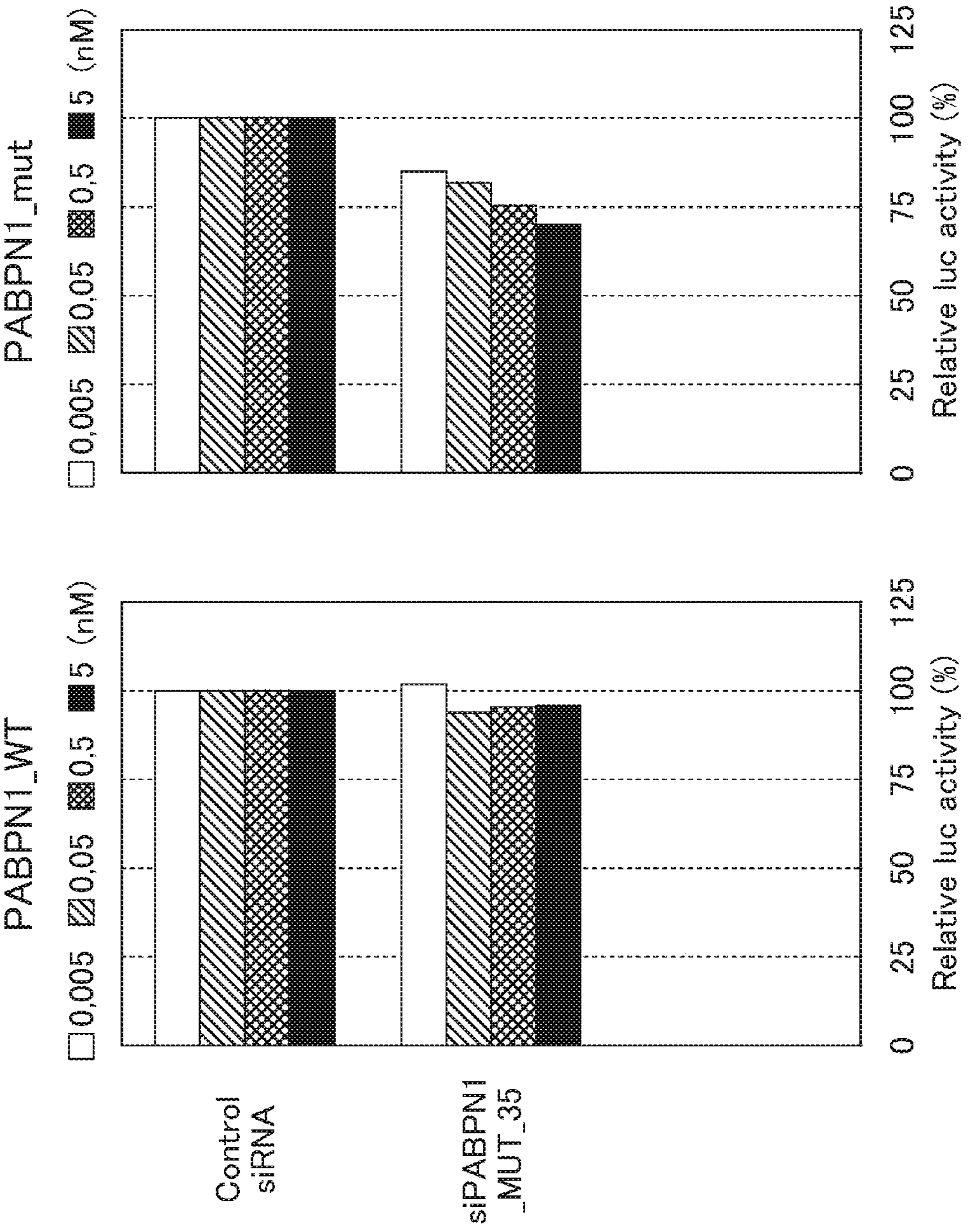
FIG. 26 shows graphs of the results on silencing abilities of siRNAs that target the PABPN1 gene, in each of which position 11 corresponded to the position of the point mutation, the base at the 5'-end of the guide strand was changed from guanine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 27:
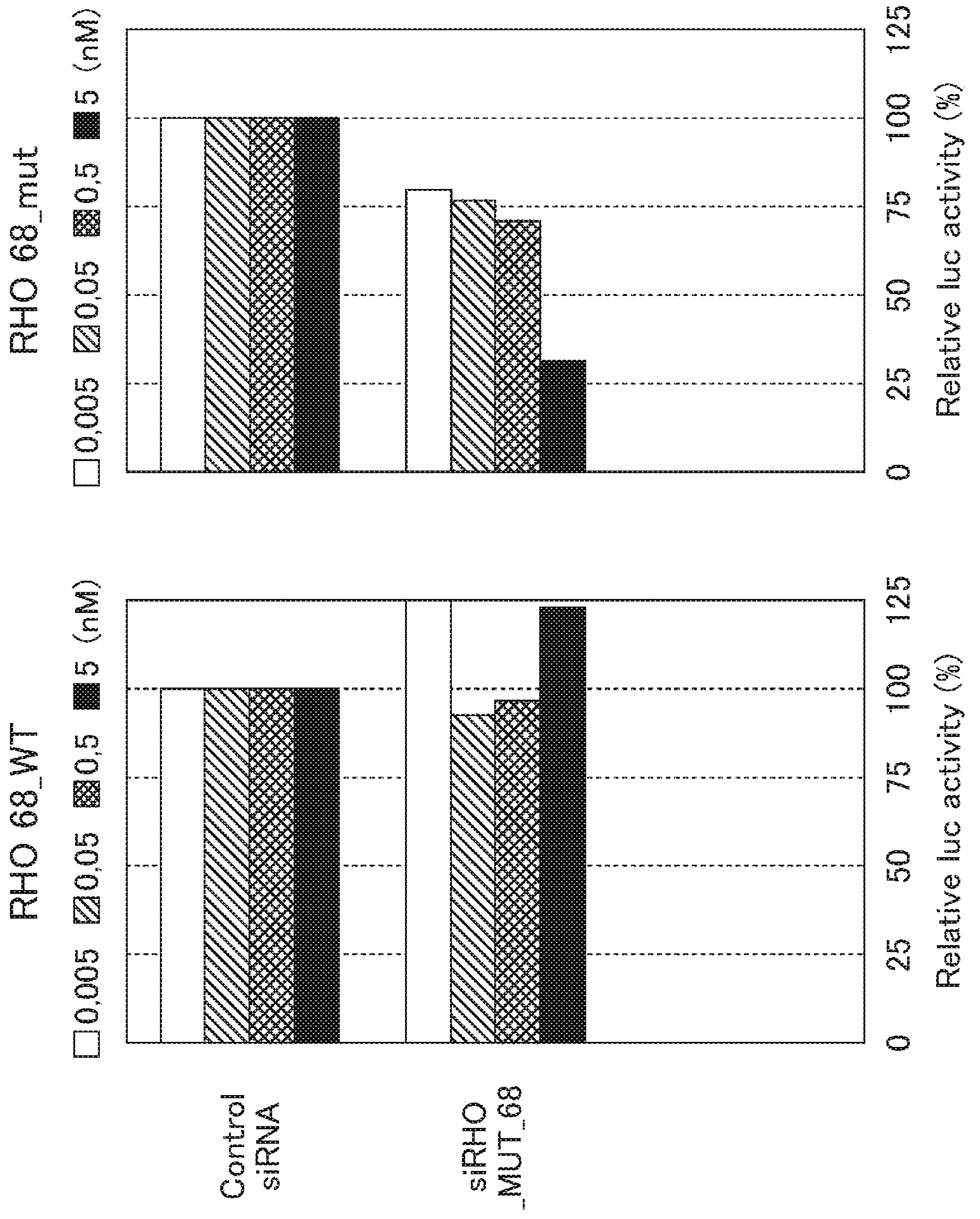
FIG. 27 shows graphs of the results on silencing abilities of a first siRNA that targets the RHO gene, in which position 11 corresponded to the position of the point mutation, the base at the 5'-end of the guide strand was changed from guanine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 28:
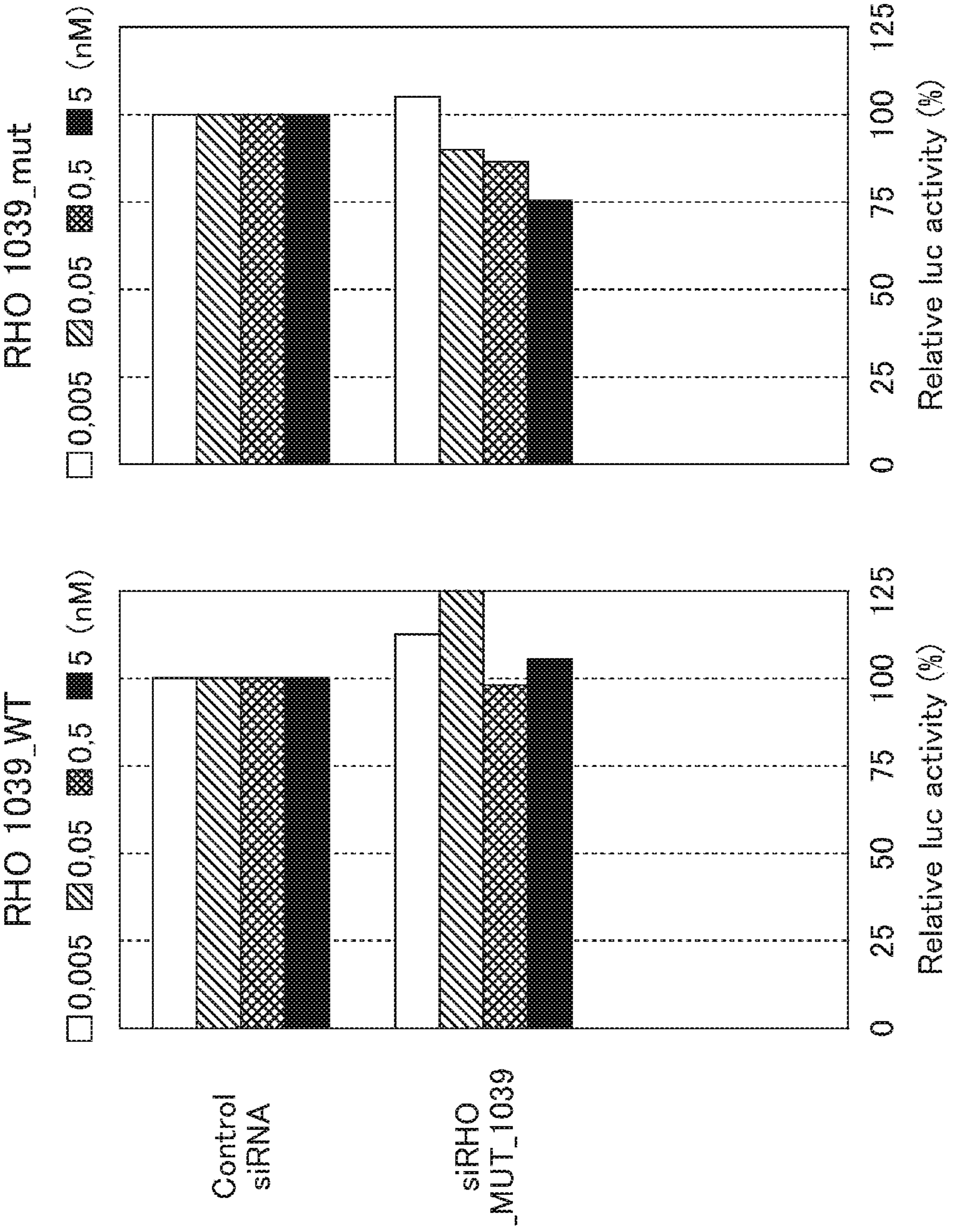
FIG. 28 shows graphs of the results on silencing abilities of a second siRNA that targets the RHO gene, in which position 11 corresponded to the position of the point mutation, the base at the 5'-end of the passenger strand was changed from adenine to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 29:
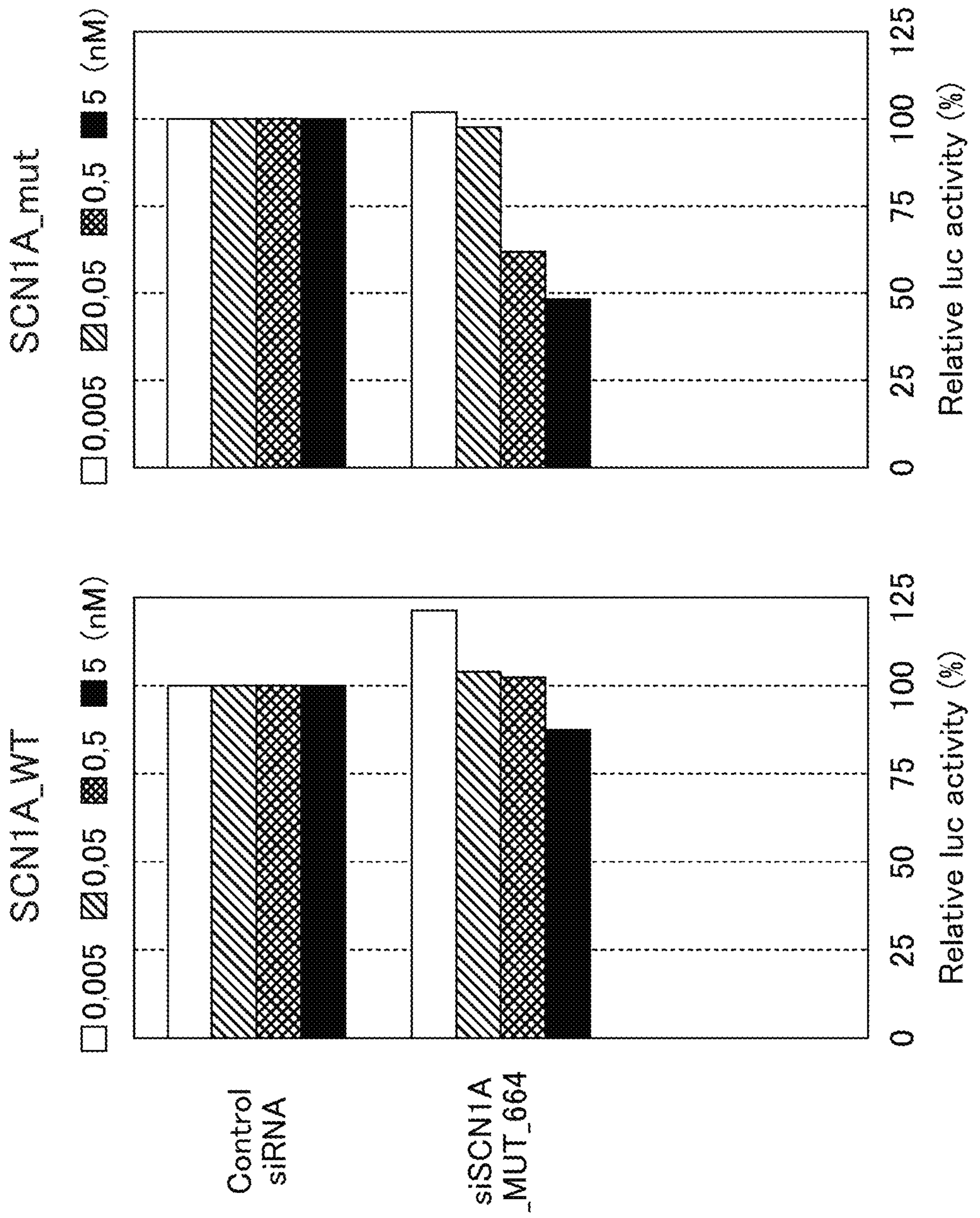
FIG. 29 shows graphs of the results on silencing abilities of siRNAs that target the SCN1A gene, in each of which position 11 corresponded to the position of the point mutation, the group at the 2'-position of the pentose in each of ribonucleotides at positions 6-8 of the guide strand was replaced by $OCH_3$, and the base at position 6 of the guide strand was mismatched by changing it from uracil to adenine, in an example of the present invention.
Figure 30:
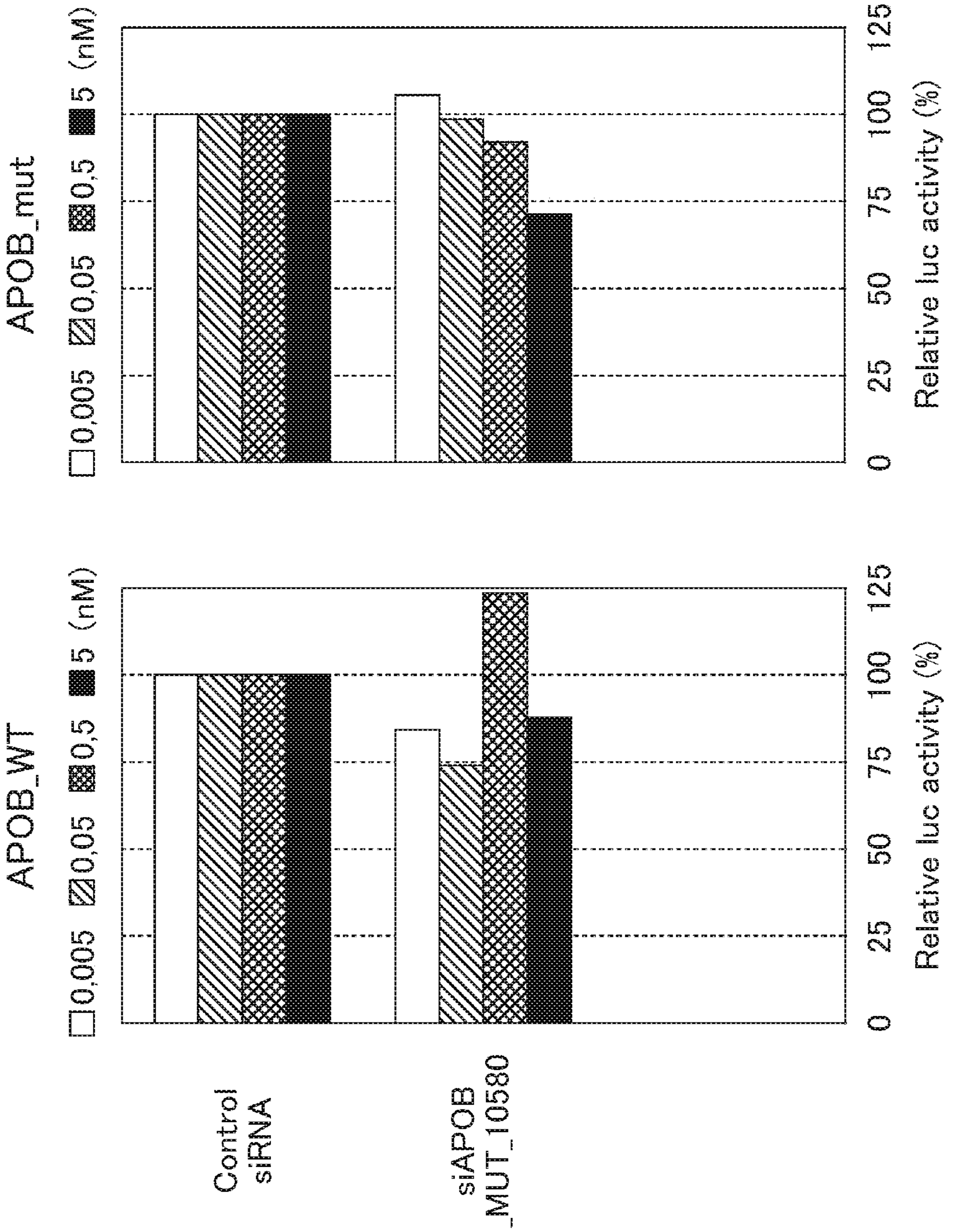
FIG. 30 shows graphs of the results on silencing abilities of siRNAs that target the APOB gene, in each of which position 11 corresponded to the position of the point mutation, the base at the 5'-end of the guide strand was changed from cytosine to uracil, the group at the 2'-position of the pentose in each of ribonucleotides at positions 6-8 of the guide strand was replaced by $OCH_3$, and the base at position 6 of the guide strand was mismatched by changing it from adenine to uracil, in an example of the present invention.
Figure 31:
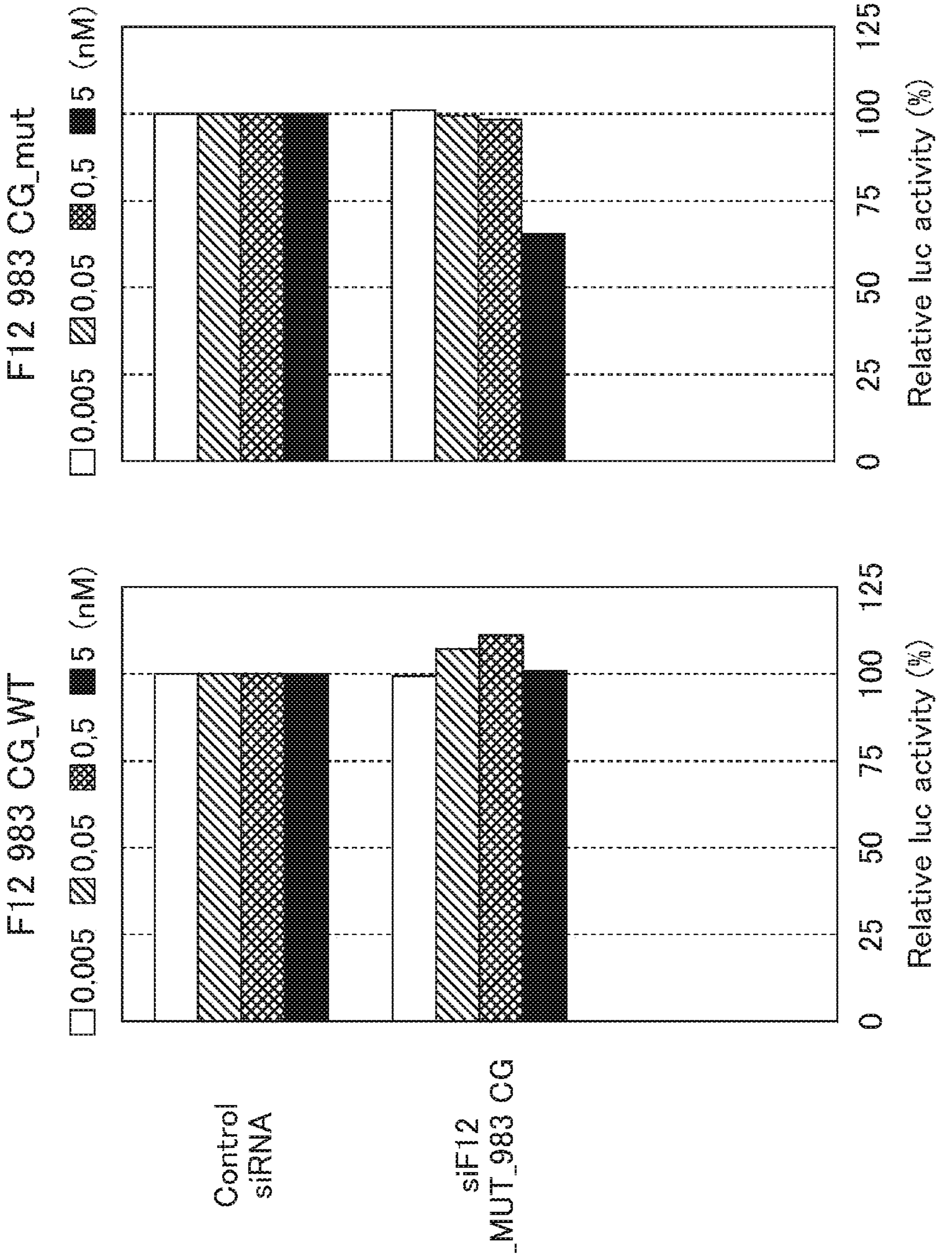
FIG. 31 shows graphs of the results on silencing abilities of siRNAs that target the F12 gene, in each of which position 11 corresponded to the position of the point mutation, the base at the 5'-end of the guide strand was changed from guanine to uracil, the base at the 5'-end of the passenger strand was changed from uracil to guanine, the group at the 2'-position of the pentose in each of ribonucleotides at positions 6-8 of the guide strand was replaced by $OCH_3$, and the base at position 6 of the guide strand was mismatched by changing it from guanine to cytosine, in an example of the present invention.
Figure 32:
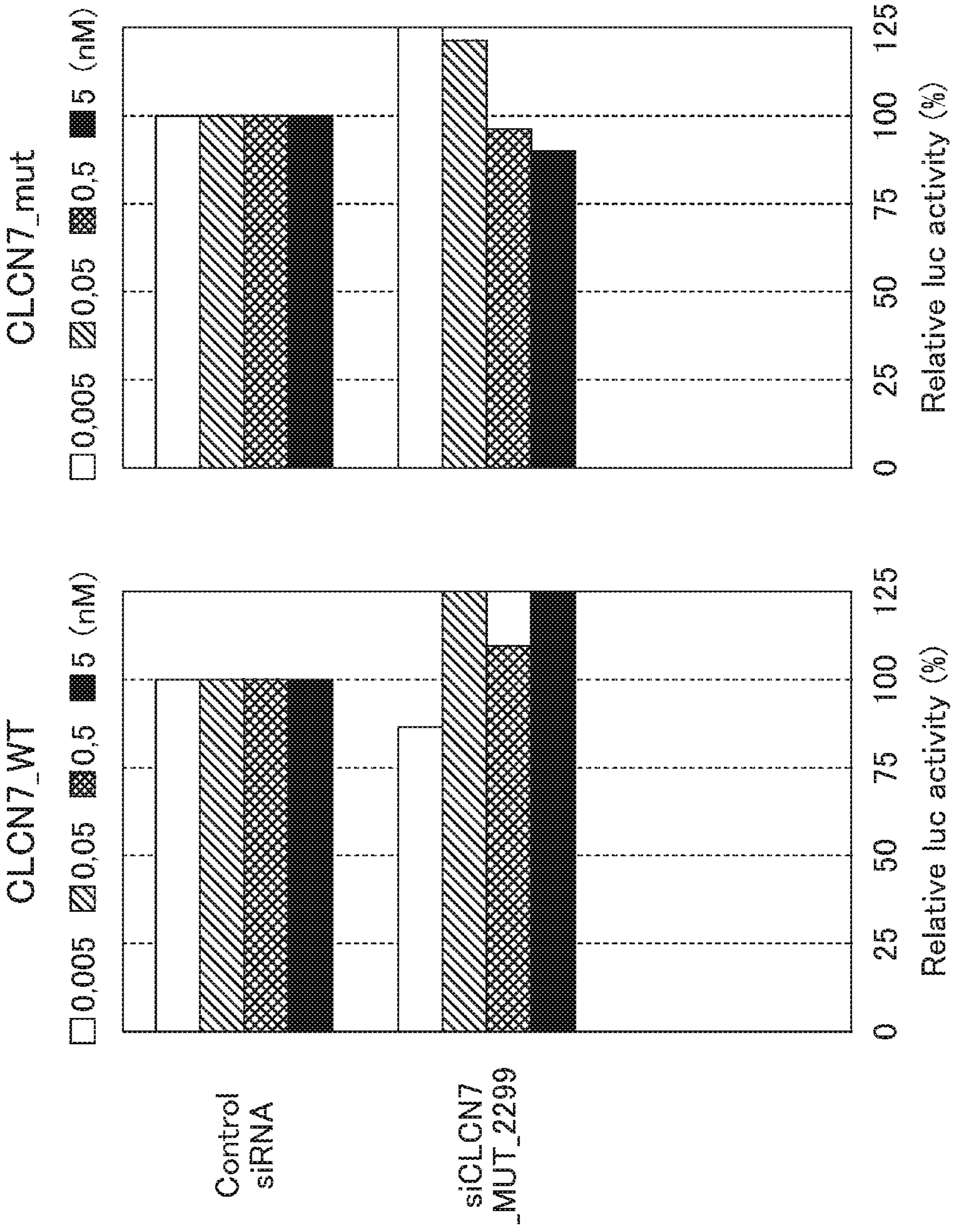
FIG. 32 shows graphs of the results on silencing abilities of siRNAs that target the CLCN7 gene, in each of which position 11 corresponded to the position of the point mutation, the base at the 5'-end of the guide strand was changed from adenine to uracil, the base at the 5'-end of the passenger strand was changed from uracil to guanine, the group at the 2'-position of the pentose in each of ribonucleotides at positions 6-8 of the guide strand was replaced by $OCH_3$, and the base at position 6 of the guide strand was mismatched by changing it from guanine to cytosine, in an example of the present invention.
Figure 33:
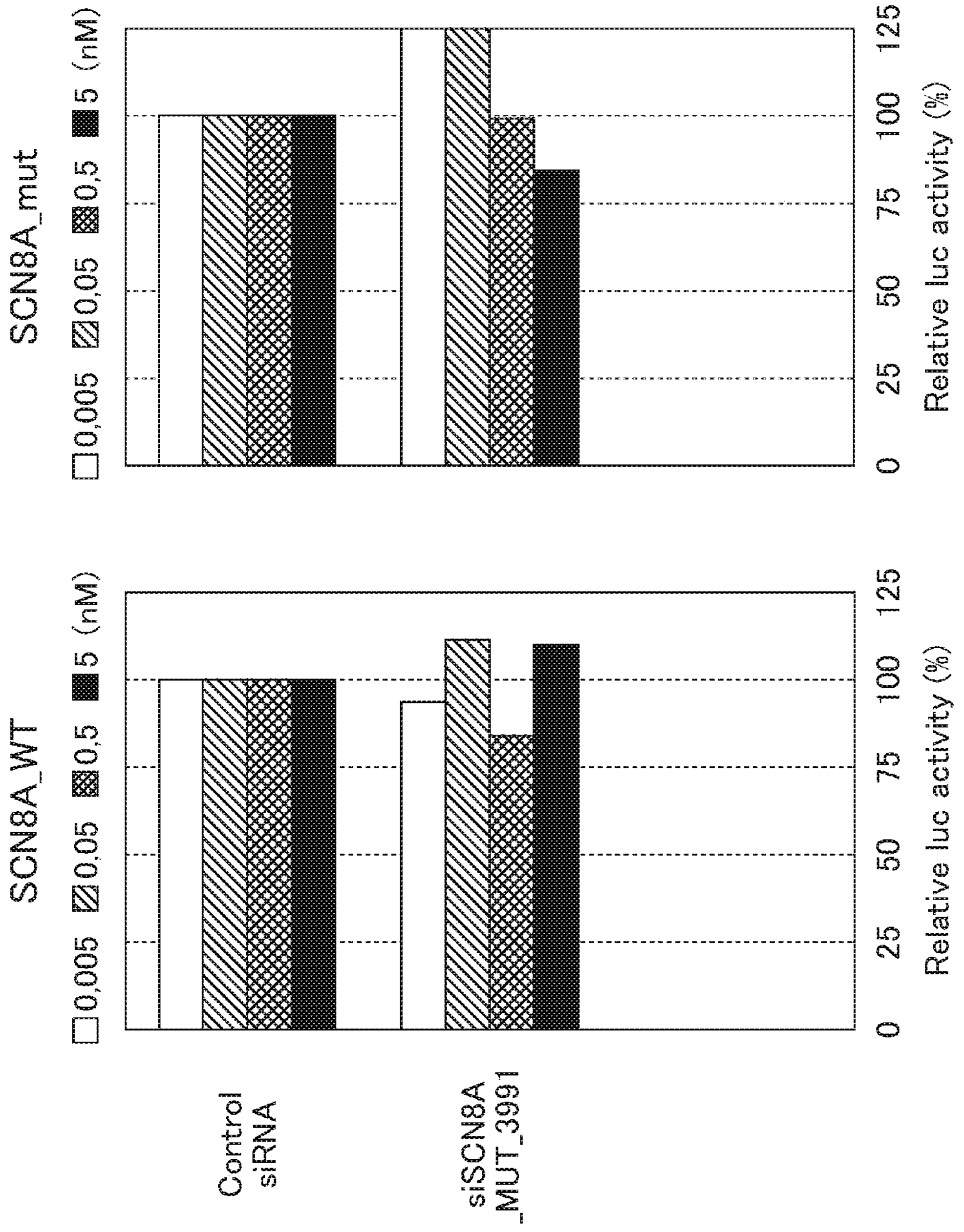
FIG. 33 shows graphs of the results on silencing abilities of siRNAs that target the SCN8A gene, in each of which position 11 corresponded to the position of the point mutation, the base at the 5'-end of the guide strand was changed from cytosine to uracil, the base at the 5'-end of the passenger strand was changed from uracil to guanine, the group at the 2'-position of the pentose in each of ribonucleotides at positions 6-8 of the guide strand was replaced by $OCH_3$, and the base at position 6 of the guide strand was mismatched by changing it from cytosine to guanine, in an example of the present invention.
Figure 34:
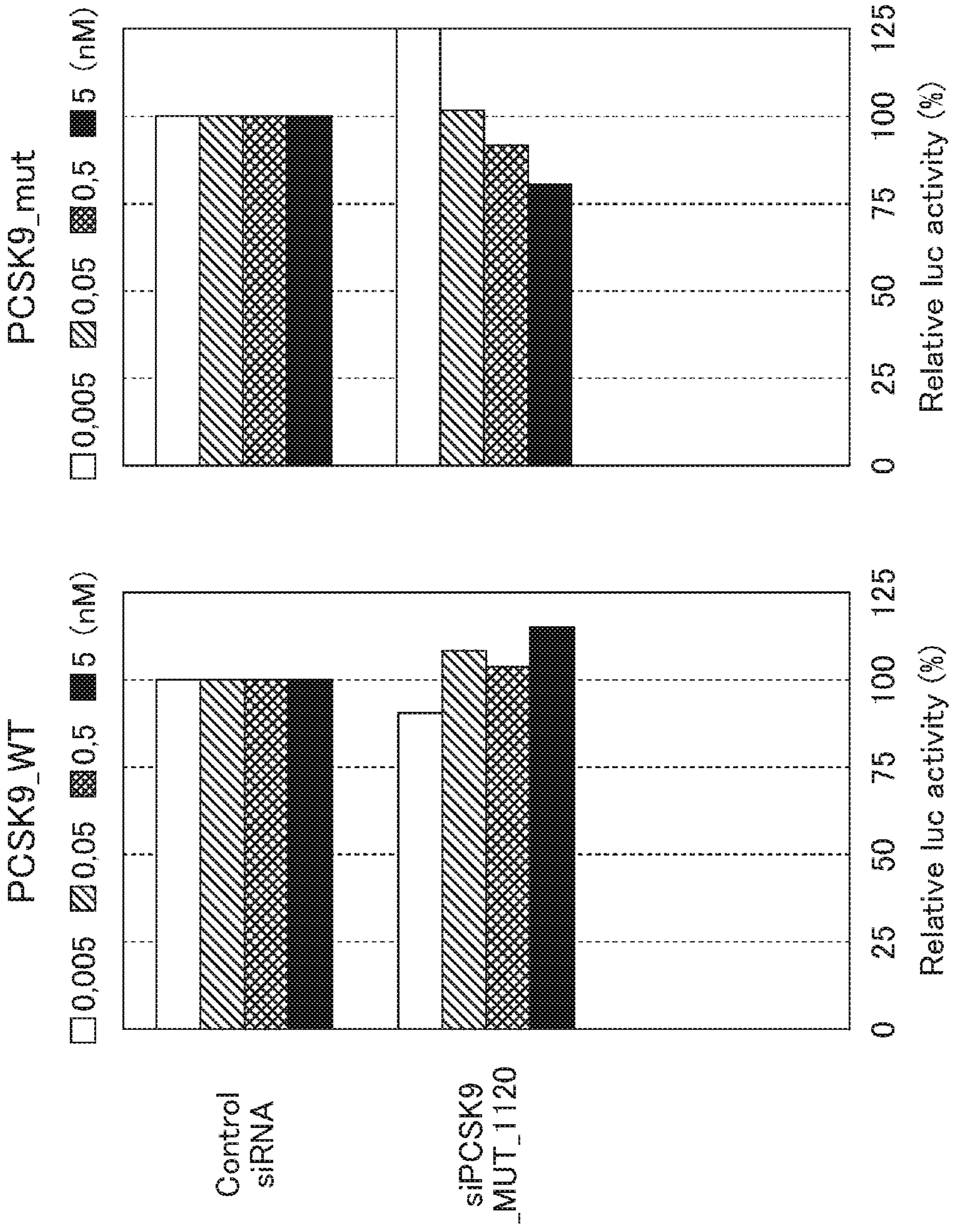
FIG. 34 shows graphs of the results on silencing abilities of siRNAs that target the PCSK9 gene, in each of which position 11 corresponded to the position of the point mutation, the base at the 5'-end of the guide strand was changed from guanine to uracil, the base at the 5'-end of the passenger strand was changed from cytosine to guanine, the group at the 2'-position of the pentose in each of ribonucleotides at positions 6-8 of the guide strand was replaced by $OCH_3$, and the base at position 6 of the guide strand was mismatched by changing it from guanine to cytosine, in an example of the present invention.
Figure 35:
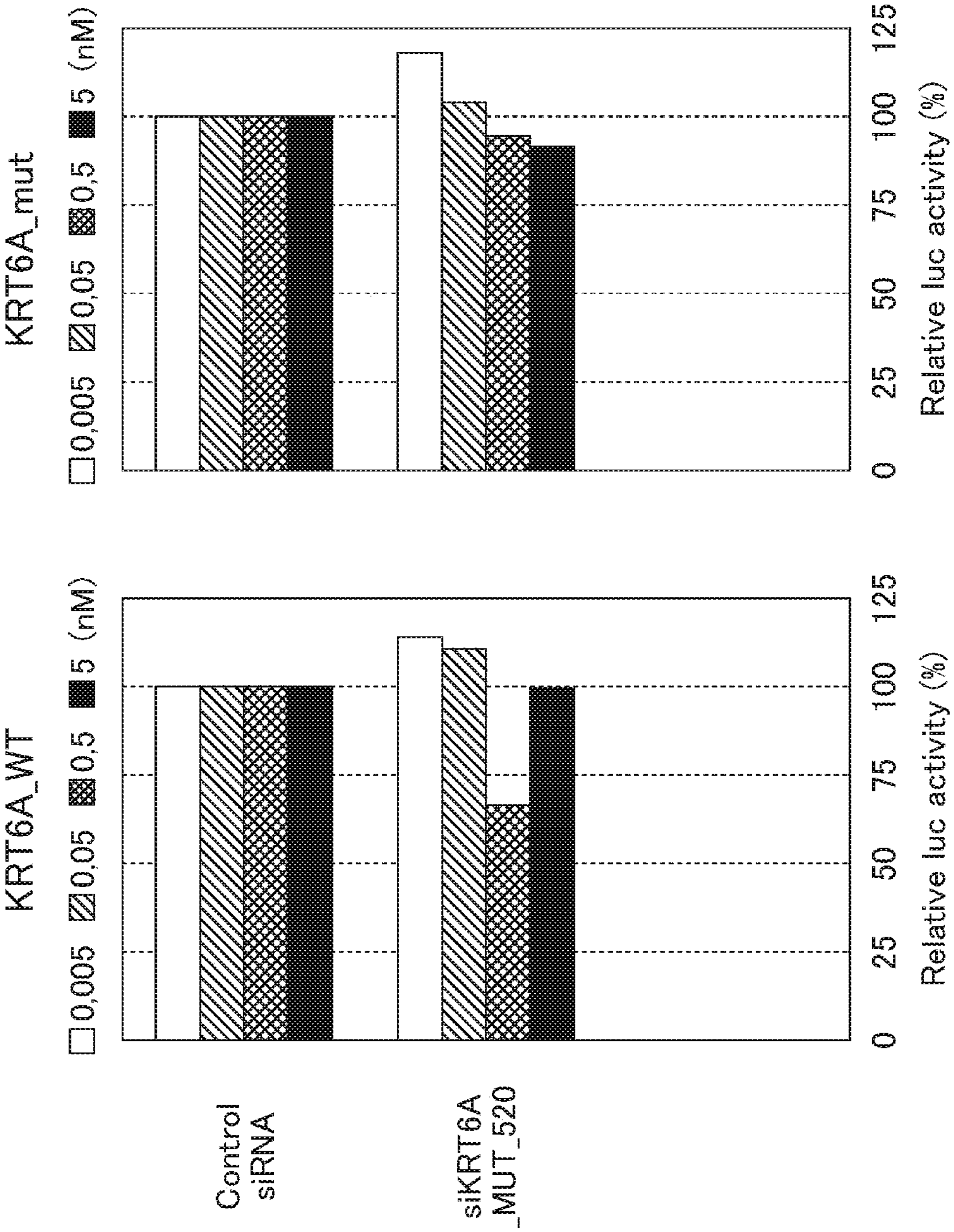
FIG. 35 shows graphs of the results on silencing abilities of siRNAs that target the KRT6A gene, in each of which position 11 corresponded to the position of the point mutation, the base at the 5'-end of the guide strand was changed from adenine to uracil, the base at the 5'-end of the passenger strand was changed from adenine to guanine, the group at the 2'-position of the pentose in each of ribonucleotides at positions 6-8 of the guide strand was replaced by $OCH_3$, and the base at position 6 of the guide strand was mismatched by changing it from guanine to cytosine, in an example of the present invention.

FIG. 10 shows gene silencing effects of the siRNAs.

N(182)11A effectively suppressed the expression of the wild-type N182 allele more than that of the G-mutant N182 allele. In contrast, N(182)11G effectively suppressed the expression of the A-mutant N182 allele more than that of the wild-type N182 allele. N(182) 11ArevOM(6-8)M5 lost silencing abilities to the wild-type allele and exhibited slightly reduced silencing abilities to the G-mutant N182 allele, resulting in a higher specificity for the G-mutant N182 allele.

Example 3

In this example, various genes listed in Table 2 were used as the target genes to be silenced to show that siRNAs designed according to the method disclosed herein suppress the expression of the mutant alleles but do not suppress the expression of the wild-type alleles.

First, as reporters for examining gene silencing effects, DNAs with the same nucleotide sequences as wild-type (wt) and mutant alleles were chemically synthesized and inserted into the 3'-UTR of the luciferase gene in an expression vector (psiCHECK) to construct wild-type and mutant reporters, respectively. The sequences of the segments incorporated into the vectors are indicated in Table 2.

In the nucleotide sequences in the tables, lowercase letters denote sequences for ligating to a vector, and capital letters denote sequences derived from a gene. The parentheses in the K-ras gene indicate the type of mutation, the parentheses in the HTT gene indicate the position in the genome, and the parentheses in other genes indicate a place counted from the translation start site (i.e., A in the start codon ATG). "P" stands for a passenger strand, and "G" stands for a guide strand.

TABLE 2

| Gene Name (Position of mutation) | Function | Strand | Name | Sequence | Seq. ID No. |
|---|---|---|---|---|---|
| HTT | Wild-type | S | HTT_363125_WT_s | tcgagGTTAAGAGATCCCCACAGTACTTCAACGCTAGAAGAACACAg | 76 |
| (rs363125) | reporter | AS | HTT_363125_WT_as | aattcTGTGTTCTTCTAGCGTTGAAGTACTGTGGGGATCTCTTAACc | 77 |
| | Mutant | S | HTT_363125_SNP_s | tcgagGTTAAGAGATCCCCACAGTAATTCAACGCTAGAAGAACACAg | 78 |
| | reporter | AS | HTT_363125_SNP_as | aattcTGTGTTCTTCTAGCGTTGAATTACTGTGGGGATCTCTTAACc | 79 |
| HTT | Wild-type | S | HTT_362307_WT_s | tcgagCCGGAGCCTTTGGAAGTCTGCGCCCTTGTGCCCTGCCTCCAg | 80 |
| (rs362307) | reporter | AS | HTT_362307_WT_as | aattcTGGAGGCAGGGCACAAGGGCGCAGACTTCCAAAGGCTCCGGc | 81 |
| | Mutant | S | HTT_362307_SNP_s | tcgagCCGGAGCCTTTGGAAGTCTGTGCCCTTGTGCCCTGCCTCCAg | 82 |
| | reporter | AS | HTT_362307_SNP_as | aattcTGGAGGCAGGGCACAAGGGCACAGACTTCCAAAGGCTCCGGc | 83 |
| HTT | Wild-type | S | HTT_362331_WT_s | tcgagCCCACGCCTGCTCCCTCATCTACTGTGTGCACTTCATCCTGg | 84 |
| (rs362331) | reporter | AS | HTT_362331_WT_as | aattcCAGGATGAAGTGCACACAGTAGATGAGGGAGCAGGCGTGGGc | 85 |
| | Mutant | S | HTT_362331_SNP_s | tcgagCCCACGCCTGCTCCCTCATCCACTGTGTGCACTTCATCCTGg | 86 |
| | reporter | AS | HTT_362331_SNP_as | aattcCAGGATGAAGTGCACACAGTGGATGAGGGAGCAGGCGTGGGc | 87 |
| ATXN3 | Wild-type | S | ATXN3_WT_s | tcgagAGCAGCAGCAGCAGCAGCAGGGGGACCTATCAGGACAGAGTg | 88 |
| | reporter | AS | ATXN3_WT_as | aattcACTCTGTCCTGATAGGTCCCCCTGCTGCTGCTGCTGCTGCTc | 89 |
| | Mutant | S | ATXN3_SNP_s | tcgagAGCAGCAGCAGCAGCAGCAGCGGGACCTATCAGGACAGAGTg | 90 |
| | reporter | AS | ATXN3_SNP_as | aattcACTCTGTCCTGATAGGTCCCGCTGCTGCTGCTGCTGCTGCTc | 91 |
| ZMYM3 | Wild-type | S | ZMYM3_WT_Sense | tcgagTGCTGGAGACCATCCACTGGCGTGGGCAGATCCGTCATTTCg | 92 |
| | reporter | AS | ZMYM3_WT_Anti-sense | aattcGAAATGACGGATCTGCCCACGCCAGTGGATGGTCTCCAGCAc | 93 |
| | Mutant | S | ZMYM3_2206_Sense | tcgagTGCTGGAGACCATCCACTGGTGTGGGCAGATCCGTCATTTCg | 94 |
| | reporter | AS | ZMYM3_2206_Anti-sense | aattcGAAATGACGGATCTGCCCACAGCAGTGGATGGTCTCCAGCAc | 95 |
| CTNNB1 | Wild-type | S | CTNNB1_WT_Sense | tcgagGAATCCATTCTGGTGCCACTACCACAGCTCCTTCTCTGAGTg | 96 |
| | reporter | AS | CTNNB1_WT_Anti-sense | aattcACTCAGAGAAGGAGCTGTGGTAGTGGCACCAGAATGGATTCc | 97 |
| | Mutant | S | CTNNB1_121_Sense | tcgagGAATCCATTCTGGTGCCACTGCCACAGCTCCTTCTCTGAGTg | 98 |
| | reporter | AS | CTNNB1_121_Anti-sense | aattcACTCAGAGAAGGAGCTGTGGCAGTGGCACCAGAATGGATTCc | 99 |
| SMARCA4 | Wild-type | S | SMARCA4_WT_Sense | tcgagACCCCGCCGCCTGCTGCTGACGGGCACACCGCTGCAGAACAg | 100 |
| | reporter | AS | SMARCA4_WT_Anti-sense | aattcTGTTCTGCAGCGGTGTGCCCGTCAGCAGCAGGCGGCGGGGTc | 101 |
| | Mutant | S | SMARCA4_2729_Sense | tcgagACCCCGCCGCCTGCTGCTGATGGGCACACCGCTGCAGAACAg | 102 |
| | reporter | AS | SMARCA4_2729_Anti-sense | aattcTGTTCTGCAGCGGTGTGCCCATCAGCAGCAGGCGGCGGGGTc | 103 |
| SMO | Wild-type | S | SMO_WT_Sense | tcgagTGGCCCCAATCGGCCTGGTGCTCATCGTGGGAGGCTACTTCg | 104 |
| | reporter | AS | SMO_WT_Anti-sense | aattcGAAGTAGCCTCCCACGATGAGCACCAGGCCGATTGGGGCCAc | 105 |
| | Mutant | S | SMO_1234_Sense | tcgagTGGCCCCAATCGGCCTGGTGTTCATCGTGGGAGGCTACTTCg | 106 |
| | reporter | AS | SMO_1234_Anti-sense | aattcGAAGTAGCCTCCCACGATGAACACCAGGCCGATTGGGGCCAc | 107 |
| AR | Wild-type | S | AR_WT_Sense | tcgagCAAGGCCTTGCCTGGCTTCCGCAACTTACACGTGGACGACCg | 108 |
| | reporter | AS | AR_WT_Anti-sense | aattcGGTCGTCCACGTGTAAGTTGCGGAAGCCAGGCAAGGCCTTGc | 109 |
| | Mutant | S | AR_2180_Sense | tcgagCAAGGCCTTGCCTGGCTTCCTCAACTTACACGTGGACGACCg | 110 |
| | reporter | AS | AR_2180_Anti-sense | aattcGGTCGTCCACGTGTAAGTTGAGGAAGCCAGGCAAGGCCTTGc | 111 |

TABLE 2-continued

| Gene Name (Position of mutation) | Function | Strand | Name | Sequence | Seq. ID No. |
|---|---|---|---|---|---|
| DNM2 | Wild-type | S | DNM2_WT_Sense | tcgagGAATCAATCGCATCTTCCACGAGCGGTTCCCATTTGAGCTGg | 112 |
| | reporter | AS | DNM2_WT_Anti-sense | aattcCAGCTCAAATGGGAACCGCTCGTGGAAGATGCGATTGATTCc | 113 |
| | Mutant | S | DNM2_1102_Sense | tcgagGAATCAATCGCATCTTCCACAAGCGGTTCCCATTTGAGCTGg | 114 |
| | reporter | AS | DNM2_1102_Anti-sense | aattcCAGCTCAAATGGGAACCGCTTGTGGAAGATGCGATTGATTCc | 115 |
| KRT14 | Wild-type | S | KRT14_WT_Sense | tcgagTCAAGACCCTCAACAACAAGTTTGCCTCCTTCATCGACAAGg | 116 |
| | reporter | AS | KRT14_WT_Anti-sense | aattcCTTGTCGATGAAGGAGGCAAACTTGTTGTTGAGGGTCTTGAc | 117 |
| | Mutant | S | KRT14_520_Sense | tcgagTCAAGACCCTCAACAACAAGGTTGCCTCCTTCATCGACAAGg | 118 |
| | reporter | AS | KRT14_520_Anti-sense | aattcCTTGTCGATGAAGGAGGCAACCTTGTTGTTGAGGGTCTTGAc | 119 |
| IL4R (223) | Wild-type | S | IL4R_WT_Sense | tcgagTCTCCGAAGCCCACACGTGTATCCCTGAGAACAACGGAGGCg | 120 |
| | reporter | AS | IL4R_WT_Anti-sense | aattcGCCTCCGTTGTTCTCAGGGATACACGTGTGGGCTTCGGAGAc | 121 |
| | Mutant | S | IL4R_223_Sense | tcgagTCTCCGAAGCCCACACGTGTGTCCCTGAGAACAACGGAGGCg | 122 |
| | reporter | AS | IL4R_223_Anti-sense | aattcGCCTCCGTTGTTCTCAGGGACACACGTGTGGGCTTCGGAGAc | 123 |
| IL4R (1507) | Wild-type | S | IL4R_WT_Sense | tcgagCTTACCGCAGCTTCAGCAACTCCCTGAGCCAGTCACCGTGTg | 124 |
| | reporter | AS | IL4R_WT_Anti-sense | aattcACACGGTGACTGGCTCAGGGAGTTGCTGAAGCTGCGGTAAGc | 125 |
| | Mutant | S | IL4R_1507_Sense | tcgagCTTACCGCAGCTTCAGCAACCCCCTGAGCCAGTCACCGTGTg | 126 |
| | reporter | AS | IL4R_1507_Anti-sense | aattcACACGGTGACTGGCTCAGGGGGTTGCTGAAGCTGCGGTAAGc | 127 |
| MAPT (1853) | Wild-type | S | MAPT_WT_Sense | tcgagGGATAATATCAAACACGTCCCGGGAGGCGGCAGTGTGCAAAg | 128 |
| | reporter | AS | MAPT_WT_Anti-sense | aattcTTTGCACACTGCCGCCTCCCGGGACGTGTTTGATATTATCCc | 129 |
| | Mutant | S | MAPT_1853_Sense | tcgagGGATAATATCAAACACGTCCTGGGAGGCGGCAGTGTGCAAAg | 130 |
| | reporter | AS | MAPT_1853_Anti-sense | aattcTTTGCACACTGCCGCCTCCCAGGACGTGTTTGATATTATCCc | 131 |
| MS4A2 | Wild-type | S | MS4A2_WT_Sense | tcgagTGAGTTGGAAGACCCAGGGGAAATGTCTCCTCCCATTGATTg | 132 |
| | reporter | AS | MS4A2_WT_Anti-sense | aattcAATCAATGGGAGGAGACATTTCCCCTGGGTCTTCCAACTCAc | 133 |
| | Mutant | S | MS4A2_710_Sense | tcgagTGAGTTGGAAGACCCAGGGGGAATGTCTCCTCCCATTGATTg | 134 |
| | reporter | AS | MS4A2_710_Anti-sense | aattcAATCAATGGGAGGAGACATTCCCCCTGGGTCTTCCAACTCAc | 135 |
| PABPN1 | Wild-type | S | PABPN1_WT_Sense | tcgagGGCGGCGGCAGCAGCAGCGGGGGCTGCGGGCGGTCGGGGCTg | 136 |
| | reporter | AS | PABPN1_WT_Anti-sense | aattcAGCCCCGACCGCCCGCAGCCCCCGCTGCTGCTGCCGCCGCCc | 137 |
| | Mutant | S | PABPN1_35_Sense | tcgagGGCGGCGGCAGCAGCAGCGGCGGCTGCCGGGCGGTCGGGGTg | 138 |
| | reporter | AS | PABPN1_35_Anti-sense | aattcAGCCCCGACCGCCCGCAGCCGCCGCTGCTGCTGCCGCCGCCc | 139 |
| RHO (68) | Wild-type | S | RHO_WT_Sense | tcgagGACGGGTGTGGTACGCAGCCCCTTCGAGTACCCACAGTACTg | 140 |
| | reporter | AS | RHO_WT_Anti-sense | aattcAGTACTGTGGGTACTCGAAGGGGCTGCGTACCACACCCGTCc | 141 |
| | Mutant | S | RHO_68_Sense | tcgagGACGGGTGTGGTACGCAGCCACTTCGAGTACCCACAGTACTg | 142 |
| | reporter | AS | RHO_68_Anti-sense | aattcAGTACTGTGGGTACTCGAAGTGGCTGCGTACCACACCCGTCc | 140 |
| RHO (1039) | Wild-type | S | RHO_WT_Sense | tcgagCGGAGACGAGCCAGGTGGCCCCGGCCTAAGACCTGCCTAGGg | 141 |
| | reporter | AS | RHO_WT_Anti-sense | aattcCCTAGGCAGGTCTTAGGCCGGGGCCACCTGGCTCGTCTCCGc | 143 |
| | Mutant | S | RHO_1039_Sense | tcgagCGGAGACGAGCCAGGTGGCCTCGGCCTAAGACCTGCCTAGGg | 144 |
| | reporter | AS | RHO_1039_Anti-sense | aattcCCTAGGCAGGTCTTAGGCCGAGGCCACCTGGCTCGTCTCCGc | 145 |
| SCNIA | Wild-type | S | SCN1A_WT_Sense | tcgagTGAGAACATTCAGAGTTCTCCGAGCATTGAAGACGATTTCAg | 146 |
| | reporter | AS | SCN1A_WT_Anti-sense | aattcTGAAATCGTCTTCAATGCTCGGAGAACTCTGAATGTTCTCAc | 147 |
| | Mutant | S | SCN1A_664_Sense | tcgagTGAGAACATTCAGAGTTCTCTGAGCATTGAAGACGATTTCAg | 148 |
| | reporter | AS | SCN1A_664_Anti-sense | aattcTGAAATCGTCTTCAATGCTCAGAGAACTCTGAATGTTCTCAc | 149 |

TABLE 2-continued

| Gene Name (Position of mutation) | Function | Strand | Name | Sequence | Seq. ID No. |
|---|---|---|---|---|---|
| APOB | Wild-type | S | APOB_WT_Sense | tcgagCTTGAATTCCAAGAGCACACGGTCTTCAGTGAAGCTGCAGGg | 150 |
| | reporter | AS | APOB_WT_Anti-sense | aattcCCTGCAGCTTCACTGAAGACCGTGTGCTCTTGGAATTCAAGc | 151 |
| | Mutant | S | APOB_10580_Sense | tcgagCTTGAATTCCAAGAGCACACAGTCTTCAGTGAAGCTGCAGGg | 152 |
| | reporter | AS | APOB_10580_Anti-sense | aattcCCTGCAGCTTCACTGAAGACTGTGTGCTCTTGGAATTCAAGc | 153 |
| F12 (CG) | Wild-type | S | F12_WT_Sense | tcgagACCGCCGAAGCCTCAGCCCACGACCCGGACCCCGCCTCAGTg | 154 |
| | reporter | AS | F12_WT_Anti-sense | aattcACTGAGGCGGGGTCCGGGTCGTGGGCTGAGGCTTCGGCGGTc | 155 |
| | Mutant | S | F12_983_CG_Sense | tcgagACCGCCGAAGCCTCAGCCCAGGACCCGGACCCCGCCTCAGTg | 156 |
| | reporter | AS | F12_983_CG_Anti-sense | aattcACTGAGGCGGGGTCCGGTCCTGGGCTGAGGCTTCGGCGGTCc | 157 |
| CLCN7 | Wild-type | S | CLCN7_WT_Sense | tcgagTGTTCCGGGCCCTGGGCCTGCGGCACCTGGTGGTGGTGGACg | 158 |
| | reporter | AS | CLCN7_WT_Anti-sense | aattcGTCCACCACCACCAGGTGCCGCAGGCCCAGGGCCCGGAACAc | 159 |
| | Mutant | S | CLCN7_2299_Sense | tcgagTGTTCCGGGCCCTGGGCCTGTGGCACCTGGTGGTGGTGGACg | 160 |
| | reporter | AS | CLCN7_2299_Anti-sense | aattcGTCCACCACCACCAGGTGCCACAGGCCCAGGGCCCGGAACAc | 161 |
| SCN8A | Wild-type | S | SCN8A_WT_Sense | tcgagTCCCCTCCATCATGAATGTGCTGCTGGTGTGTCTCATCTTCg | 162 |
| | reporter | AS | SCN8A_WT_Anti-sense | aattcGAAGATGAGACACACCAGCAGCACATTCATGATGGAGGGGAc | 163 |
| | Mutant | S | SCN8A_3991_Sense | tcgagTCCCCTCCATCATGAATGTGGTGCTGGTGTGTCTCATCTTCg | 164 |
| | reporter | AS | SCN8A_3991_Anti-sense | aattcGAAGATGAGACACACCAGCACCACATTCATGATGGAGGGGAc | 165 |
| PCSK9 | Wild-type | S | PCSK9_WT_Sense | tcgagACATCATTGGTGCCTCCAGCGACTGCAGCACCTGCTTTGTGg | 166 |
| | reporter | AS | PCSK9_WT_Anti-sense | aattcCACAAAGCAGGTGCTGCAGTCGCTGGAGGCACCAATGATGTc | 167 |
| | Mutant | S | PCSK9_1120_Sense | tcgagACATCATTGGTGCCTCCAGCTACTGCAGCACCTGCTTTGTGg | 168 |
| | reporter | AS | PCSK9_1120_Anti-sense | aattcCACAAAGCAGGTGCTGCAGTAGCTGGAGGCACCAATGATGTc | 169 |
| KRT6A | Wild-type | S | KRT6A_WT_Sense | tcgagTCAAGACCCTCAACAACAAGTTTGCCTCCTTCATCGACAAGg | 170 |
| | reporter | AS | KRT6A_WT_Anti-sense | aattcCTTGTCGATGAAGGAGGCAAACTTGTTGTTGAGGGTCTTGAc | 171 |
| | Mutant | S | KRT6A_520_Sense | tcgagTCAAGACCCTCAACAACAAGGTTGCCTCCTTCATCGACAAGg | 172 |
| | reporter | AS | KRT6A_520_Anti-sense | aattcCTTGTCGATGAAGGAGGCAACCTTGTTGTTGAGGGTCTTGAc | 173 |

For siRNAs, the base at position 11 of each gene corresponded to the position of the point mutation in the corresponding mutant allele, the group at the 2'-position of the pentose in each of the ribonucleotides at positions 6-8 of the siRNA's guide strand was replaced by $OCH_3$, and the base at position 6 of the guide strand was mismatched with that of the corresponding mutant allele. The 5'-ends of the guide and passenger strands of each siRNA were replaced as indicated in Table 3.

TABLE 3

| Gene Name (Position of mutation) | Base change at 5'-end of G strand | Base change at 5'-end of P strand |
|---|---|---|
| HTT (rs363125) | — | C→G |
| HTT (rs362307) | G→U | — |
| HTT (rs362331) | — | C→G |
| ATXN3 | G→U | A→G |
| ZMYM3 | A→U | U→G |
| CTNNB1 | G→U | — |
| SMARCA4 | C→U | — |
| SMO | C→G | — |
| AR | G→U | U→G |

TABLE 3-continued

| Gene Name (Position of mutation) | Base change at 5'-end of G strand | Base change at 5'-end of P strand |
|---|---|---|
| DNM2 | G→U | U→G |
| KRT14 | G→U | — |
| IL4R (223) | — | A→G |
| IL4R (1507) | — | U→G |
| MAPT | G→U | U→G |
| MS4A2 | A→U | C→G |
| PABPN1 | G→U | A→G |
| RHO(68) | G→U | A→G |
| RHO (1039) | — | A→G |
| SCNIA | — | — |
| APOB | C→U | — |
| F12 | G→U | U→G |
| CLCN7 | A→U | U→G |
| SCN8A | C→U | U→G |
| PCSK9 | G→U | C→G |
| KRT6A | A→U | A→G |

The reporters indicated in Table 2 were used for the corresponding genes, and reporter assays were performed using siRNAs indicated in Tables 4 and 5 using the aforementioned method.

TABLE 4

| Gene Name (Position of mutation) | Name | Strand | Sequence | Seq. ID No. |
|---|---|---|---|---|
| HTT | SiHTT_363125-WT | P | CCACAGUACUUCAACGCUAGA | 174 |
| (rs363125) | | G | UAGCGUUGAAGUACUGUGGGG | 175 |
| HTT | SiHTT_362307-WT | P | GAAGUCUGCGCCCUUGUGCCC | 176 |
| (rs362307) | | G | GCACAAGGGCGCAGACUUCCA | 177 |
| HTT | SiHTT_362331-WT | P | CCCUCAUCUACUGUGUGCACU | 178 |
| (rs362331) | | G | UGCACACAGUAGAUGAGGGAG | 179 |
| ATXN3 | SiATXN3-WT | P | AGCAGCAGGGGGACCUAUCAG | 180 |
| | | G | GAUAGGUCCCCCUGCUGCUGC | 181 |
| ZMYM3 | SiZMYM3_WT | P | UCCACUGGCGUGGGCAGAUCC | 182 |
| | | G | AUCUGCCCACGCCAGUGGAUG | 183 |
| CTNNB1 | siCTNNB1_WT | P | GUGCCACUACCACAGCUCCUU | 184 |
| | | G | GGAGCUGUGGUAGUGGCACCA | 185 |
| SMARCA4 | siSMARCA4_WT | P | GCUGCUGACGGGCACACCGCU | 186 |
| | | G | CGGUGUGCCCGUCAGCAGCAG | 187 |
| SMO | siSMO_WT | P | GCCUGGUGCUCAUCGUGGGAG | 188 |
| | | G | CCCACGAUGAGCACCAGGCCG | 189 |

TABLE 5

| Gene Name (Position of mutation) | Name | Strand | Sequence | Seq. ID No. |
|---|---|---|---|---|
| HTT | SiHTT_363125-SNP | P | GCACAGUAAUUCAUCGCUAGA | 190 |
| (rs363125) | | G | UAGCGAUGAAUUACUGUGCGG | 191 |
| HTT | SiHTT_362307-SNP | P | GAAGUCUGUGCCCAUGUGACC | 192 |
| (rs362307) | | G | UCACAUGGGCACAGACUUCCA | 193 |
| HTT | SiHTT_362331-SNP | P | GCCUCAUCCACUGAGUGCACU | 194 |
| (rs362331) | | G | UGCACUCAGUGGAUGAGGCAG | 195 |
| ATXN3 | SiATXN3-SNP | P | GGCAGCAGCGGGAGCUAUAAG | 196 |
| | | G | UAUAGCUCCCGCUGCUGCCGC | 197 |
| ZMYM3 | SiZMYM3_MUT_2206 | P | GCCACUGGUGUGGCCAGAACC | 198 |
| | | G | UUCUGGCCACACCAGUGGCUG | 199 |

TABLE 5-continued

| Gene Name (Position of mutation) | Name | Strand | Sequence | Seq. ID No. |
|---|---|---|---|---|
| CTNNB1 | SiCTNNB1_MUT_121 | P | GUGCCACUGCCACUGCUCAUU | 200 |
| | | G | UGAGCAGUGGCAGUGGCACCA | 201 |
| SMARCA4 | SiSMARCA4_MUT_2729 | P | GCUGCUGAUGGGCUCACCACU | 202 |
| | | G | UGGUGAGCCCAUCAGCAGCAG | 203 |
| SMO | siSMO_MUT_1234 | P | GCCUGGUGUUCAUGGUGGAAG | 204 |
| | | G | GCCACCAUGAACACCAGGCCG | 205 |
| AR | SiAR_MUT_2180 | P | GGGCUUCCUCAACAUACAAGU | 206 |
| | | G | UUGUAUGUUGAGGAAGCCCGG | 207 |
| DNM2 | siDNM2_MUT_1102 | P | GCUUCCACAAGCGCUUCCAAU | 208 |
| | | G | UGGAAGCGCUUGUGGAAGCUG | 209 |
| KRT14 | SiKRT14_MUT_1151 | P | GGAGCAGCCGGCCGAGCUACG | 210 |
| | | G | UAGCUCGGCCGGCUGCUCCUC | 211 |
| IL4R (223) | SiILR4_MUT_223 | P | GCACGUGUGUCCCAGAGAACA | 212 |
| | | G | UUCUCUGGGACACACGUGCGG | 213 |
| IL4R (1507) | SiILR4_MUT_1507 | P | GCAGCAACCCCCUCAGCCAGU | 214 |
| | | G | UGGCUGAGGGGGUUGCUGCAG | 215 |
| MAPT (1853) | siMAPT_MUT_1853 | P | GCACGUCCUGGGACGCGGAAG | 216 |
| | | G | UCCGCGUCCCAGGACGUGCUU | 217 |
| MS4A2 | siMS4A2_MUT_710 | P | GCCAGGGGGAAUGACUCCACC | 218 |
| | | G | UGGAGUCAUUCCCCCUGGCUC | 219 |
| PABPN1 | siPABPN1_MUT_35 | P | GGCAGCGGCGGCUCCGGGAGG | 220 |
| | | G | UCCCGGAGCCGCCGCUGCCGC | 221 |
| RHO (68) | siRHO_MUT_68 | P | GCGCAGCCACUUCCAGUAACC | 222 |
| | | G | UUACUGGAAGUGGCUGCGCAC | 223 |
| RHO (1039) | SiRHO_MUT_1039 | P | GGGUGGCCUCGGCGUAAGACC | 224 |
| | | G | UCUUACGCCGAGGCCACCCGG | 225 |
| SCNIA | siSCN1A_MUT_664 | P | GAGUUCUCUGAGCUUUGAAGA | 226 |
| | | G | UUCAAAGCUCAGAGAACUCUG | 227 |
| APOB | siAPOB_MUT_10580 | P | GAGCACACAGUCUACAGUAAA | 228 |
| | | G | UACUGUAGACUGUGUGCUCUU | 229 |
| F12 (983 CG) | siF12_MUT_983 CG | P | GCAGCCCAGGACCGGGACACC | 230 |
| | | G | UGUCCCGGUCCUGGGCUGCGG | 231 |
| CLCN7 | siCLCN7_MUT_2299 | P | GGACCCGGACGCCGUGGACCA | 323 |
| | | G | UCCAGCUGCCACAGGCCCCGG | 233 |
| SCN8A | siSCN8A_MUT_3991 | P | GGAAUGUGGUGCUCGUGUAUC | 234 |
| | | G | UACACGAGCACCACAUUCCUG | 235 |
| PCSK9 | siPCSK9_MUT_1120 | P | GCUCCAGCUACUGGAGCAACU | 236 |
| | | G | UUGCUCCAGUAGCUGGAGCCA | 237 |
| KRT6A | SiKRT6A_MUT_520 | P | GCAACAAGGUUGCGUCCUACA | 238 |
| | | G | UAGGACGCAACCUUGUUGCUG | 239 |

FIGS. 11 to 35 show the results of the assays. For all genes, the siRNAs suppressed the expressions of the mutant alleles in a concentration-dependent manner, though the expressions of the wild-type alleles were hardly suppressed.

Industrial Applicability

The present invention allowed to provide novel RNA molecules, novel chimeric NA molecules, novel double-stranded RNA molecules, and novel double-stranded chimeric NA molecules.

The invention claimed is:

1. An RNA molecule that targets a mutant allele of a gene, the mutant allele having a point mutation relative to a wild-type allele of the gene, wherein the gene is selected from the group consisting of HTT, ATXN3, ZMYM3, CTNNB1, SMARCA4, SMO, AR, DNM2, KRT14, IL4R, MAPT, MS4A2, PABPN1, RHO, SCN1A, APOB, F12, CLCN7, SCN8A, PCSK9, and KRT6A, and wherein the RNA molecule satisfies the followings:

(1) the molecule has a nucleotide sequence complementary to a nucleotide sequence of a coding region of the mutant allele except for a base specified in (2-1) below; and (2) when counted from the base at the 5'-end of a nucleotide sequence complementary to the nucleotide sequence of the mutant allele, (2-1) a base at position 5 or 6 is mismatched with a base in the mutant allele;

(2-2) a base at position 10 or 11 is at the position of the point mutation and is identical to the base at the position of the point mutation in the mutant allele; and (2-3) the group at the 2'-position of the pentose in each of ribonucleotides at positions 6-8 or positions 7 and 8 is independently modified with $OCH_3$, halogen, or LNA.

2. The RNA molecule according to claim 1, wherein the halogen is fluorine.

3. The RNA molecule according to claim 1, wherein, when the base at the 5'-end of the nucleotide sequence specified in (1) is cytosine or guanine, the base is replaced by adenine or uracil.

4. The RNA molecule according to claim 1, wherein, when the base at the 3'-end of the nucleotide sequence specified in (1) is adenine or uracil, it is replaced by cytosine or guanine.

5. The RNA molecule according to claim 1, wherein the RNA molecule comprises 13-28 nucleotides.

6. The RNA molecule according to claim 1, further comprising 1-3 nucleotide(s) at the 3'-end of the nucleotide sequence specified in (1).

7. A chimeric NA molecule that targets a mutant allele of a gene, wherein the mutant allele has a point mutation relative to a wild-type allele of the gene, wherein the gene is selected from the group consisting of HTT, ATXN3, ZMYM3, CTNNB1, SMARCA4, SMO, AR, DNM2, KRT14, IL4R, MAPT, MS4A2, PABPN1, RHO, SCN1A, APOB, F12, CLCN7, SCN8A, PCSK9, and KRT6A, and wherein the chimeric NA molecule satisfies the following:

(1) the chimeric NA molecule has a nucleotide sequence complementary to a nucleotide sequence of a coding region of the mutant allele except for a base specified in (2-1) below; and (2) when counted from the base at the 5'-end of a nucleotide sequence complementary to the nucleotide sequence of the mutant allele, (2-1) a base at position 5 or 6 is mismatched with a base in the mutant allele;

(2-2) a base at position 10 or 11 is at the position of the point mutation and is identical to the base at the position of the point mutation in the mutant allele; and (2-3) the group at the 2'-position of the pentose in each of ribonucleotides at positions 6-8 or positions 7 and 8 is independently modified with $OCH_3$, halogen, or LNA, wherein the chimeric NA molecule comprises a ribonucleotide as well as a deoxyribonucleotide, an artificial nucleic acid, or a nucleic acid analog.

8. A double-stranded RNA molecule that targets a mutant allele of a gene, wherein the mutant allele has a point mutation relative to a wild-type allele of the gene, the double-stranded RNA molecule comprising a guide strand and a passenger strand, wherein the gene is selected from the group consisting of HTT, ATXN3, ZMYM3, CTNNB1, SMARCA4, SMO, AR, DNM2, KRT14, IL4R, MAPT, MS4A2, PABPN1, RHO, SCN1A, APOB, F12, CLCN7, SCN8A, PCSK9, and KRT6A, and wherein the guide strand satisfies the following:

(1) the guide strand has a nucleotide sequence complementary to a nucleotide sequence of a coding region of the mutant allele except for a base specified in (2-1) below; and (2) when counted from the base at the 5'-end of a nucleotide sequence complementary to the nucleotide sequence of the mutant allele, (2-1) a base at position 5 or 6 is mismatched with a base in the mutant allele;

(2-2) a base at position 10 or 11 is at the position of the point mutation and is identical to the base at the position of the point mutation in the mutant allele; and (2-3) the group at the 2'-position of the pentose in each of ribonucleotides at positions 6-8 or positions 7 and 8 is independently modified with $OCH_3$, halogen, or LNA.

9. The double-stranded RNA molecule according to claim 8, wherein the RNA molecule comprises an overhang at the 3'-end of the guide strand and/or an overhang at the 3'-end of the passenger strand.

10. The double-stranded RNA molecule according to claim 9, wherein either or both of the overhangs comprise 1-3 nucleotides.

11. A double-stranded chimeric NA molecule that targets a mutant allele of a gene, the mutant allele having a point mutation relative to a wild-type allele of the gene, the double-stranded RNA molecule comprising a guide strand and a passenger strand, the double-stranded chimeric NA molecule comprising a ribonucleotide as well as a deoxyribonucleotide, an artificial nucleic acid, or a nucleic acid analog, wherein the gene is selected from the group consisting of HTT, ATXN3, ZMYM3, CTNNB1, SMARCA4, SMO, AR, DNM2, KRT14, IL4R, MAPT, MS4A2, PABPN1, RHO, SCN1A, APOB, F12, CLCN7, SCN8A, PCSK9, and KRT6A, and wherein the guide strand satisfies the followings:

(1) the guide strand has a nucleotide sequence complementary to a nucleotide sequence of a coding region of the mutant allele except for a base specified in (2-1) below; and (2) when counted from the base at the 5'-end of a nucleotide sequence complementary to the nucleotide sequence of the mutant allele, (2-1) a base at position 5 or 6 is mismatched with a base in the mutant allele;

(2-2) a base at position 10 or 11 is at the position of the point mutation and is identical to the base at the position of the point mutation in the mutant allele; and (2-3) the group at the 2'-position of the pentose in each of ribonucleotides at positions 6-8 or positions 7 and 8 is independently modified with $OCH_3$, halogen, or LNA.

12. A method for performing RNA interference to target a mutant allele of a gene in a cell containing a wild-type allele of the gene and the mutant allele, wherein the mutant allele has a point mutation, the method comprising the step of:

introducing the RNA molecule of claim 1 into the cell.

13. A method for performing RNA interference to target a mutant allele of a gene in a cell containing a wild-type allele of the gene and the mutant allele, wherein the mutant allele has a point mutation relative to the wild-type allele, the method comprising the step of:

introducing the chimeric NA molecule of claim 7 into the cell.

14. A method for performing RNA interference to target a mutant allele of a gene in a cell containing a wild-type allele of the gene and the mutant allele, wherein the mutant allele has a point mutation relative to the wild-type allele, the method comprising the step of:

introducing the double-stranded RNA molecule of claim 8 into the cell.

15. A method for performing RNA interference to target a mutant allele of a gene in a cell containing a wild-type allele of the gene and the mutant allele, wherein the mutant allele has a point mutation relative to the wild-type allele, the method comprising the step of:

introducing the double-stranded chimeric NA molecule of claim 11 into the cell.

* * * * *

SEQUENCE LISTING

<160> NUMBER OF SEQ ID NOS: 239

<210> SEQ ID NO 1
<211> LENGTH: 21
<212> TYPE: RNA
<213> ORGANISM: Artificial Sequence
<220> FEATURE:
<223> OTHER INFORMATION: siRNA forward

<400> SEQUENCE: 1
gggagcugau ggccuaggaa a 21

<210> SEQ ID NO 2
<211> LENGTH: 21
<212> TYPE: RNA
<213> ORGANISM: Artificial Sequence
<220> FEATURE:
<223> OTHER INFORMATION: (6)...(8) 2'-O-methyl-modified

<400> SEQUENCE: 2
uccuaggcca ucagcuccca c 21

<210> SEQ ID NO 3
<211> LENGTH: 21
<212> TYPE: RNA
<213> ORGANISM: Artificial Sequence
<220> FEATURE:
<223> OTHER INFORMATION: (6) and (8) 2'-O-methyl-modified

<400> SEQUENCE: 3
uccuaggcca ucagcuccca c 21

<210> SEQ ID NO 4
<211> LENGTH: 33
<212> TYPE: DNA
<213> ORGANISM: Artificial Sequence
<220> FEATURE:
<223> OTHER INFORMATION: reporter forward

<400> SEQUENCE: 4
tggtagttgg agctggtggc gtaggcaaga gtg 33

<210> SEQ ID NO 5
<211> LENGTH: 33
<212> TYPE: DNA
<213> ORGANISM: Artificial Sequence
<220> FEATURE:
<223> OTHER INFORMATION: reporter reverse

<400> SEQUENCE: 5
cactcttgcc tacgccacca gctccaacta cca 33

<210> SEQ ID NO 6
<211> LENGTH: 33
<212> TYPE: DNA
<213> ORGANISM: Artificial Sequence
<220> FEATURE:
<223> OTHER INFORMATION: reporter forward

<400> SEQUENCE: 6
tggtagttgg agctgatggc gtaggcaaga gtg 33

<210> SEQ ID NO 7
<211> LENGTH: 33
<212> TYPE: DNA
<213> ORGANISM: Artificial Sequence -continued
<220> FEATURE:
<223> OTHER INFORMATION: reporter reverse

<400> SEQUENCE: 7
cactcttgcc tacgccatca gctccaacta cca 33

<210> SEQ ID NO 8
<211> LENGTH: 21
<212> TYPE: DNA
<213> ORGANISM: Artificial Sequence
<220> FEATURE:
<223> OTHER INFORMATION: siRNA forward

<400> SEQUENCE: 8
guuggagcug auggcguagt t 21

<210> SEQ ID NO 9
<211> LENGTH: 21
<212> TYPE: DNA
<213> ORGANISM: Artificial Sequence
<220> FEATURE:
<223> OTHER INFORMATION: siRNA reverse

<400> SEQUENCE: 9
cuacgccauc agcuccaact t 21

<210> SEQ ID NO 10
<211> LENGTH: 21
<212> TYPE: RNA
<213> ORGANISM: Artificial Sequence
<220> FEATURE:
<223> OTHER INFORMATION: siRNA forward

<400> SEQUENCE: 10
uuggagcuga uggcguaggc a 21

<210> SEQ ID NO 11
<211> LENGTH: 21
<212> TYPE: RNA
<213> ORGANISM: Artificial Sequence
<220> FEATURE:
<223> OTHER INFORMATION: siRNA reverse

<400> SEQUENCE: 11
ccuacgccau cagcuccaac u 21

<210> SEQ ID NO 12
<211> LENGTH: 21
<212> TYPE: RNA
<213> ORGANISM: Artificial Sequence
<220> FEATURE:
<223> OTHER INFORMATION: siRNA forward

<400> SEQUENCE: 12
uggagcugau ggcguaggca a 21

<210> SEQ ID NO 13
<211> LENGTH: 21
<212> TYPE: RNA
<213> ORGANISM: Artificial Sequence
<220> FEATURE:
<223> OTHER INFORMATION: siRNA reverse

<400> SEQUENCE: 13
gccuacgcca ucagcuccaa c 21

<210> SEQ ID NO 14
<211> LENGTH: 21
<212> TYPE: RNA
<213> ORGANISM: Artificial Sequence
<220> FEATURE:
<223> OTHER INFORMATION: siRNA forward

<400> SEQUENCE: 14
gggagcugau ggcguaggaa a 21

<210> SEQ ID NO 15
<211> LENGTH: 21
<212> TYPE: RNA
<213> ORGANISM: Artificial Sequence
<220> FEATURE:
<223> OTHER INFORMATION: siRNA reverse

<400> SEQUENCE: 15
uccuacgcca ucagcuccca c 21

<210> SEQ ID NO 16
<211> LENGTH: 21
<212> TYPE: RNA
<213> ORGANISM: Artificial Sequence
<220> FEATURE:
<223> OTHER INFORMATION: siRNA forward

<400> SEQUENCE: 16
gggagcugau ggcguaggaa a 21

<210> SEQ ID NO 17
<211> LENGTH: 21
<212> TYPE: RNA
<213> ORGANISM: Artificial Sequence
<220> FEATURE:
<223> OTHER INFORMATION: siRNA reverse
(2)...(5) 2'-O-methyl modified

<400> SEQUENCE: 17
uccuacgcca ucagcuccca c 21

<210> SEQ ID NO 18
<211> LENGTH: 21
<212> TYPE: RNA
<213> ORGANISM: Artificial Sequence
<220> FEATURE:
<223> OTHER INFORMATION: siRNA forward

<400> SEQUENCE: 18
gggagcugau ggcguaggaa a 21

<210> SEQ ID NO 19
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 19
uccuacgcca ucagcuccca c 21

<210> SEQ ID NO 20
<211> LENGTH: 21
<212> TYPE: RNA
<213> ORGANISM: Artificial Sequence
<220> FEATURE:
<223> OTHER INFORMATION: siRNA forward

<400> SEQUENCE: 20
gggagcugau ggcguacgaa a 21

<210> SEQ ID NO 21
<211> LENGTH: 21
<212> TYPE: RNA
<213> ORGANISM: Artificial Sequence
<220> FEATURE:
<223> OTHER INFORMATION: siRNA reverse

<400> SEQUENCE: 21
ucguacgcca ucagcuccca c 21

<210> SEQ ID NO 22
<211> LENGTH: 21
<212> TYPE: RNA
<213> ORGANISM: Artificial Sequence
<220> FEATURE:
<223> OTHER INFORMATION: siRNA forward

<400> SEQUENCE: 22
gggagcugau ggcguuggaa a 21

<210> SEQ ID NO 23
<211> LENGTH: 21
<212> TYPE: RNA
<213> ORGANISM: Artificial Sequence
<220> FEATURE:
<223> OTHER INFORMATION: siRNA reverse

<400> SEQUENCE: 23
uccaacgcca ucagcuccca c 21

<210> SEQ ID NO 24
<211> LENGTH: 21
<212> TYPE: RNA
<213> ORGANISM: Artificial Sequence
<220> FEATURE:
<223> OTHER INFORMATION: siRNA forward

<400> SEQUENCE: 24
gggagcugau ggcgaaggaa a 21

<210> SEQ ID NO 25
<211> LENGTH: 21
<212> TYPE: RNA
<213> ORGANISM: Artificial Sequence
<220> FEATURE:
<223> OTHER INFORMATION: siRNA reverse

<400> SEQUENCE: 25
uccuucgcca ucagcuccca c 21

<210> SEQ ID NO 26
<211> LENGTH: 21
<212> TYPE: RNA
<213> ORGANISM: Artificial Sequence
<220> FEATURE:
<223> OTHER INFORMATION: siRNA forward

<400> SEQUENCE: 26
gggagcugau ggccuaggaa a 21

<210> SEQ ID NO 27
<211> LENGTH: 21
<212> TYPE: RNA
<213> ORGANISM: Artificial Sequence
<220> FEATURE:
<223> OTHER INFORMATION: siRNA reverse

<400> SEQUENCE: 27
uccuaggcca ucagcuccca c 21

<210> SEQ ID NO 28
<211> LENGTH: 21
<212> TYPE: RNA
<213> ORGANISM: Artificial Sequence
<220> FEATURE:
<223> OTHER INFORMATION: siRNA forward

<400> SEQUENCE: 28
gggagcugau gggguaggaa a 21

<210> SEQ ID NO 29
<211> LENGTH: 21
<212> TYPE: RNA
<213> ORGANISM: Artificial Sequence
<220> FEATURE:
<223> OTHER INFORMATION: siRNA reverse

<400> SEQUENCE: 29
uccuacccca ucagcuccca c 21

<210> SEQ ID NO 30
<211> LENGTH: 21
<212> TYPE: RNA
<213> ORGANISM: Artificial Sequence
<220> FEATURE:
<223> OTHER INFORMATION: siRNA forward

<400> SEQUENCE: 30
gggagcugau ggcguacgaa a 21

<210> SEQ ID NO 31
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 31
ucguacgcca ucagcuccca c 21

<210> SEQ ID NO 32
<211> LENGTH: 21
<212> TYPE: RNA
<213> ORGANISM: Artificial Sequence
<220> FEATURE:
<223> OTHER INFORMATION: siRNA forward

<400> SEQUENCE: 32
gggagcugau ggcguuggaa a 21

<210> SEQ ID NO 33
<211> LENGTH: 21
<212> TYPE: RNA
<213> ORGANISM: Artificial Sequence
<220> FEATURE:

```
<223> OTHER INFORMATION: siRNA reverse
      (6)...(8) 2'-O-methly modified

<400> SEQUENCE: 33

uccaacgcca ucagcuccca c                                             21


<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34

gggagcugau ggcgaaggaa a                                             21


<210> SEQ ID NO 35
<211> LENGTH: 21
<212> TYPE: RNA
<213> ORGANISM: Artificial Sequence
<220> FEATURE:
<223> OTHER INFORMATION: siRNA reverse
      (6)...(8) 2'-O-methyl modified

<400> SEQUENCE: 35

uccuucgcca ucagcuccca c                                             21


<210> SEQ ID NO 36
<211> LENGTH: 21
<212> TYPE: RNA
<213> ORGANISM: Artificial Sequence
<220> FEATURE:
<223> OTHER INFORMATION: siRNA forward

<400> SEQUENCE: 36

gggagcugau ggccuaggaa a                                             21


<210> SEQ ID NO 37
<211> LENGTH: 21
<212> TYPE: RNA
<213> ORGANISM: Artificial Sequence
<220> FEATURE:
<223> OTHER INFORMATION: siRNA reverse
      (6)...(8) 2'-O-methyl modified

<400> SEQUENCE: 37

uccuaggcca ucagcuccca c                                             21


<210> SEQ ID NO 38
<211> LENGTH: 21
<212> TYPE: RNA
<213> ORGANISM: Artificial Sequence
<220> FEATURE:
<223> OTHER INFORMATION: siRNA forward

<400> SEQUENCE: 38

gggagcugau gggguaggaa a                                             21


<210> SEQ ID NO 39
<211> LENGTH: 21
<212> TYPE: RNA
<213> ORGANISM: Artificial Sequence
<220> FEATURE:
<223> OTHER INFORMATION: siRNA reverse
      (6)...(8) 2'-O-methyl modified

<400> SEQUENCE: 39
```

uccuacccca ucagcuccca c 21

<210> SEQ ID NO 40
<211> LENGTH: 33
<212> TYPE: DNA
<213> ORGANISM: Artificial Sequence
<220> FEATURE:
<223> OTHER INFORMATION: reporter forward

<400> SEQUENCE: 40
tggtagttgg agctgttggc gtaggcaaga gtg 33

<210> SEQ ID NO 41
<211> LENGTH: 33
<212> TYPE: DNA
<213> ORGANISM: Artificial Sequence
<220> FEATURE:
<223> OTHER INFORMATION: reporter reverse

<400> SEQUENCE: 41
cactcttgcc tacgccaaca gctccaacta cca 33

<210> SEQ ID NO 42
<211> LENGTH: 33
<212> TYPE: DNA
<213> ORGANISM: Artificial Sequence
<220> FEATURE:
<223> OTHER INFORMATION: reporter forward

<400> SEQUENCE: 42
tggtagttgg agctgctggc gtaggcaaga gtg 33

<210> SEQ ID NO 43
<211> LENGTH: 33
<212> TYPE: DNA
<213> ORGANISM: Artificial Sequence
<220> FEATURE:
<223> OTHER INFORMATION: reporter reverse

<400> SEQUENCE: 43
cactcttgcc tacgccagca gctccaacta cca 33

<210> SEQ ID NO 44
<211> LENGTH: 21
<212> TYPE: RNA
<213> ORGANISM: Artificial Sequence
<220> FEATURE:
<223> OTHER INFORMATION: siRNA forward

<400> SEQUENCE: 44
gggagcuguu ggcguaggaa a 21

<210> SEQ ID NO 45
<211> LENGTH: 21
<212> TYPE: RNA
<213> ORGANISM: Artificial Sequence
<220> FEATURE:
<223> OTHER INFORMATION: siRNA reverse

<400> SEQUENCE: 45
uccuacgcca acagcuccca c 21

<210> SEQ ID NO 46
<211> LENGTH: 21
<212> TYPE: RNA

<213> ORGANISM: Artificial Sequence
<220> FEATURE:
<223> OTHER INFORMATION: siRNA forward

<400> SEQUENCE: 46
gggagcuguu ggcgaaggaa a 21

<210> SEQ ID NO 47
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 47
uccuucgcca acagcuccca c 21

<210> SEQ ID NO 48
<211> LENGTH: 21
<212> TYPE: RNA
<213> ORGANISM: Artificial Sequence
<220> FEATURE:
<223> OTHER INFORMATION: siRNA forward

<400> SEQUENCE: 48
gggagcuguu ggccuaggaa a 21

<210> SEQ ID NO 49
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 49
uccuaggcca acagcuccca c 21

<210> SEQ ID NO 50
<211> LENGTH: 21
<212> TYPE: RNA
<213> ORGANISM: Artificial Sequence
<220> FEATURE:
<223> OTHER INFORMATION: siRNA forward

<400> SEQUENCE: 50
gggagcugcu ggcguaggaa a 21

<210> SEQ ID NO 51
<211> LENGTH: 21
<212> TYPE: RNA
<213> ORGANISM: Artificial Sequence
<220> FEATURE:
<223> OTHER INFORMATION: siRNA reverse

<400> SEQUENCE: 51
uccuacgcca gcagcuccca c 21

<210> SEQ ID NO 52
<211> LENGTH: 21
<212> TYPE: RNA
<213> ORGANISM: Artificial Sequence
<220> FEATURE:
<223> OTHER INFORMATION: siRNA forward

<400> SEQUENCE: 52

-continued gggagcugcu ggcgaaggaa a 21

<210> SEQ ID NO 53
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 53
uccuucgcca gcagcuccca c 21

<210> SEQ ID NO 54
<211> LENGTH: 21
<212> TYPE: RNA
<213> ORGANISM: Artificial Sequence
<220> FEATURE:
<223> OTHER INFORMATION: siRNA forward

<400> SEQUENCE: 54
gggagcugcu ggccuaggaa a 21

<210> SEQ ID NO 55
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 55
uccuaggcca gcagcuccca c 21

<210> SEQ ID NO 56
<211> LENGTH: 40
<212> TYPE: DNA
<213> ORGANISM: Artificial Sequence
<220> FEATURE:
<223> OTHER INFORMATION: reporter forward

<400> SEQUENCE: 56
actggtggtg gttggagcag gtggtgttgg gaaaagcgca 40

<210> SEQ ID NO 57
<211> LENGTH: 40
<212> TYPE: DNA
<213> ORGANISM: Artificial Sequence
<220> FEATURE:
<223> OTHER INFORMATION: reporter reverse

<400> SEQUENCE: 57
tgcgcttttc ccaacaccac cagctccaac caccaccagt 40

<210> SEQ ID NO 58
<211> LENGTH: 40
<212> TYPE: DNA
<213> ORGANISM: Artificial Sequence
<220> FEATURE:
<223> OTHER INFORMATION: reporter forward

<400> SEQUENCE: 58
actggtggtg gttggagcag atggtgttgg gaaaagcgca 40

<210> SEQ ID NO 59

<211> LENGTH: 40
<212> TYPE: DNA
<213> ORGANISM: Artificial Sequence
<220> FEATURE:
<223> OTHER INFORMATION: reporter reverse

<400> SEQUENCE: 59
tgcgcttttc ccaacaccat cagctccaac caccaccagt 40

<210> SEQ ID NO 60
<211> LENGTH: 21
<212> TYPE: RNA
<213> ORGANISM: Artificial Sequence
<220> FEATURE:
<223> OTHER INFORMATION: siRNA forward

<400> SEQUENCE: 60
uggagcaggu gguguuggga a 21

<210> SEQ ID NO 61
<211> LENGTH: 21
<212> TYPE: RNA
<213> ORGANISM: Artificial Sequence
<220> FEATURE:
<223> OTHER INFORMATION: siRNA reverse

<400> SEQUENCE: 61
cccaacacca ccugcuccaa c 21

<210> SEQ ID NO 62
<211> LENGTH: 21
<212> TYPE: RNA
<213> ORGANISM: Artificial Sequence
<220> FEATURE:
<223> OTHER INFORMATION: siRNA forward

<400> SEQUENCE: 62
uggagcagau gguguuggga a 21

<210> SEQ ID NO 63
<211> LENGTH: 21
<212> TYPE: RNA
<213> ORGANISM: Artificial Sequence
<220> FEATURE:
<223> OTHER INFORMATION: siRNA reverse

<400> SEQUENCE: 63
cccaacacca ucugcuccaa c 21

<210> SEQ ID NO 64
<211> LENGTH: 21
<212> TYPE: RNA
<213> ORGANISM: Artificial Sequence
<220> FEATURE:
<223> OTHER INFORMATION: siRNA forward

<400> SEQUENCE: 64
cggagcagau ggugauggaa a 21

<210> SEQ ID NO 65
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 65
uccaucacca ucugcuccga c 21

<210> SEQ ID NO 66
<211> LENGTH: 38
<212> TYPE: DNA
<213> ORGANISM: Artificial Sequence
<220> FEATURE:
<223> OTHER INFORMATION: reporter forward

<400> SEQUENCE: 66
catactggat acagctggac aagaagagta cagtgcca 38

<210> SEQ ID NO 67
<211> LENGTH: 38
<212> TYPE: DNA
<213> ORGANISM: Artificial Sequence
<220> FEATURE:
<223> OTHER INFORMATION: reporter reverse

<400> SEQUENCE: 67
tggcactgta ctcttcttgt ccagctgtat ccagtatg 38

<210> SEQ ID NO 68
<211> LENGTH: 38
<212> TYPE: DNA
<213> ORGANISM: Artificial Sequence
<220> FEATURE:
<223> OTHER INFORMATION: reporter forward

<400> SEQUENCE: 68
catactggat acagctggac gagaagagta cagtgcca 38

<210> SEQ ID NO 69
<211> LENGTH: 38
<212> TYPE: DNA
<213> ORGANISM: Artificial Sequence
<220> FEATURE:
<223> OTHER INFORMATION: reporter reverse

<400> SEQUENCE: 69
tggcactgta ctcttctcgt ccagctgtat ccagtatg 38

<210> SEQ ID NO 70
<211> LENGTH: 21
<212> TYPE: RNA
<213> ORGANISM: Artificial Sequence
<220> FEATURE:
<223> OTHER INFORMATION: siRNA forward

<400> SEQUENCE: 70
agcuggacaa gaagaguaca g 21

<210> SEQ ID NO 71
<211> LENGTH: 21
<212> TYPE: RNA
<213> ORGANISM: Artificial Sequence
<220> FEATURE:
<223> OTHER INFORMATION: siRNA reverse

<400> SEQUENCE: 71
guacucuucu uguccagcug u 21

<210> SEQ ID NO 72
<211> LENGTH: 21

<212> TYPE: RNA
<213> ORGANISM: Artificial Sequence
<220> FEATURE:
<223> OTHER INFORMATION: siRNA forward

<400> SEQUENCE: 72
agcuggacga gaagaguaca g 21

<210> SEQ ID NO 73
<211> LENGTH: 21
<212> TYPE: RNA
<213> ORGANISM: Artificial Sequence
<220> FEATURE:
<223> OTHER INFORMATION: siRNA reverse

<400> SEQUENCE: 73
guacucuucu cguccagcug u 21

<210> SEQ ID NO 74
<211> LENGTH: 21
<212> TYPE: RNA
<213> ORGANISM: Artificial Sequence
<220> FEATURE:
<223> OTHER INFORMATION: siRNA forward

<400> SEQUENCE: 74
ggcuggacga gaaguguaaa g 21

<210> SEQ ID NO 75
<211> LENGTH: 21
<212> TYPE: RNA
<213> ORGANISM: Artificial Sequence
<220> FEATURE:
<223> OTHER INFORMATION: siRNA reverse
(6)...(8) 2'-O-methyl modified

<400> SEQUENCE: 75
uuacacuucu cguccagccg u 21

<210> SEQ ID NO 76
<211> LENGTH: 47
<212> TYPE: DNA
<213> ORGANISM: Artificial Sequence
<220> FEATURE:
<223> OTHER INFORMATION: reporter sense strand

<400> SEQUENCE: 76
tcgaggttaa gagatcccca cagtacttca acgctagaag aacacag 47

<210> SEQ ID NO 77
<211> LENGTH: 47
<212> TYPE: DNA
<213> ORGANISM: Artificial Sequence
<220> FEATURE:
<223> OTHER INFORMATION: reporter antisense strand

<400> SEQUENCE: 77
aattctgtgt tcttctagcg ttgaagtact gtggggatct cttaacc 47

<210> SEQ ID NO 78
<211> LENGTH: 47
<212> TYPE: DNA
<213> ORGANISM: Artificial Sequence
<220> FEATURE:
<223> OTHER INFORMATION: reporter sense strand

<400> SEQUENCE: 78
tcgaggttaa gagatcccca cagtaattca acgctagaag aacacag 47

<210> SEQ ID NO 79
<211> LENGTH: 47
<212> TYPE: DNA
<213> ORGANISM: Artificial Sequence
<220> FEATURE:
<223> OTHER INFORMATION: reporter antisense strand

<400> SEQUENCE: 79
aattctgtgt tcttctagcg ttgaattact gtggggatct cttaacc 47

<210> SEQ ID NO 80
<211> LENGTH: 47
<212> TYPE: DNA
<213> ORGANISM: Artificial Sequence
<220> FEATURE:
<223> OTHER INFORMATION: reporter sense strand

<400> SEQUENCE: 80
tcgagccgga gcctttggaa gtctgcgccc ttgtgccctg cctccag 47

<210> SEQ ID NO 81
<211> LENGTH: 47
<212> TYPE: DNA
<213> ORGANISM: Artificial Sequence
<220> FEATURE:
<223> OTHER INFORMATION: reporter antisense strand

<400> SEQUENCE: 81
aattctggag gcagggcaca agggcgcaga cttccaaagg ctccggc 47

<210> SEQ ID NO 82
<211> LENGTH: 47
<212> TYPE: DNA
<213> ORGANISM: Artificial Sequence
<220> FEATURE:
<223> OTHER INFORMATION: reporter sense strand

<400> SEQUENCE: 82
tcgagccgga gcctttggaa gtctgtgccc ttgtgccctg cctccag 47

<210> SEQ ID NO 83
<211> LENGTH: 47
<212> TYPE: DNA
<213> ORGANISM: Artificial Sequence
<220> FEATURE:
<223> OTHER INFORMATION: reporter antisense strand

<400> SEQUENCE: 83
aattctggag gcagggcaca agggcacaga cttccaaagg ctccggc 47

<210> SEQ ID NO 84
<211> LENGTH: 47
<212> TYPE: DNA
<213> ORGANISM: Artificial Sequence
<220> FEATURE:
<223> OTHER INFORMATION: reporter sense strand

<400> SEQUENCE: 84
tcgagcccac gcctgctccc tcatctactg tgtgcacttc atcctgg 47

<210> SEQ ID NO 85
<211> LENGTH: 47
<212> TYPE: DNA

<213> ORGANISM: Artificial Sequence
<220> FEATURE:
<223> OTHER INFORMATION: reporter antisense strand

<400> SEQUENCE: 85
aattccagga tgaagtgcac acagtagatg agggagcagg cgtgggc 47

<210> SEQ ID NO 86
<211> LENGTH: 47
<212> TYPE: DNA
<213> ORGANISM: Artificial Sequence
<220> FEATURE:
<223> OTHER INFORMATION: reporter sense strand

<400> SEQUENCE: 86
tcgagcccac gcctgctccc tcatccactg tgtgcacttc atcctgg 47

<210> SEQ ID NO 87
<211> LENGTH: 47
<212> TYPE: DNA
<213> ORGANISM: Artificial Sequence
<220> FEATURE:
<223> OTHER INFORMATION: reporter antisense strand

<400> SEQUENCE: 87
aattccagga tgaagtgcac acagtggatg agggagcagg cgtgggc 47

<210> SEQ ID NO 88
<211> LENGTH: 47
<212> TYPE: DNA
<213> ORGANISM: Artificial Sequence
<220> FEATURE:
<223> OTHER INFORMATION: reporter sense strand

<400> SEQUENCE: 88
tcgagagcag cagcagcagc agcaggggga cctatcagga cagagtg 47

<210> SEQ ID NO 89
<211> LENGTH: 47
<212> TYPE: DNA
<213> ORGANISM: Artificial Sequence
<220> FEATURE:
<223> OTHER INFORMATION: reporter antisense strand

<400> SEQUENCE: 89
aattcactct gtcctgatag gtccccctgc tgctgctgct gctgctc 47

<210> SEQ ID NO 90
<211> LENGTH: 47
<212> TYPE: DNA
<213> ORGANISM: Artificial Sequence
<220> FEATURE:
<223> OTHER INFORMATION: reporter sense strand

<400> SEQUENCE: 90
tcgagagcag cagcagcagc agcagcggga cctatcagga cagagtg 47

<210> SEQ ID NO 91
<211> LENGTH: 47
<212> TYPE: DNA
<213> ORGANISM: Artificial Sequence
<220> FEATURE:
<223> OTHER INFORMATION: reporter antisense strand

<400> SEQUENCE: 91
aattcactct gtcctgatag gtcccgctgc tgctgctgct gctgctc 47

<210> SEQ ID NO 92
<211> LENGTH: 47
<212> TYPE: DNA
<213> ORGANISM: Artificial Sequence
<220> FEATURE:
<223> OTHER INFORMATION: reporter sense strand

<400> SEQUENCE: 92
tcgagtgctg gagaccatcc actggcgtgg gcagatccgt catttcg 47

<210> SEQ ID NO 93
<211> LENGTH: 47
<212> TYPE: DNA
<213> ORGANISM: Artificial Sequence
<220> FEATURE:
<223> OTHER INFORMATION: reporter antisense strand

<400> SEQUENCE: 93
aattcgaaat gacggatctg cccacgccag tggatggtct ccagcac 47

<210> SEQ ID NO 94
<211> LENGTH: 47
<212> TYPE: DNA
<213> ORGANISM: Artificial Sequence
<220> FEATURE:
<223> OTHER INFORMATION: reporter sense strand

<400> SEQUENCE: 94
tcgagtgctg gagaccatcc actggtgtgg gcagatccgt catttcg 47

<210> SEQ ID NO 95
<211> LENGTH: 47
<212> TYPE: DNA
<213> ORGANISM: Artificial Sequence
<220> FEATURE:
<223> OTHER INFORMATION: reporter antisense strand

<400> SEQUENCE: 95
aattcgaaat gacggatctg cccacagcag tggatggtct ccagcac 47

<210> SEQ ID NO 96
<211> LENGTH: 47
<212> TYPE: DNA
<213> ORGANISM: Artificial Sequence
<220> FEATURE:
<223> OTHER INFORMATION: reporter sense strand

<400> SEQUENCE: 96
tcgaggaatc cattctggtg ccactaccac agctccttct ctgagtg 47

<210> SEQ ID NO 97
<211> LENGTH: 47
<212> TYPE: DNA
<213> ORGANISM: Artificial Sequence
<220> FEATURE:
<223> OTHER INFORMATION: reporter antisense strand

<400> SEQUENCE: 97
aattcactca gagaaggagc tgtggtagtg gcaccagaat ggattcc 47

<210> SEQ ID NO 98
<211> LENGTH: 47
<212> TYPE: DNA
<213> ORGANISM: Artificial Sequence
<220> FEATURE:

<223> OTHER INFORMATION: reporter sense strand

<400> SEQUENCE: 98
tcgaggaatc cattctggtg ccactgccac agctccttct ctgagtg 47

<210> SEQ ID NO 99
<211> LENGTH: 47
<212> TYPE: DNA
<213> ORGANISM: Artificial Sequence
<220> FEATURE:
<223> OTHER INFORMATION: reporter antisense strand

<400> SEQUENCE: 99
aattcactca gagaaggagc tgtggcagtg gcaccagaat ggattcc 47

<210> SEQ ID NO 100
<211> LENGTH: 47
<212> TYPE: DNA
<213> ORGANISM: Artificial Sequence
<220> FEATURE:
<223> OTHER INFORMATION: reporter sense strand

<400> SEQUENCE: 100
tcgagacccc gccgcctgct gctgacgggc acaccgctgc agaacag 47

<210> SEQ ID NO 101
<211> LENGTH: 47
<212> TYPE: DNA
<213> ORGANISM: Artificial Sequence
<220> FEATURE:
<223> OTHER INFORMATION: reporter antisense strand

<400> SEQUENCE: 101
aattctgttc tgcagcggtg tgcccgtcag cagcaggcgg cggggtc 47

<210> SEQ ID NO 102
<211> LENGTH: 47
<212> TYPE: DNA
<213> ORGANISM: Artificial Sequence
<220> FEATURE:
<223> OTHER INFORMATION: reporter sense strand

<400> SEQUENCE: 102
tcgagacccc gccgcctgct gctgatgggc acaccgctgc agaacag 47

<210> SEQ ID NO 103
<211> LENGTH: 47
<212> TYPE: DNA
<213> ORGANISM: Artificial Sequence
<220> FEATURE:
<223> OTHER INFORMATION: reporter antisense strand

<400> SEQUENCE: 103
aattctgttc tgcagcggtg tgcccatcag cagcaggcgg cggggtc 47

<210> SEQ ID NO 104
<211> LENGTH: 47
<212> TYPE: DNA
<213> ORGANISM: Artificial Sequence
<220> FEATURE:
<223> OTHER INFORMATION: reporter sense strand

<400> SEQUENCE: 104
tcgagtggcc ccaatcggcc tggtgctcat cgtgggaggc tacttcg 47

<210> SEQ ID NO 105
<211> LENGTH: 47
<212> TYPE: DNA
<213> ORGANISM: Artificial Sequence
<220> FEATURE:
<223> OTHER INFORMATION: reporter antisense strand

<400> SEQUENCE: 105
aattcgaagt agcctcccac gatgagcacc aggccgattg gggccac 47

<210> SEQ ID NO 106
<211> LENGTH: 47
<212> TYPE: DNA
<213> ORGANISM: Artificial Sequence
<220> FEATURE:
<223> OTHER INFORMATION: reporter sense strand

<400> SEQUENCE: 106
tcgagtggcc ccaatcggcc tggtgttcat cgtgggaggc tacttcg 47

<210> SEQ ID NO 107
<211> LENGTH: 47
<212> TYPE: DNA
<213> ORGANISM: Artificial Sequence
<220> FEATURE:
<223> OTHER INFORMATION: reporter antisense strand

<400> SEQUENCE: 107
aattcgaagt agcctcccac gatgaacacc aggccgattg gggccac 47

<210> SEQ ID NO 108
<211> LENGTH: 47
<212> TYPE: DNA
<213> ORGANISM: Artificial Sequence
<220> FEATURE:
<223> OTHER INFORMATION: reporter sense strand

<400> SEQUENCE: 108
tcgagcaagg ccttgcctgg cttccgcaac ttacacgtgg acgaccg 47

<210> SEQ ID NO 109
<211> LENGTH: 47
<212> TYPE: DNA
<213> ORGANISM: Artificial Sequence
<220> FEATURE:
<223> OTHER INFORMATION: reporter antisense strand

<400> SEQUENCE: 109
aattcggtcg tccacgtgta agttgcggaa gccaggcaag gccttgc 47

<210> SEQ ID NO 110
<211> LENGTH: 47
<212> TYPE: DNA
<213> ORGANISM: Artificial Sequence
<220> FEATURE:
<223> OTHER INFORMATION: reporter sense strand

<400> SEQUENCE: 110
tcgagcaagg ccttgcctgg cttcctcaac ttacacgtgg acgaccg 47

<210> SEQ ID NO 111
<211> LENGTH: 47
<212> TYPE: DNA
<213> ORGANISM: Artificial Sequence
<220> FEATURE:
<223> OTHER INFORMATION: reporter antisense strand

<400> SEQUENCE: 111
aattcggtcg tccacgtgta agttgaggaa gccaggcaag gccttgc 47

<210> SEQ ID NO 112
<211> LENGTH: 47
<212> TYPE: DNA
<213> ORGANISM: Artificial Sequence
<220> FEATURE:
<223> OTHER INFORMATION: reporter sense strand

<400> SEQUENCE: 112
tcgaggaatc aatcgcatct tccacgagcg gttcccattt gagctgg 47

<210> SEQ ID NO 113
<211> LENGTH: 47
<212> TYPE: DNA
<213> ORGANISM: Artificial Sequence
<220> FEATURE:
<223> OTHER INFORMATION: reporter antisense strand

<400> SEQUENCE: 113
aattccagct caaatgggaa ccgctcgtgg aagatgcgat tgattcc 47

<210> SEQ ID NO 114
<211> LENGTH: 47
<212> TYPE: DNA
<213> ORGANISM: Artificial Sequence
<220> FEATURE:
<223> OTHER INFORMATION: reporter sense strand

<400> SEQUENCE: 114
tcgaggaatc aatcgcatct tccacaagcg gttcccattt gagctgg 47

<210> SEQ ID NO 115
<211> LENGTH: 47
<212> TYPE: DNA
<213> ORGANISM: Artificial Sequence
<220> FEATURE:
<223> OTHER INFORMATION: reporter antisense strand

<400> SEQUENCE: 115
aattccagct caaatgggaa ccgcttgtgg aagatgcgat tgattcc 47

<210> SEQ ID NO 116
<211> LENGTH: 47
<212> TYPE: DNA
<213> ORGANISM: Artificial Sequence
<220> FEATURE:
<223> OTHER INFORMATION: reporter sense strand

<400> SEQUENCE: 116
tcgagtcaag accctcaaca acaagtttgc ctccttcatc gacaagg 47

<210> SEQ ID NO 117
<211> LENGTH: 47
<212> TYPE: DNA
<213> ORGANISM: Artificial Sequence
<220> FEATURE:
<223> OTHER INFORMATION: reporter antisense strand

<400> SEQUENCE: 117
aattccttgt cgatgaagga ggcaaacttg ttgttgaggg tcttgac 47

<210> SEQ ID NO 118
<211> LENGTH: 47

<212> TYPE: DNA
<213> ORGANISM: Artificial Sequence
<220> FEATURE:
<223> OTHER INFORMATION: reporter sense strand

<400> SEQUENCE: 118
tcgagtcaag accctcaaca acaaggttgc ctccttcatc gacaagg 47

<210> SEQ ID NO 119
<211> LENGTH: 47
<212> TYPE: DNA
<213> ORGANISM: Artificial Sequence
<220> FEATURE:
<223> OTHER INFORMATION: reporter antisense strand

<400> SEQUENCE: 119
aattccttgt cgatgaagga ggcaaccttg ttgttgaggg tcttgac 47

<210> SEQ ID NO 120
<211> LENGTH: 47
<212> TYPE: DNA
<213> ORGANISM: Artificial Sequence
<220> FEATURE:
<223> OTHER INFORMATION: reporter sense strand

<400> SEQUENCE: 120
tcgagtctcc gaagcccaca cgtgtatccc tgagaacaac ggaggcg 47

<210> SEQ ID NO 121
<211> LENGTH: 47
<212> TYPE: DNA
<213> ORGANISM: Artificial Sequence
<220> FEATURE:
<223> OTHER INFORMATION: reporter antisense strand

<400> SEQUENCE: 121
aattcgcctc cgttgttctc agggatacac gtgtgggctt cggagac 47

<210> SEQ ID NO 122
<211> LENGTH: 47
<212> TYPE: DNA
<213> ORGANISM: Artificial Sequence
<220> FEATURE:
<223> OTHER INFORMATION: reporter sense strand

<400> SEQUENCE: 122
tcgagtctcc gaagcccaca cgtgtgtccc tgagaacaac ggaggcg 47

<210> SEQ ID NO 123
<211> LENGTH: 47
<212> TYPE: DNA
<213> ORGANISM: Artificial Sequence
<220> FEATURE:
<223> OTHER INFORMATION: reporter antisense strand

<400> SEQUENCE: 123
aattcgcctc cgttgttctc agggacacac gtgtgggctt cggagac 47

<210> SEQ ID NO 124
<211> LENGTH: 47
<212> TYPE: DNA
<213> ORGANISM: Artificial Sequence
<220> FEATURE:
<223> OTHER INFORMATION: reporter sense strand

<400> SEQUENCE: 124

-continued tcgagcttac cgcagcttca gcaactccct gagccagtca ccgtgtg 47

<210> SEQ ID NO 125
<211> LENGTH: 47
<212> TYPE: DNA
<213> ORGANISM: Artificial Sequence
<220> FEATURE:
<223> OTHER INFORMATION: reporter antisense strand

<400> SEQUENCE: 125
aattcacacg gtgactggct cagggagttg ctgaagctgc ggtaagc 47

<210> SEQ ID NO 126
<211> LENGTH: 47
<212> TYPE: DNA
<213> ORGANISM: Artificial Sequence
<220> FEATURE:
<223> OTHER INFORMATION: reporter sense strand

<400> SEQUENCE: 126
tcgagcttac cgcagcttca gcaacccccct gagccagtca ccgtgtg 47

<210> SEQ ID NO 127
<211> LENGTH: 47
<212> TYPE: DNA
<213> ORGANISM: Artificial Sequence
<220> FEATURE:
<223> OTHER INFORMATION: reporter antisense strand

<400> SEQUENCE: 127
aattcacacg gtgactggct caggggggttg ctgaagctgc ggtaagc 47

<210> SEQ ID NO 128
<211> LENGTH: 47
<212> TYPE: DNA
<213> ORGANISM: Artificial Sequence
<220> FEATURE:
<223> OTHER INFORMATION: reporter sense strand

<400> SEQUENCE: 128
tcgagggata atatcaaaca cgtcccggga ggcggcagtg tgcaaag 47

<210> SEQ ID NO 129
<211> LENGTH: 47
<212> TYPE: DNA
<213> ORGANISM: Artificial Sequence
<220> FEATURE:
<223> OTHER INFORMATION: reporter antisense strand

<400> SEQUENCE: 129
aattctttgc acactgccgc ctcccgggac gtgtttgata ttatccc 47

<210> SEQ ID NO 130
<211> LENGTH: 47
<212> TYPE: DNA
<213> ORGANISM: Artificial Sequence
<220> FEATURE:
<223> OTHER INFORMATION: reporter sense strand

<400> SEQUENCE: 130
tcgagggata atatcaaaca cgtcctggga ggcggcagtg tgcaaag 47

<210> SEQ ID NO 131
<211> LENGTH: 47
<212> TYPE: DNA
<213> ORGANISM: Artificial Sequence
<220> FEATURE:
<223> OTHER INFORMATION: reporter antisense strand

<400> SEQUENCE: 131
aattctttgc acactgccgc ctcccaggac gtgtttgata ttatccc 47

<210> SEQ ID NO 132
<211> LENGTH: 47
<212> TYPE: DNA
<213> ORGANISM: Artificial Sequence
<220> FEATURE:
<223> OTHER INFORMATION: reporter sense strand

<400> SEQUENCE: 132
tcgagtgagt tggaagaccc aggggaaatg tctcctccca ttgattg 47

<210> SEQ ID NO 133
<211> LENGTH: 47
<212> TYPE: DNA
<213> ORGANISM: Artificial Sequence
<220> FEATURE:
<223> OTHER INFORMATION: reporter antisense strand

<400> SEQUENCE: 133
aattcaatca atgggaggag acatttcccc tgggtcttcc aactcac 47

<210> SEQ ID NO 134
<211> LENGTH: 47
<212> TYPE: DNA
<213> ORGANISM: Artificial Sequence
<220> FEATURE:
<223> OTHER INFORMATION: reporter sense strand

<400> SEQUENCE: 134
tcgagtgagt tggaagaccc agggggaatg tctcctccca ttgattg 47

<210> SEQ ID NO 135
<211> LENGTH: 47
<212> TYPE: DNA
<213> ORGANISM: Artificial Sequence
<220> FEATURE:
<223> OTHER INFORMATION: reporter antisense strand

<400> SEQUENCE: 135
aattcaatca atgggaggag acattccccc tgggtcttcc aactcac 47

<210> SEQ ID NO 136
<211> LENGTH: 47
<212> TYPE: DNA
<213> ORGANISM: Artificial Sequence
<220> FEATURE:
<223> OTHER INFORMATION: reporter sense strand

<400> SEQUENCE: 136
tcgagggcgg cggcagcagc agcgggggct gcgggcggtc ggggctg 47

<210> SEQ ID NO 137
<211> LENGTH: 47
<212> TYPE: DNA
<213> ORGANISM: Artificial Sequence
<220> FEATURE:
<223> OTHER INFORMATION: reporter antisense strand

<400> SEQUENCE: 137
aattcagccc cgaccgcccg cagcccccgc tgctgctgcc gccgccc 47

<210> SEQ ID NO 138
<211> LENGTH: 47
<212> TYPE: DNA
<213> ORGANISM: Artificial Sequence
<220> FEATURE:
<223> OTHER INFORMATION: reporter sense strand

<400> SEQUENCE: 138
tcgagggcgg cggcagcagc agcggcggct gcgggcggtc ggggctg 47

<210> SEQ ID NO 139
<211> LENGTH: 47
<212> TYPE: DNA
<213> ORGANISM: Artificial Sequence
<220> FEATURE:
<223> OTHER INFORMATION: reporter antisense strand

<400> SEQUENCE: 139
aattcagccc cgaccgcccg cagccgccgc tgctgctgcc gccgccc 47

<210> SEQ ID NO 140
<211> LENGTH: 47
<212> TYPE: DNA
<213> ORGANISM: Artificial Sequence
<220> FEATURE:
<223> OTHER INFORMATION: reporter sense strand

<400> SEQUENCE: 140
tcgaggacgg gtgtggtacg cagccccttc gagtacccac agtactg 47

<210> SEQ ID NO 141
<211> LENGTH: 47
<212> TYPE: DNA
<213> ORGANISM: Artificial Sequence
<220> FEATURE:
<223> OTHER INFORMATION: reporter antisense strand

<400> SEQUENCE: 141
aattcagtac tgtgggtact cgaaggggct gcgtaccaca cccgtcc 47

<210> SEQ ID NO 142
<211> LENGTH: 47
<212> TYPE: DNA
<213> ORGANISM: Artificial Sequence
<220> FEATURE:
<223> OTHER INFORMATION: reporter sense strand

<400> SEQUENCE: 142
tcgaggacgg gtgtggtacg cagccacttc gagtacccac agtactg 47

<210> SEQ ID NO 143
<211> LENGTH: 47
<212> TYPE: DNA
<213> ORGANISM: Artificial Sequence
<220> FEATURE:
<223> OTHER INFORMATION: reporter antisense strand

<400> SEQUENCE: 143
aattcagtac tgtgggtact cgaagtggct gcgtaccaca cccgtcc 47

<210> SEQ ID NO 144
<211> LENGTH: 47
<212> TYPE: DNA
<213> ORGANISM: Artificial Sequence
<220> FEATURE:
<223> OTHER INFORMATION: reporter sense strand

<400> SEQUENCE: 144
tcgagcggag acgagccagg tggcctcggc ctaagacctg cctaggg 47

<210> SEQ ID NO 145
<211> LENGTH: 47
<212> TYPE: DNA
<213> ORGANISM: Artificial Sequence
<220> FEATURE:
<223> OTHER INFORMATION: reporter antisense strand

<400> SEQUENCE: 145
aattccctag gcaggtctta ggccgaggcc acctggctcg tctccgc 47

<210> SEQ ID NO 146
<211> LENGTH: 47
<212> TYPE: DNA
<213> ORGANISM: Artificial Sequence
<220> FEATURE:
<223> OTHER INFORMATION: reporter sense strand

<400> SEQUENCE: 146
tcgagtgaga acattcagag ttctccgagc attgaagacg atttcag 47

<210> SEQ ID NO 147
<211> LENGTH: 47
<212> TYPE: DNA
<213> ORGANISM: Artificial Sequence
<220> FEATURE:
<223> OTHER INFORMATION: reporter antisense strand

<400> SEQUENCE: 147
aattctgaaa tcgtcttcaa tgctcggaga actctgaatg ttctcac 47

<210> SEQ ID NO 148
<211> LENGTH: 47
<212> TYPE: DNA
<213> ORGANISM: Artificial Sequence
<220> FEATURE:
<223> OTHER INFORMATION: reporter sense strand

<400> SEQUENCE: 148
tcgagtgaga acattcagag ttctctgagc attgaagacg atttcag 47

<210> SEQ ID NO 149
<211> LENGTH: 47
<212> TYPE: DNA
<213> ORGANISM: Artificial Sequence
<220> FEATURE:
<223> OTHER INFORMATION: reporter antisense strand

<400> SEQUENCE: 149
aattctgaaa tcgtcttcaa tgctcagaga actctgaatg ttctcac 47

<210> SEQ ID NO 150
<211> LENGTH: 47
<212> TYPE: DNA
<213> ORGANISM: Artificial Sequence
<220> FEATURE:
<223> OTHER INFORMATION: reporter sense strand

<400> SEQUENCE: 150
tcgagcttga attccaagag cacacggtct tcagtgaagc tgcaggg 47

<210> SEQ ID NO 151

<211> LENGTH: 47
<212> TYPE: DNA
<213> ORGANISM: Artificial Sequence
<220> FEATURE:
<223> OTHER INFORMATION: reporter antisense strand

<400> SEQUENCE: 151
aattccctgc agcttcactg aagaccgtgt gctcttggaa ttcaagc 47

<210> SEQ ID NO 152
<211> LENGTH: 47
<212> TYPE: DNA
<213> ORGANISM: Artificial Sequence
<220> FEATURE:
<223> OTHER INFORMATION: reporter sense strand

<400> SEQUENCE: 152
tcgagcttga attccaagag cacacagtct tcagtgaagc tgcaggg 47

<210> SEQ ID NO 153
<211> LENGTH: 47
<212> TYPE: DNA
<213> ORGANISM: Artificial Sequence
<220> FEATURE:
<223> OTHER INFORMATION: reporter antisense strand

<400> SEQUENCE: 153
aattccctgc agcttcactg aagactgtgt gctcttggaa ttcaagc 47

<210> SEQ ID NO 154
<211> LENGTH: 47
<212> TYPE: DNA
<213> ORGANISM: Artificial Sequence
<220> FEATURE:
<223> OTHER INFORMATION: reporter sense strand

<400> SEQUENCE: 154
tcgagaccgc cgaagcctca gcccacgacc cggaccccgc ctcagtg 47

<210> SEQ ID NO 155
<211> LENGTH: 47
<212> TYPE: DNA
<213> ORGANISM: Artificial Sequence
<220> FEATURE:
<223> OTHER INFORMATION: reporter antisense strand

<400> SEQUENCE: 155
aattcactga ggcggggtcc gggtcgtggg ctgaggcttc ggcggtc 47

<210> SEQ ID NO 156
<211> LENGTH: 47
<212> TYPE: DNA
<213> ORGANISM: Artificial Sequence
<220> FEATURE:
<223> OTHER INFORMATION: reporter sense strand

<400> SEQUENCE: 156
tcgagaccgc cgaagcctca gcccaggacc cggaccccgc ctcagtg 47

<210> SEQ ID NO 157
<211> LENGTH: 47
<212> TYPE: DNA
<213> ORGANISM: Artificial Sequence
<220> FEATURE:
<223> OTHER INFORMATION: reporter antisense strand

<400> SEQUENCE: 157
aattcactga ggcggggtcc gggtcctggg ctgaggcttc ggcggtc 47

<210> SEQ ID NO 158
<211> LENGTH: 47
<212> TYPE: DNA
<213> ORGANISM: Artificial Sequence
<220> FEATURE:
<223> OTHER INFORMATION: reporter sense strand

<400> SEQUENCE: 158
tcgagtgttc cgggccctgg gcctgcggca cctggtggtg gtggacg 47

<210> SEQ ID NO 159
<211> LENGTH: 47
<212> TYPE: DNA
<213> ORGANISM: Artificial Sequence
<220> FEATURE:
<223> OTHER INFORMATION: reporter antisense strand

<400> SEQUENCE: 159
aattcgtcca ccaccaccag gtgccgcagg cccagggccc ggaacac 47

<210> SEQ ID NO 160
<211> LENGTH: 47
<212> TYPE: DNA
<213> ORGANISM: Artificial Sequence
<220> FEATURE:
<223> OTHER INFORMATION: reporter sense strand

<400> SEQUENCE: 160
tcgagtgttc cgggccctgg gcctgtggca cctggtggtg gtggacg 47

<210> SEQ ID NO 161
<211> LENGTH: 47
<212> TYPE: DNA
<213> ORGANISM: Artificial Sequence
<220> FEATURE:
<223> OTHER INFORMATION: reporter antisense strand

<400> SEQUENCE: 161
aattcgtcca ccaccaccag gtgccacagg cccagggccc ggaacac 47

<210> SEQ ID NO 162
<211> LENGTH: 47
<212> TYPE: DNA
<213> ORGANISM: Artificial Sequence
<220> FEATURE:
<223> OTHER INFORMATION: reporter sense strand

<400> SEQUENCE: 162
tcgagtcccc tccatcatga atgtgctgct ggtgtgtctc atcttcg 47

<210> SEQ ID NO 163
<211> LENGTH: 47
<212> TYPE: DNA
<213> ORGANISM: Artificial Sequence
<220> FEATURE:
<223> OTHER INFORMATION: reporter antisense strand

<400> SEQUENCE: 163
aattcgaaga tgagacacac cagcagcaca ttcatgatgg aggggac 47

<210> SEQ ID NO 164
<211> LENGTH: 47
<212> TYPE: DNA

-continued

<213> ORGANISM: Artificial Sequence
<220> FEATURE:
<223> OTHER INFORMATION: reporter sense strand

<400> SEQUENCE: 164
tcgagtcccc tccatcatga atgtggtgct ggtgtgtctc atcttcg 47

<210> SEQ ID NO 165
<211> LENGTH: 47
<212> TYPE: DNA
<213> ORGANISM: Artificial Sequence
<220> FEATURE:
<223> OTHER INFORMATION: reporter antisense strand

<400> SEQUENCE: 165
aattcgaaga tgagacacac cagcaccaca ttcatgatgg aggggac 47

<210> SEQ ID NO 166
<211> LENGTH: 47
<212> TYPE: DNA
<213> ORGANISM: Artificial Sequence
<220> FEATURE:
<223> OTHER INFORMATION: reporter sense strand

<400> SEQUENCE: 166
tcgagacatc attggtgcct ccagcgactg cagcacctgc tttgtgg 47

<210> SEQ ID NO 167
<211> LENGTH: 47
<212> TYPE: DNA
<213> ORGANISM: Artificial Sequence
<220> FEATURE:
<223> OTHER INFORMATION: reporter antisense strand

<400> SEQUENCE: 167
aattccacaa agcaggtgct gcagtcgctg gaggcaccaa tgatgtc 47

<210> SEQ ID NO 168
<211> LENGTH: 47
<212> TYPE: DNA
<213> ORGANISM: Artificial Sequence
<220> FEATURE:
<223> OTHER INFORMATION: reporter sense strand

<400> SEQUENCE: 168
tcgagacatc attggtgcct ccagctactg cagcacctgc tttgtgg 47

<210> SEQ ID NO 169
<211> LENGTH: 47
<212> TYPE: DNA
<213> ORGANISM: Artificial Sequence
<220> FEATURE:
<223> OTHER INFORMATION: reporter antisense strand

<400> SEQUENCE: 169
aattccacaa agcaggtgct gcagtagctg gaggcaccaa tgatgtc 47

<210> SEQ ID NO 170
<211> LENGTH: 47
<212> TYPE: DNA
<213> ORGANISM: Artificial Sequence
<220> FEATURE:
<223> OTHER INFORMATION: reporter sense strand

<400> SEQUENCE: 170
tcgagtcaag accctcaaca acaagtttgc ctccttcatc gacaagg 47

<210> SEQ ID NO 171
<211> LENGTH: 47
<212> TYPE: DNA
<213> ORGANISM: Artificial Sequence
<220> FEATURE:
<223> OTHER INFORMATION: reporter antisense strand

<400> SEQUENCE: 171
aattccttgt cgatgaagga ggcaaacttg ttgttgaggg tcttgac 47

<210> SEQ ID NO 172
<211> LENGTH: 47
<212> TYPE: DNA
<213> ORGANISM: Artificial Sequence
<220> FEATURE:
<223> OTHER INFORMATION: reporter sense strand

<400> SEQUENCE: 172
tcgagtcaag accctcaaca acaaggttgc ctccttcatc gacaagg 47

<210> SEQ ID NO 173
<211> LENGTH: 47
<212> TYPE: DNA
<213> ORGANISM: Artificial Sequence
<220> FEATURE:
<223> OTHER INFORMATION: reporter antisense strand

<400> SEQUENCE: 173
aattccttgt cgatgaagga ggcaaccttg ttgttgaggg tcttgac 47

<210> SEQ ID NO 174
<211> LENGTH: 21
<212> TYPE: RNA
<213> ORGANISM: Artificial Sequence
<220> FEATURE:
<223> OTHER INFORMATION: siRNA

<400> SEQUENCE: 174
ccacaguacu ucaacgcuag a 21

<210> SEQ ID NO 175
<211> LENGTH: 21
<212> TYPE: RNA
<213> ORGANISM: Artificial Sequence
<220> FEATURE:
<223> OTHER INFORMATION: siRNA

<400> SEQUENCE: 175
uagcguugaa guacuguggg g 21

<210> SEQ ID NO 176
<211> LENGTH: 21
<212> TYPE: RNA
<213> ORGANISM: Artificial Sequence
<220> FEATURE:
<223> OTHER INFORMATION: siRNA

<400> SEQUENCE: 176
gaagucugcg cccuugugcc c 21

<210> SEQ ID NO 177
<211> LENGTH: 21
<212> TYPE: RNA
<213> ORGANISM: Artificial Sequence
<220> FEATURE:

<223> OTHER INFORMATION: siRNA

<400> SEQUENCE: 177
gcacaagggc gcagacuucc a 21

<210> SEQ ID NO 178
<211> LENGTH: 21
<212> TYPE: RNA
<213> ORGANISM: Artificial Sequence
<220> FEATURE:
<223> OTHER INFORMATION: siRNA

<400> SEQUENCE: 178
cccucaucua cugugugcac u 21

<210> SEQ ID NO 179
<211> LENGTH: 21
<212> TYPE: RNA
<213> ORGANISM: Artificial Sequence
<220> FEATURE:
<223> OTHER INFORMATION: siRNA

<400> SEQUENCE: 179
ugcacacagu agaugaggga g 21

<210> SEQ ID NO 180
<211> LENGTH: 21
<212> TYPE: RNA
<213> ORGANISM: Artificial Sequence
<220> FEATURE:
<223> OTHER INFORMATION: siRNA

<400> SEQUENCE: 180
agcagcaggg ggaccuauca g 21

<210> SEQ ID NO 181
<211> LENGTH: 21
<212> TYPE: RNA
<213> ORGANISM: Artificial Sequence
<220> FEATURE:
<223> OTHER INFORMATION: siRNA

<400> SEQUENCE: 181
agcagcaggg ggaccuauca g 21

<210> SEQ ID NO 182
<211> LENGTH: 21
<212> TYPE: RNA
<213> ORGANISM: Artificial Sequence
<220> FEATURE:
<223> OTHER INFORMATION: siRNA

<400> SEQUENCE: 182
uccacuggcg ugggcagauc c 21

<210> SEQ ID NO 183
<211> LENGTH: 21
<212> TYPE: RNA
<213> ORGANISM: Artificial Sequence
<220> FEATURE:
<223> OTHER INFORMATION: siRNA

<400> SEQUENCE: 183
aucugcccac gccaguggau g 21

<210> SEQ ID NO 184
<211> LENGTH: 21
<212> TYPE: RNA
<213> ORGANISM: Artificial Sequence
<220> FEATURE:
<223> OTHER INFORMATION: siRNA

<400> SEQUENCE: 184
gugccacuac cacagcuccu u 21

<210> SEQ ID NO 185
<211> LENGTH: 21
<212> TYPE: RNA
<213> ORGANISM: Artificial Sequence
<220> FEATURE:
<223> OTHER INFORMATION: siRNA

<400> SEQUENCE: 185
ggagcugugg uaguggcacc a 21

<210> SEQ ID NO 186
<211> LENGTH: 21
<212> TYPE: RNA
<213> ORGANISM: Artificial Sequence
<220> FEATURE:
<223> OTHER INFORMATION: siRNA

<400> SEQUENCE: 186
gcugcugacg ggcacaccgc u 21

<210> SEQ ID NO 187
<211> LENGTH: 21
<212> TYPE: RNA
<213> ORGANISM: Artificial Sequence
<220> FEATURE:
<223> OTHER INFORMATION: siRNA

<400> SEQUENCE: 187
cggugugccc gucagcagca g 21

<210> SEQ ID NO 188
<211> LENGTH: 21
<212> TYPE: RNA
<213> ORGANISM: Artificial Sequence
<220> FEATURE:
<223> OTHER INFORMATION: siRNA

<400> SEQUENCE: 188
gccuggugcu caucguggga g 21

<210> SEQ ID NO 189
<211> LENGTH: 21
<212> TYPE: RNA
<213> ORGANISM: Artificial Sequence
<220> FEATURE:
<223> OTHER INFORMATION: siRNA

<400> SEQUENCE: 189
cccacgauga gcaccaggcc g 21

<210> SEQ ID NO 190
<211> LENGTH: 21
<212> TYPE: RNA
<213> ORGANISM: Artificial Sequence
<220> FEATURE:
<223> OTHER INFORMATION: siRNA

<400> SEQUENCE: 190
gcacaguaau ucaucgcuag a 21

<210> SEQ ID NO 191
<211> LENGTH: 21
<212> TYPE: RNA
<213> ORGANISM: Artificial Sequence
<220> FEATURE:
<223> OTHER INFORMATION: siRNA

<400> SEQUENCE: 191
uagcgaugaa uuacugugcg g 21

<210> SEQ ID NO 192
<211> LENGTH: 21
<212> TYPE: RNA
<213> ORGANISM: Artificial Sequence
<220> FEATURE:
<223> OTHER INFORMATION: siRNA

<400> SEQUENCE: 192
gaagucugug cccaugugac c 21

<210> SEQ ID NO 193
<211> LENGTH: 21
<212> TYPE: RNA
<213> ORGANISM: Artificial Sequence
<220> FEATURE:
<223> OTHER INFORMATION: siRNA

<400> SEQUENCE: 193
ucacaugggc acagacuucc a 21

<210> SEQ ID NO 194
<211> LENGTH: 21
<212> TYPE: RNA
<213> ORGANISM: Artificial Sequence
<220> FEATURE:
<223> OTHER INFORMATION: siRNA

<400> SEQUENCE: 194
gccucaucca cugagugcac u 21

<210> SEQ ID NO 195
<211> LENGTH: 21
<212> TYPE: RNA
<213> ORGANISM: Artificial Sequence
<220> FEATURE:
<223> OTHER INFORMATION: siRNA

<400> SEQUENCE: 195
ugcacucagu ggaugaggca g 21

<210> SEQ ID NO 196
<211> LENGTH: 21
<212> TYPE: RNA
<213> ORGANISM: Artificial Sequence
<220> FEATURE:
<223> OTHER INFORMATION: siRNA

<400> SEQUENCE: 196
ggcagcagcg ggagcuauaa g 21

<210> SEQ ID NO 197
<211> LENGTH: 21

<212> TYPE: RNA
<213> ORGANISM: Artificial Sequence
<220> FEATURE:
<223> OTHER INFORMATION: siRNA

<400> SEQUENCE: 197
uauagcuccc gcugcugccg c 21

<210> SEQ ID NO 198
<211> LENGTH: 21
<212> TYPE: RNA
<213> ORGANISM: Artificial Sequence
<220> FEATURE:
<223> OTHER INFORMATION: siRNA

<400> SEQUENCE: 198
gccacuggug uggccagaac c 21

<210> SEQ ID NO 199
<211> LENGTH: 21
<212> TYPE: RNA
<213> ORGANISM: Artificial Sequence
<220> FEATURE:
<223> OTHER INFORMATION: siRNA

<400> SEQUENCE: 199
uucuggccac accaguggcu g 21

<210> SEQ ID NO 200
<211> LENGTH: 21
<212> TYPE: RNA
<213> ORGANISM: Artificial Sequence
<220> FEATURE:
<223> OTHER INFORMATION: siRNA

<400> SEQUENCE: 200
gugccacugc cacugcucau u 21

<210> SEQ ID NO 201
<211> LENGTH: 21
<212> TYPE: RNA
<213> ORGANISM: Artificial Sequence
<220> FEATURE:
<223> OTHER INFORMATION: siRNA

<400> SEQUENCE: 201
ugagcagugg caguggcacc a 21

<210> SEQ ID NO 202
<211> LENGTH: 21
<212> TYPE: RNA
<213> ORGANISM: Artificial Sequence
<220> FEATURE:
<223> OTHER INFORMATION: siRNA

<400> SEQUENCE: 202
gcugcugaug ggcucaccac u 21

<210> SEQ ID NO 203
<211> LENGTH: 21
<212> TYPE: RNA
<213> ORGANISM: Artificial Sequence
<220> FEATURE:
<223> OTHER INFORMATION: siRNA

<400> SEQUENCE: 203
uggugagccc aucagcagca g 21

<210> SEQ ID NO 204
<211> LENGTH: 21
<212> TYPE: RNA
<213> ORGANISM: Artificial Sequence
<220> FEATURE:
<223> OTHER INFORMATION: siRNA

<400> SEQUENCE: 204
gccugguguu caugguggaa g 21

<210> SEQ ID NO 205
<211> LENGTH: 21
<212> TYPE: RNA
<213> ORGANISM: Artificial Sequence
<220> FEATURE:
<223> OTHER INFORMATION: siRNA

<400> SEQUENCE: 205
gccaccauga acaccaggcc g 21

<210> SEQ ID NO 206
<211> LENGTH: 21
<212> TYPE: RNA
<213> ORGANISM: Artificial Sequence
<220> FEATURE:
<223> OTHER INFORMATION: siRNA

<400> SEQUENCE: 206
gggcuuccuc aacauacaag u 21

<210> SEQ ID NO 207
<211> LENGTH: 21
<212> TYPE: RNA
<213> ORGANISM: Artificial Sequence
<220> FEATURE:
<223> OTHER INFORMATION: siRNA

<400> SEQUENCE: 207
uuguauguug aggaagcccg g 21

<210> SEQ ID NO 208
<211> LENGTH: 21
<212> TYPE: RNA
<213> ORGANISM: Artificial Sequence
<220> FEATURE:
<223> OTHER INFORMATION: siRNA

<400> SEQUENCE: 208
gcuuccacaa gcgcuuccaa u 21

<210> SEQ ID NO 209
<211> LENGTH: 21
<212> TYPE: RNA
<213> ORGANISM: Artificial Sequence
<220> FEATURE:
<223> OTHER INFORMATION: siRNA

<400> SEQUENCE: 209
uggaagcgcu uguggaagcu g 21

<210> SEQ ID NO 210
<211> LENGTH: 21
<212> TYPE: RNA
<213> ORGANISM: Artificial Sequence
<220> FEATURE:
<223> OTHER INFORMATION: siRNA

<400> SEQUENCE: 210
ggagcagccg gccgagcuac g 21

<210> SEQ ID NO 211
<211> LENGTH: 21
<212> TYPE: RNA
<213> ORGANISM: Artificial Sequence
<220> FEATURE:
<223> OTHER INFORMATION: siRNA

<400> SEQUENCE: 211
uagcucggcc ggcugcuccu c 21

<210> SEQ ID NO 212
<211> LENGTH: 21
<212> TYPE: RNA
<213> ORGANISM: Artificial Sequence
<220> FEATURE:
<223> OTHER INFORMATION: siRNA

<400> SEQUENCE: 212
gcacgugugu cccagagaac a 21

<210> SEQ ID NO 213
<211> LENGTH: 21
<212> TYPE: RNA
<213> ORGANISM: Artificial Sequence
<220> FEATURE:
<223> OTHER INFORMATION: siRNA

<400> SEQUENCE: 213
uucucuggga cacacgugcg g 21

<210> SEQ ID NO 214
<211> LENGTH: 21
<212> TYPE: RNA
<213> ORGANISM: Artificial Sequence
<220> FEATURE:
<223> OTHER INFORMATION: siRNA

<400> SEQUENCE: 214
gcagcaaccc ccucagccag u 21

<210> SEQ ID NO 215
<211> LENGTH: 21
<212> TYPE: RNA
<213> ORGANISM: Artificial Sequence
<220> FEATURE:
<223> OTHER INFORMATION: siRNA

<400> SEQUENCE: 215
uggcugaggg gguugcugca g 21

<210> SEQ ID NO 216
<211> LENGTH: 21
<212> TYPE: RNA
<213> ORGANISM: Artificial Sequence
<220> FEATURE:
<223> OTHER INFORMATION: siRNA

<400> SEQUENCE: 216
gcacguccug ggacgcggaa g 21

<210> SEQ ID NO 217
<211> LENGTH: 21
<212> TYPE: RNA
<213> ORGANISM: Artificial Sequence
<220> FEATURE:
<223> OTHER INFORMATION: siRNA

<400> SEQUENCE: 217
uccgcguccc aggacgugcu u 21

<210> SEQ ID NO 218
<211> LENGTH: 21
<212> TYPE: RNA
<213> ORGANISM: Artificial Sequence
<220> FEATURE:
<223> OTHER INFORMATION: siRNA

<400> SEQUENCE: 218
gccaggggga augacuccac c 21

<210> SEQ ID NO 219
<211> LENGTH: 21
<212> TYPE: RNA
<213> ORGANISM: Artificial Sequence
<220> FEATURE:
<223> OTHER INFORMATION: siRNA

<400> SEQUENCE: 219
uggagucauu cccccuggcu c 21

<210> SEQ ID NO 220
<211> LENGTH: 21
<212> TYPE: RNA
<213> ORGANISM: Artificial Sequence
<220> FEATURE:
<223> OTHER INFORMATION: siRNA

<400> SEQUENCE: 220
ggcagcggcg gcuccgggag g 21

<210> SEQ ID NO 221
<211> LENGTH: 21
<212> TYPE: RNA
<213> ORGANISM: Artificial Sequence
<220> FEATURE:
<223> OTHER INFORMATION: siRNA

<400> SEQUENCE: 221
ucccggagcc gccgcugccg c 21

<210> SEQ ID NO 222
<211> LENGTH: 21
<212> TYPE: RNA
<213> ORGANISM: Artificial Sequence
<220> FEATURE:
<223> OTHER INFORMATION: siRNA

<400> SEQUENCE: 222
gcgcagccac uuccaguaac c 21

<210> SEQ ID NO 223
<211> LENGTH: 21
<212> TYPE: RNA
<213> ORGANISM: Artificial Sequence
<220> FEATURE:
<223> OTHER INFORMATION: siRNA

<400> SEQUENCE: 223
uuacuggaag uggcugcgca c 21

<210> SEQ ID NO 224
<211> LENGTH: 21
<212> TYPE: RNA
<213> ORGANISM: Artificial Sequence
<220> FEATURE:
<223> OTHER INFORMATION: siRNA

<400> SEQUENCE: 224
ggguggccuc ggcguaagac c 21

<210> SEQ ID NO 225
<211> LENGTH: 21
<212> TYPE: RNA
<213> ORGANISM: Artificial Sequence
<220> FEATURE:
<223> OTHER INFORMATION: siRNA

<400> SEQUENCE: 225
ucuuacgccg aggccacccg g 21

<210> SEQ ID NO 226
<211> LENGTH: 21
<212> TYPE: RNA
<213> ORGANISM: Artificial Sequence
<220> FEATURE:
<223> OTHER INFORMATION: siRNA

<400> SEQUENCE: 226
gaguucucug agcuuugaag a 21

<210> SEQ ID NO 227
<211> LENGTH: 21
<212> TYPE: RNA
<213> ORGANISM: Artificial Sequence
<220> FEATURE:
<223> OTHER INFORMATION: siRNA

<400> SEQUENCE: 227
uucaaagcuc agagaacucu g 21

<210> SEQ ID NO 228
<211> LENGTH: 21
<212> TYPE: RNA
<213> ORGANISM: Artificial Sequence
<220> FEATURE:
<223> OTHER INFORMATION: siRNA

<400> SEQUENCE: 228
gagcacacag ucuacaguaa a 21

<210> SEQ ID NO 229
<211> LENGTH: 21
<212> TYPE: RNA
<213> ORGANISM: Artificial Sequence
<220> FEATURE:
<223> OTHER INFORMATION: siRNA

<400> SEQUENCE: 229
uacuguagac ugugugcucu u 21

<210> SEQ ID NO 230

<211> LENGTH: 21
<212> TYPE: RNA
<213> ORGANISM: Artificial Sequence
<220> FEATURE:
<223> OTHER INFORMATION: siRNA

<400> SEQUENCE: 230
gcagcccagg accgggacac c 21

<210> SEQ ID NO 231
<211> LENGTH: 21
<212> TYPE: RNA
<213> ORGANISM: Artificial Sequence
<220> FEATURE:
<223> OTHER INFORMATION: siRNA

<400> SEQUENCE: 231
ugucccgguc cugggcugcg g 21

<210> SEQ ID NO 232
<211> LENGTH: 21
<212> TYPE: RNA
<213> ORGANISM: Artificial Sequence
<220> FEATURE:
<223> OTHER INFORMATION: siRNA

<400> SEQUENCE: 232
ggacccggac gccguggacc a 21

<210> SEQ ID NO 233
<211> LENGTH: 21
<212> TYPE: RNA
<213> ORGANISM: Artificial Sequence
<220> FEATURE:
<223> OTHER INFORMATION: siRNA

<400> SEQUENCE: 233
uccagcugcc acaggccccg g 21

<210> SEQ ID NO 234
<211> LENGTH: 21
<212> TYPE: RNA
<213> ORGANISM: Artificial Sequence
<220> FEATURE:
<223> OTHER INFORMATION: siRNA

<400> SEQUENCE: 234
ggaauguggu gcucguguau c 21

<210> SEQ ID NO 235
<211> LENGTH: 21
<212> TYPE: RNA
<213> ORGANISM: Artificial Sequence
<220> FEATURE:
<223> OTHER INFORMATION: siRNA

<400> SEQUENCE: 235
uacacgagca ccacauuccu g 21

<210> SEQ ID NO 236
<211> LENGTH: 21
<212> TYPE: RNA
<213> ORGANISM: Artificial Sequence
<220> FEATURE:
<223> OTHER INFORMATION: siRNA

<400> SEQUENCE: 236

-continued

```
gcuccagcua cuggagcaac u                                          21


<210> SEQ ID NO 237
<211> LENGTH: 21
<212> TYPE: RNA
<213> ORGANISM: Artificial Sequence
<220> FEATURE:
<223> OTHER INFORMATION: siRNA

<400> SEQUENCE: 237

uugcuccagu agcuggagcc a                                          21


<210> SEQ ID NO 238
<211> LENGTH: 21
<212> TYPE: RNA
<213> ORGANISM: Artificial Sequence
<220> FEATURE:
<223> OTHER INFORMATION: siRNA

<400> SEQUENCE: 238

gcaacaaggu ugcguccuac a                                          21


<210> SEQ ID NO 239
<211> LENGTH: 21
<212> TYPE: RNA
<213> ORGANISM: Artificial Sequence
<220> FEATURE:
<223> OTHER INFORMATION: siRNA

<400> SEQUENCE: 239

uaggacgcaa ccuuguugcu g                                          21
```